US009556195B2

(12) United States Patent
Sletten et al.

(10) Patent No.: US 9,556,195 B2
(45) Date of Patent: Jan. 31, 2017

(54) COMPOSITIONS AND METHODS FOR QUADRICYCLANE MODIFICATION OF BIOMOLECULES

(75) Inventors: Ellen May Sletten, Berkeley, CA (US); Carolyn Ruth Bertozzi, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 604 days.

(21) Appl. No.: 13/605,695

(22) Filed: Sep. 6, 2012

(65) Prior Publication Data

US 2013/0244267 A1 Sep. 19, 2013

Related U.S. Application Data

(60) Provisional application No. 61/533,607, filed on Sep. 12, 2011.

(51) Int. Cl.

| | | |
|---|---|---|
| *C07F 15/04* | (2006.01) | |
| *C07D 495/04* | (2006.01) | |
| *C07D 249/12* | (2006.01) | |
| *C07C 245/04* | (2006.01) | |
| *C07C 69/76* | (2006.01) | |
| *C07D 339/06* | (2006.01) | |
| *C07C 49/04* | (2006.01) | |
| *C07C 49/76* | (2006.01) | |
| *C07C 69/013* | (2006.01) | |
| *C12N 5/071* | (2010.01) | |
| *G01N 33/50* | (2006.01) | |
| *C07D 225/02* | (2006.01) | |
| *C07D 249/04* | (2006.01) | |
| *C07C 323/16* | (2006.01) | |
| *C07C 323/56* | (2006.01) | |
| *C07C 323/64* | (2006.01) | |

(52) U.S. Cl.
CPC ............ *C07D 495/04* (2013.01); *C07C 49/04* (2013.01); *C07C 49/76* (2013.01); *C07C 69/013* (2013.01); *C07C 69/76* (2013.01); *C07C 245/04* (2013.01); *C07C 323/16* (2013.01); *C07C 323/56* (2013.01); *C07C 323/64* (2013.01); *C07D 225/02* (2013.01); *C07D 249/04* (2013.01); *C07D 249/12* (2013.01); *C07D 339/06* (2013.01); *C07F 15/045* (2013.01); *C12N 5/0602* (2013.01); *G01N 33/5005* (2013.01)

(58) Field of Classification Search
CPC ..................................................... C07F 15/045
See application file for complete search history.

(56) References Cited

U.S. PATENT DOCUMENTS

| | | |
|---|---|---|
| 6,570,040 B2 | 5/2003 | Saxon et al. |
| 7,808,619 B2 | 10/2010 | Gerner et al. |
| 7,842,830 B2 | 11/2010 | Marder et al. |
| 2009/0068738 A1 | 3/2009 | Bertozzi et al. |

FOREIGN PATENT DOCUMENTS

| | | | | |
|---|---|---|---|---|
| JP | 2008-291072 A | * | 12/2008 | ............. C09D 11/00 |
| WO | WO/2008/038569 A2 | * | 4/2008 | ............... G02B 5/22 |
| WO | WO 2010/050574 A1 | * | 5/2010 | ............ H01M 14/00 |

OTHER PUBLICATIONS

Matsuzaki et al., CAS Accession No. 2000:377093.*
Yamamuro et al., CAS Accession No. 1987:58998.*
Horie et al. "Discotic liquid crystals of transition metalcomplexes, 31:establishment of mesomorphism and thermochromism of bis[1,2-bis(4-n-alkoxyphenyl)ethane-1,2-dithiolene]nickelcomplexes" Journal of Materials Chemistry, 2001, vol. 11, pp. 1063-1071.*
Petrov, et al., "Synthetic Chemistry of Quadricyclane", 2006, Current Organic Synthesis, vol. 3, No. 2, pp. 215-259.
Sletten, et al., "Bioorthogonal Chemistry: Fishing for Selectivity in a Sea of Functionality", 2009, Angew Chem., vol. 48,(38) pp. 6974-6998.
Sletten, et al., "A Bioorthogonal Quadricyclane Ligation", 2011, Journal of the American Chemical Society, vol. 133, pp. 17570-17573.

* cited by examiner

*Primary Examiner* — Joseph Kosack
(74) *Attorney, Agent, or Firm* — Bozicevic Field & Francis, LLP; Paula A. Borden; Glenn J. Foulds

(57) ABSTRACT

The present disclosure features a strain-promoted [2+2+2] reaction that can be carried out under physiological conditions. In general, the reaction involves reacting a pi-electrophile with a low lying LUMO with a quadricyclane on a biomolecule, generating a covalently modified biomolecule. The selectivity of the reaction and its compatibility with aqueous environments provides for its application in vivo and in vitro. The reaction is compatible with modification of living cells. In certain embodiments, the pi-electrophile can comprise a molecule of interest that is desired for delivery to a quadricyclane-containing biomolecule via [2+2+2] reaction.

15 Claims, 23 Drawing Sheets

A

B

COMPOSITIONS AND METHODS FOR QUADRICYCLANE MODIFICATION OF BIOMOLECULES

CROSS-REFERENCE

This application claims the benefit of U.S. Provisional Patent Application No. 61/533,607, filed Sep. 12, 2011, which application is incorporated herein by reference in its entirety.

STATEMENT REGARDING FEDERALLY SPONSORED RESEARCH

This invention was made with government support under Grant No. GM058867 awarded by the National Institutes of Health. The government has certain rights in the invention.

BACKGROUND

Bioorthogonal transformations include four broad reaction types: 1,3-dipolar cycloadditions, Diels-Alder reactions, metal-catalyzed couplings, and nucleophilic additions. Outside of this space lies the [2+2+2] cycloaddition reaction, a choice for the rapid assembly of functionalized ring systems. In practice, such reactions are typically metal catalyzed as a means to overcome an otherwise significant entropic barrier. However, the highly strained hydrocarbon quadricyclane directly undergoes [2+2+2] cycloaddition with specific types of pi systems.

Literature

U.S. Pat. No. 7,808,619; U.S. Patent Publication No. 2009/0068738; U.S. Pat. No. 6,570,040

SUMMARY

The present disclosure features a strain-promoted [2+2+2] reaction that can be carried out under physiological conditions. In general, the reaction involves reacting a pi-electrophile with a low lying LUMO with a quadricyclane on a biomolecule, generating a covalently modified biomolecule. The selectivity of the reaction and its compatibility with aqueous environments provides for its application in vivo and in vitro. The reaction is compatible with modification of living cells. In certain embodiments, the pi-electrophile can comprise a molecule of interest that is desired for delivery to a quadricyclane-containing biomolecule via [2+2+2] reaction.

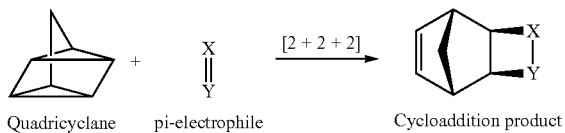

Quadricyclane    pi-electrophile    Cycloaddition product

DEFINITIONS

Figure 1:
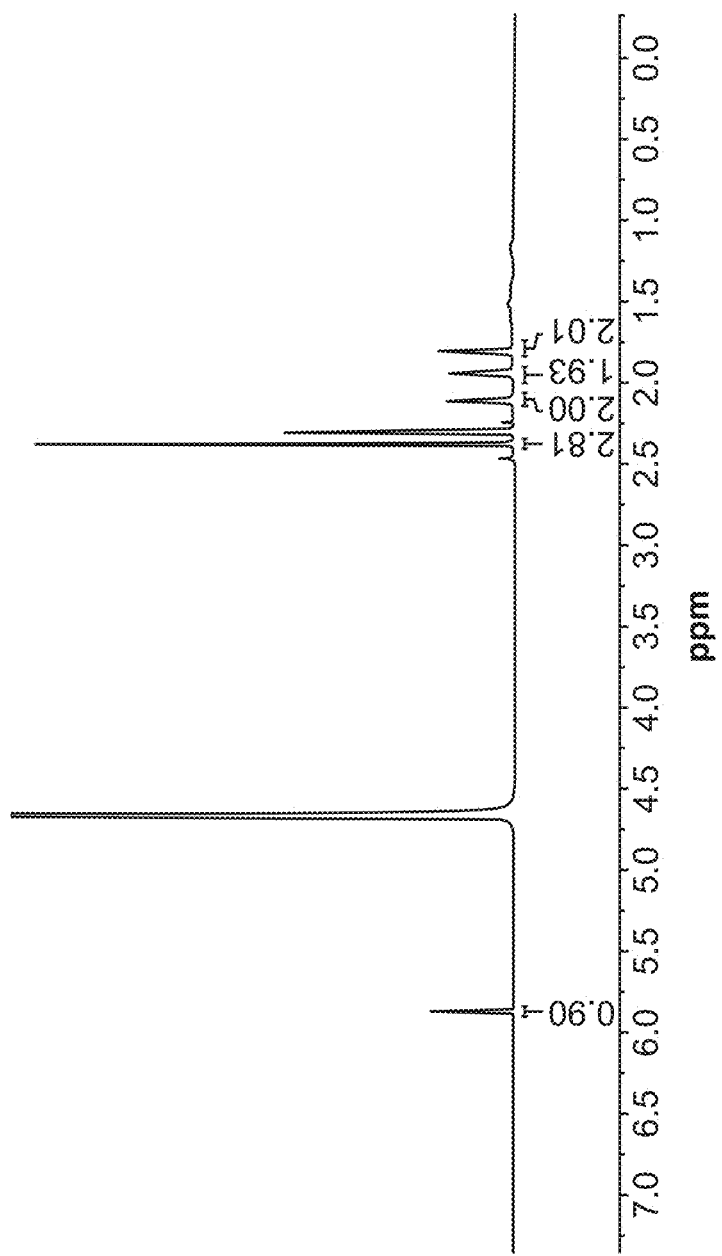
FIG. 1 is a spectrum that shows that quadricyclane is stable in phosphate buffered saline (PBS, pH 7.4). 7-acetoxy quadricyclane (1, 2 mg) was dissolved in 0.4 mL of $CD_3CN$. To this solution, 0.4 mL of deuterated PBS was added. The NMR spectrum above was taken 2.5 months after the described solution was prepared.

The following terms have the following meanings unless otherwise indicated. Any undefined terms have their art recognized meanings.

By "reaction partner" is meant a molecule or molecular moiety that specifically reacts with another reaction partner. Exemplary reaction partners are those of a subject reaction, i.e., a quadricyclane group of a quadricyclane-modified biomolecule and a pi-electrophile comprising a molecule of interest.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment or its synthetic environment and is at least 60% free, at least 75% free, at least 90% free, at least 95% free, at least 98% free, or at least 99% free from other components with which it is naturally associated, or is at least 60% free, at least 75% free, at least 90% free, at least 95% free, at least 98% free, or at least 99% free from contaminants associated with synthesis of the compound.

As used herein, the term "cell" in the context of in vivo and ex vivo applications is meant to encompass eukaryotic and prokaryotic cells of any genus or species, e.g., mammalian cells. "Cell" is also meant to encompass both normal cells and diseased cells, e.g., cancerous cells. In many embodiments, the cells are living cells.

The term "physiological conditions" is meant to encompass those conditions compatible with living cells, e.g., predominantly aqueous conditions of a temperature, pH, salinity, etc. that are compatible with living cells.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl (CH$_3$—), ethyl (CH$_3$CH$_2$—), n-propyl (CH$_3$CH$_2$CH$_2$—), isopropyl((CH$_3$)$_2$CH—), n-butyl (CH$_3$CH$_2$CH$_2$CH$_2$—), isobutyl ((CH$_3$)$_2$CHCH$_2$—), sec-butyl ((CH$_3$)(CH$_3$CH$_2$)CH—), t-butyl ((CH$_3$)$_3$C—), n-pentyl (CH$_3$CH$_2$CH$_2$CH$_2$CH$_2$—), and neopentyl ((CH$_3$)$_3$CCH$_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-β-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-5-alkyl, alkylene-S-substituted alkyl, substituted alkylene-5-alkyl and substituted alkylene-5-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$≡CCH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—

"Acylamino" refers to the groups —NR$^{20}$C(O)alkyl, —NR$^{20}$C(O)substituted alkyl, NR$^{20}$C(O)cycloalkyl, —NR$^{20}$C(O)substituted cycloalkyl, —NR$^{20}$C(O)cycloalkenyl, —NR$^{20}$C(O)substituted cycloalkenyl, —NR$^{20}$C(O)alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, NR$^{20}$C(O)heterocyclic, and —NR$^{20}$C(O)substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$C(O) NR$^{22}$R$^{23}$ where R$^{21}$, R$^{22}$, and R$^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic, provided that the point of attachment is through an atom of the aromatic aryl group. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen, and sulfur within the ring. Such heteroaryl groups can have a single ring (e.g., pyridinyl, imidazolyl or furyl) or multiple condensed rings (e.g., indolizinyl, quinolinyl, benzimidazolyl or benzothienyl), wherein the condensed rings may or may not be aromatic and/or contain a heteroatom, provided that the point of attachment is through an atom of the aromatic heteroaryl group. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 15 ring atoms, including 1 to 4 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$-moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cylcoalkyl, SO$_2$-cycloalkenyl, SO$_2$-substituted cylcoalkenyl, 5O$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cylcoalkyl, OSO$_2$-cycloalkenyl, OSO$_2$-substituted cylcoalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O$^-$)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80'}$s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means e.g. that one of the counter ions for such divalent alkali earth ions can be an ionized form of a subject compound and the other a typical counter ion such as chloride, or two ionized compounds of the present disclosure can serve as counter ions for such divalent alkali earth ions, or a doubly ionized subject compound can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the groups disclosed with respect to the individual terms herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —S$^{70}$, —$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —PO$_3^{-2}$(M$^+$)$_2$, —P(O)(OR$^{70}$)O$^-$M$^+$, —P(O)(OR$^{70}$)$_2$, —C(O)R$^{70}$, —C(S) R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(S)R$^{70}$, —OCO$_2^-$M$^+$, —OCO$_2$R$^{70}$, —OC(S) OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the disclosure herein, substituent groups for hydrogens on nitrogen atoms in "substituted" heteroalkyl and cycloheteroalkyl groups are, unless otherwise specified, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O) NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O) NR$^{80}$R$^{80}$, —NR$^{70}$C(NR$^{70}$)R$^{70}$ and —NR$^{70}$C(NR$^{70}$) NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (e.g., salts having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when the hydrogen of an acid is replaced by a cation, such as a metal cation or an organic cation and the like. Where applicable, the salt is a pharmaceutically acceptable salt, although this is not required for salts of compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N═C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

Detailed Description

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a quadricyclane" includes a plurality of such quadricyclanes and reference to "the biomolecule" includes reference to one or more biomolecules and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Representative Embodiments

The present disclosure features a strain-promoted [2+2+2] reaction that can be carried out under physiological conditions. In general, the reaction involves reacting a pi-electrophile with a low lying lowest unoccupied molecular orbital (LUMO) with a quadricyclane on a biomolecule, generating a covalently modified biomolecule. The selectivity of the reaction and its compatibility with aqueous environments provides for its application in vivo and in vitro. The reaction is compatible with modification of living cells. In certain embodiments, the pi-electrophile can comprise a molecule of interest that is desired for delivery to a quadricyclane-containing biomolecule (e.g., a biomolecule present in a living cell) via [2+2+2] reaction.

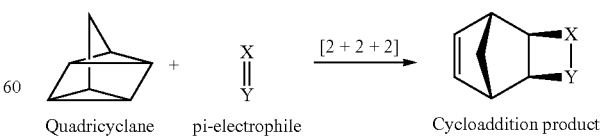

Quadricyclane    pi-electrophile      Cycloaddition product

The disclosure provides methods and compositions for specifically and efficiently synthetically modifying cellular components in an aqueous environment, thus providing for modification of such cellular components on or in living cells. The embodiments use reaction partners that are completely abiotic and are chemically orthogonal to native cellular components, thus providing for extreme selectivity of the reaction. Furthermore, the reaction can be carried out under physiological conditions, e.g., a pH of about 7 within an aqueous environment, and at about 37° C.

Quadricyclane possesses many qualities that render it a promising bioorthogonal reagent. First, it is abiotic, and quadricyclane's all sp$^3$-hybridized carbon system would be unreactive with native biomolecules. Second, the molecule is relatively small and can therefore be amenable to biosynthetic incorporation into biomolecules. Also, the structure of quadricyclane has about 80 kcal/mol of strain that promotes [2+2+2] cycloaddition with pi-systems with a low lying LUMO under mild conditions. The rates of these cycloaddition reactions are greatly enhanced by the "on water" effect, e.g., the reaction rate is enhanced in aqueous environments.

Quadricyclane reacts with a variety of electrophilic reagents. The high strain energy of quadricyclane activates the sigma bonds within this molecule for [2+2+2] cycloaddition with electrophilic reagents.

The reaction partners for the strain-promoted [2+2+2] reaction are discussed in more detail below. In the description, reference to formula with a Roman numeral, such as (I), is meant to include the formulae with the Roman numeral and letter, e.g. (Ia) and (Ib).

Pi-Electrophile Reaction Partner

As discussed above, quadricyclane reacts with a variety of electrophilic reagents. The ability of quadricyclane to react with electrophilic reagents can be attributed to the high strain energy of quadricyclane. In certain embodiments, the electrophilic reagent is a pi-electrophile with a low lying LUMO. An example of pi-electrophile with a low lying LUMO is an electron deficient pi-electrophile. Electron deficient pi-electrophile can be attributed to electronegative substituents. Certain pi-electrophile reaction partners (pi-electrophile compounds), including metal bis(dithiolene) compounds, azo compounds, alkynyl compounds, alkenyl compounds, and aryl compounds, are discussed below.

Metal Bis(Dithiolene) Compounds

The embodiments provide metal bis(dithiolene) compounds; and compositions comprising the compounds. A subject metal bis(dithiolene) compound is a compound of the formula:

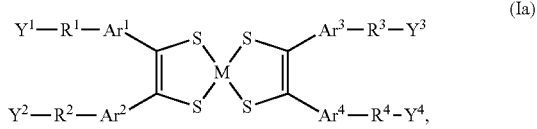
(Ia)

wherein
M is selected from one of the following: nickel (II), palladium (II), platinum (II), cobalt (I), iridium (I), rhodium (I), copper (II), copper (III), silver (III), gold (III), tungsten, and iron;
Ar$^1$, Ar$^2$, Ar$^3$, and Ar$^4$ are optional and are aryl, substituted aryl, heteroaryl, or substituted heteroaryl groups;
R$^1$, R$^2$, R$^3$, and R$^4$ are optional and are independently selected from hydrogen, alkylene, substituted alkylene, alkenylene, substituted alkenylene, alkynylene, substituted alkynylene, alkoxy, substituted alkoxy, aryl, substituted aryl, acyl, acylamino, aminoacyl, aminocarbonylamino, acyloxy, aminosulfonyl, sulfonylamino, amino, substituted amino, carboxyl ester, sulfonyl, sulfonyloxy, and thioalkoxy; and
Y$^1$, Y$^2$, Y$^3$, and Y$^4$ are independently selected from hydrogen; halogen; a moiety that comprises a reactive group that facilitates covalent attachment of a molecule of interest; and a molecule of interest;
wherein at least one of Y$^1$, Y$^2$, Y$^3$, and Y$^4$ is a moiety that comprises a reactive group that facilitates covalent attachment of a molecule of interest or a molecule of interest.

The embodiments provide metal bis(dithiolene) compounds; and compositions comprising the compounds. A subject metal bis(dithiolene) compound is a compound of the formula:

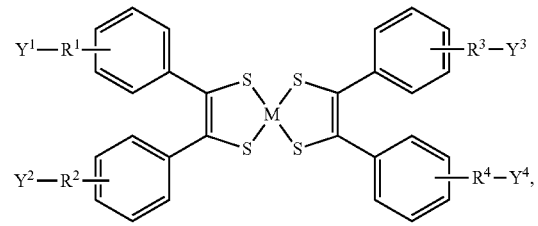

wherein
M is selected from one of the following: nickel (II), palladium (II), platinum (II), cobalt (I), iridium (I), rhodium (I), copper (II), copper (III), silver (III), gold (III), tungsten, and iron;
R$^1$, R$^2$, R$^3$, and R$^4$ are optional and are independently selected from hydrogen, alkylene, substituted alkylene, alkenylene, substituted alkenylene, alkynylene, substituted alkynylene, alkoxy, substituted alkoxy, aryl, substituted aryl, acyl, acylamino, aminoacyl, aminocarbonylamino, acyloxy, aminosulfonyl, sulfonylamino, amino, substituted amino, carboxyl ester, sulfonyl, sulfonyloxy, and thioalkoxy; and
Y$^1$, Y$^2$, Y$^3$ and Y$^4$ are independently selected from hydrogen; halogen; a moiety that comprises a reactive group that facilitates covalent attachment of a molecule of interest; and a molecule of interest;
wherein at least one of Y$^1$, Y$^2$, Y$^3$, and Y$^4$ is a moiety that comprises a reactive group that facilitates covalent attachment of a molecule of interest or a molecule of interest.

The embodiments provide metal bis(dithiolene) compounds; and compositions comprising the compounds. A subject metal bis(dithiolene) compound is a compound of the formula:

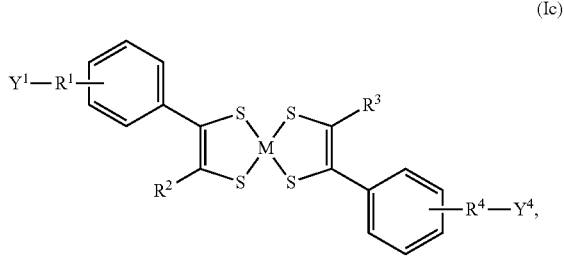
(Ic)

wherein

M is selected from one of the following: nickel (II), palladium (II), platinum (II), cobalt (I), iridium (I), rhodium (I), copper (II), copper (III), silver (III), gold (III), tungsten, and iron;

$R^2$ and $R^3$ are independently selected from the following: hydrogen, alkylene, substituted alkylene, alkenylene, substituted alkenylene, alkynylene, substituted alkynylene, alkoxy, substituted alkoxy, aryl, substituted aryl, acyl, acylamino, aminoacyl, aminocarbonylamino, acyloxy, aminosulfonyl, sulfonylamino, amino, substituted amino, carboxyl ester, sulfonyl, sulfonyloxy, and thioalkoxy;

$R^1$ and $R^4$ are optional and are independently selected from hydrogen, alkylene, substituted alkylene, alkenylene, substituted alkenylene, alkynylene, substituted alkynylene, alkoxy, substituted alkoxy, aryl, substituted aryl, acyl, acylamino, aminoacyl, aminocarbonylamino, acyloxy, aminosulfonyl, sulfonylamino, amino, substituted amino, carboxyl ester, sulfonyl, sulfonyloxy, and thioalkoxy; and $Y^1$ and $Y^4$ are independently selected from hydrogen; halogen; a moiety that comprises a reactive group that facilitates covalent attachment of a molecule of interest; and a molecule of interest;

wherein at least one of $Y^1$ and $Y^4$ is a moiety that comprises a reactive group that facilitates covalent attachment of a molecule of interest or a molecule of interest.

In formula (I), M is selected from one of the following: nickel (II), palladium (II), platinum (II), cobalt (I), iridium (I), rhodium (I), copper (II), copper (III), silver (III), gold (III), tungsten, and iron. In certain embodiments, M is selected from one of the following: nickel (II), palladium (II), and platinum (II). In certain embodiments, M is nickel (II). In certain embodiments, M is palladium (II). In certain embodiments, M is platinum (II). In certain embodiments, M is selected from one of the following: gold (III), tungsten, and iron. In certain embodiments, M is gold (III). In certain embodiments, M is tungsten. In certain embodiments, M is iron.

In formula (I), $Ar^1$, $Ar^2$, $Ar^3$, and $Ar^4$ are optional and are aryl, substituted aryl, heteroaryl, or substituted heteroaryl groups. In certain embodiments, $Ar^1$, $Ar^2$, $Ar^3$, or $Ar^4$ is aryl. In certain embodiments, $Ar^1$, $Ar^2$, $Ar^3$, or $Ar^4$ is substituted aryl. In certain embodiments, $Ar^1$, $Ar^2$, $Ar^3$, or $Ar^4$ is heteroaryl. In certain embodiments, $Ar^1$, $Ar^2$, $Ar^3$, or $Ar^4$ is substituted heteroaryl groups. In certain embodiments, the heteroaryl, or substituted heteroaryl groups comprise nitrogen, oxygen, or sulfur as heteroatoms.

In formula (I), $R^1$, $R^2$, $R^3$, and $R^4$ are optional and are independently selected from hydrogen, alkylene, substituted alkylene, alkenylene, substituted alkenylene, alkynylene, substituted alkynylene, alkoxy, substituted alkoxy, aryl, substituted aryl, acyl, acylamino, aminoacyl, aminocarbonylamino, acyloxy, aminosulfonyl, sulfonylamino, amino, substituted amino, carboxyl ester, sulfonyl, sulfonyloxy, and thioalkoxy.

In certain embodiments, $R^1$, $R^2$, $R^3$, or $R^4$ is hydrogen. In certain embodiments, $R^1$, $R^2$, $R^3$, or $R^4$ is alkylene, substituted alkylene, alkenylene, substituted alkenylene, alkynylene, or substituted alkynylene. In certain embodiments, $R^1$, $R^2$, $R^3$, or $R^4$ is alkoxy or substituted alkoxy. In certain embodiments, $R^1$, $R^2$, $R^3$, or $R^4$ is aryl or substituted aryl. In certain embodiments, $R^1$, $R^2$, $R^3$, or $R^4$ is carboxyl ester, acyl, acylamino, aminoacyl, aminocarbonylamino, or acyloxy. In certain embodiments, $R^1$, $R^2$, $R^3$, or $R^4$ is aminosulfonyl, sulfonylamino, sulfonyl, sulfonyloxy, or thioalkoxy. In certain embodiments, $R^1$, $R^2$, $R^3$, or $R^4$ is amino or substituted amino.

In formula (I), $Y^1$, $Y^2$, $Y^3$, and $Y^4$ are independently selected from hydrogen; halogen; a moiety that comprises a reactive group that facilitates covalent attachment of a molecule of interest; and a molecule of interest. In certain embodiments, $Y^1$, $Y^2$, $Y^3$, or $Y^3$, $Y^4$ is hydrogen. In certain embodiments, $Y^1$, $Y^2$, $Y^3$ or $Y^4$ is halogen. In certain embodiments, $Y^1$, $Y^2$, $Y^3$ or $Y^4$ is a moiety that comprises a reactive group that facilitates covalent attachment of a molecule of interest. In certain embodiments, $Y^1$, $Y^2$, $Y^3$, or $Y^4$ is a molecule of interest.

In certain embodiments, the pi-electrophile reactive partner is a metal bis(dithiolene) compound of the formula:

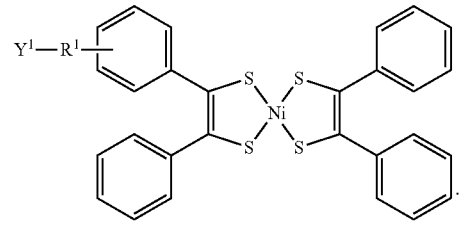

In certain embodiments, the pi-electrophile reactive partner is a metal bis(dithiolene) compound of the formula or salt thereof:

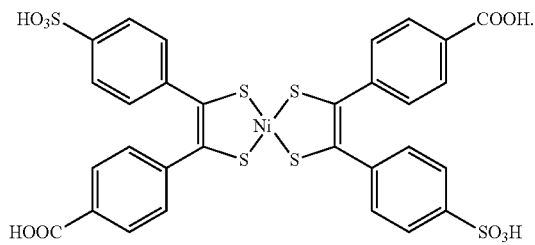

In certain embodiments, the pi-electrophile reactive partner is a metal bis(dithiolene) compound of the formula or salt thereof:

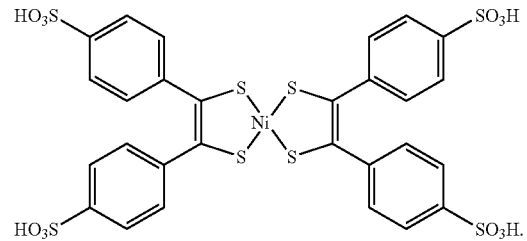

In certain embodiments, the pi-electrophile reactive partner is a metal bis(dithiolene) compound of the formula or salt thereof:

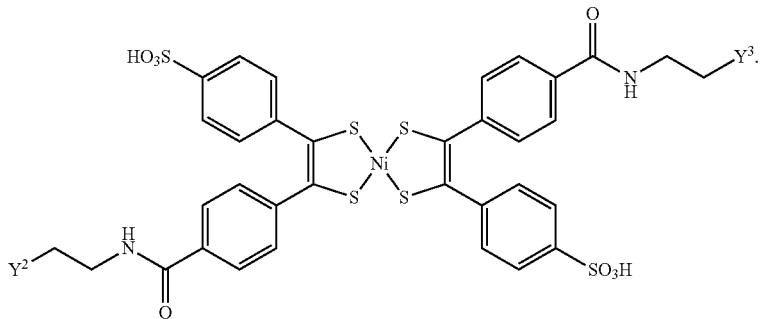

In certain embodiments, the pi-electrophile reactive partner is a metal bis(dithiolene) compound of the formula:

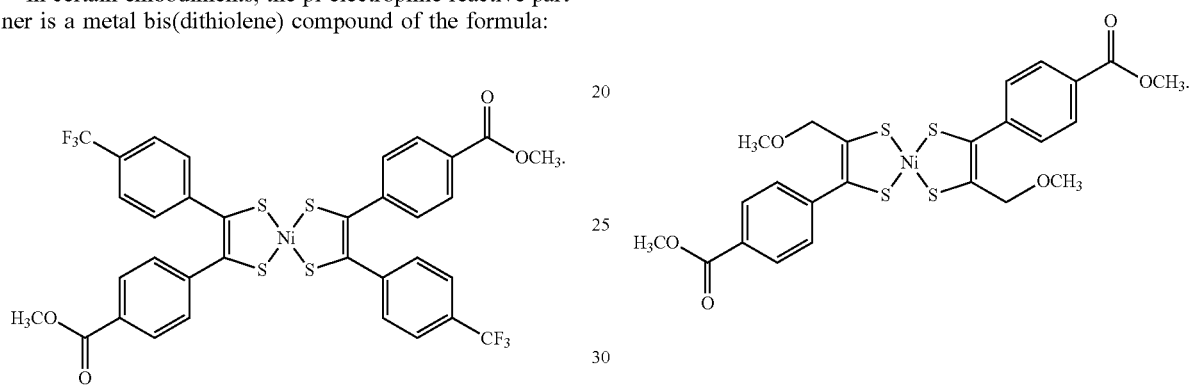

In certain embodiments, the pi-electrophile reactive partner is a metal bis(dithiolene) compound of the formula:

In certain embodiments, the pi-electrophile reactive partner is a metal bis(dithiolene) compound of the formula:

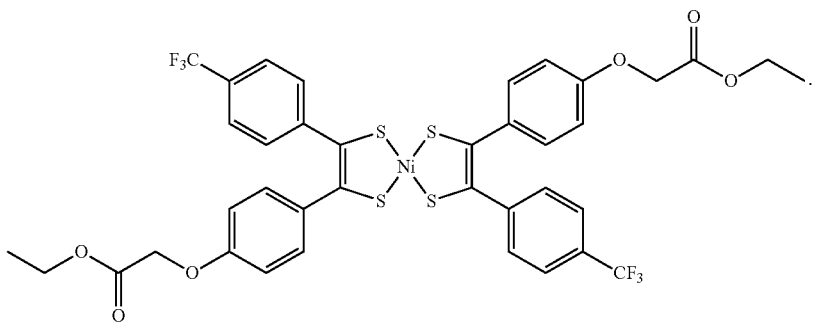

In certain embodiments, the pi-electrophile reactive partner is a metal bis(dithiolene) compound of the formula:

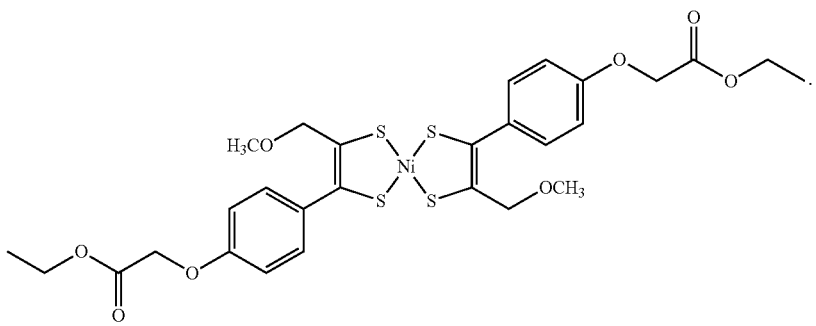

Azo Compounds

The embodiments provide azo compounds; and compositions comprising the compounds. A subject azo compound is a compound of the formula:

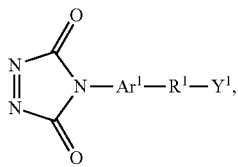

(IIa)

wherein
Ar¹ is an optional aryl or substituted aryl group;
R¹ is optional and is selected from alkylene, substituted alkylene, alkenylene, substituted alkenylene, alkynylene, substituted alkynylene, alkoxy, substituted alkoxy, aryl, substituted aryl, acyl, acylamino, aminoacyl, aminocarbonylamino, acyloxy, aminosulfonyl, sulfonylamino, amino, substituted amino, carboxyl ester, sulfonyl, sulfonyloxy, and thioalkoxy; and
Y¹ is selected from a moiety that comprises a reactive group that facilitates covalent attachment of a molecule of interest; and a molecule of interest.

The embodiments provide azo compounds; and compositions comprising the compounds. A subject azo compound is a compound of the formula:

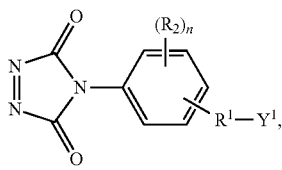

(IIb)

wherein
R¹ is optional and is selected from alkylene, substituted alkylene, alkenylene, substituted alkenylene, alkynylene, substituted alkynylene, alkoxy, substituted alkoxy, aryl, substituted aryl, acyl, acylamino, aminoacyl, aminocarbonylamino, acyloxy, aminosulfonyl, sulfonylamino, amino, substituted amino, carboxyl ester, sulfonyl, sulfonyloxy, and thioalkoxy;
Y¹ is selected from a moiety that comprises a reactive group that facilitates covalent attachment of a molecule of interest; and a molecule of interest;
R² is selected from alkyl, substituted alkyl, hydroxy, alkoxy, substituted alkoxy, amino, substituted amino, aminocarbonyl, carboxyl, carboxyl ester, cyano, halogen, nitro, alkenyl, substituted alkenyl, alkynyl, substituted alkynyl, and trihalomethyl; and
n is a number from zero to four.

In formula (II), Ar¹ is an optional aryl or substituted aryl group. In certain embodiments, Ar¹ is an aryl group. In certain embodiments, Ar¹ is a substituted aryl group.

In formula (II), R¹ is optional and is selected from alkylene, substituted alkylene, alkenylene, substituted alkenylene, alkynylene, substituted alkynylene, alkoxy, substituted alkoxy, aryl, substituted aryl, acyl, acylamino, aminoacyl, aminocarbonylamino, acyloxy, aminosulfonyl, sulfonylamino, amino, substituted amino, carboxyl ester, sulfonyl, sulfonyloxy, and thioalkoxy.

In certain embodiments, R¹ is alkylene, substituted alkylene, alkenylene, substituted alkenylene, alkynylene, or substituted alkynylene. In certain embodiments, R¹ is alkoxy or substituted alkoxy. In certain embodiments, R¹ is aryl or substituted aryl. In certain embodiments, R¹ is carboxyl ester, acyl, acylamino, aminoacyl, aminocarbonylamino, or acyloxy. In certain embodiments, R¹ is aminosulfonyl, sulfonylamino, sulfonyl, sulfonyloxy, or thioalkoxy. In certain embodiments, R¹ is amino or substituted amino.

In formula (II), Y¹ is selected from a moiety that comprises a reactive group that facilitates covalent attachment of a molecule of interest; and a molecule of interest. In certain embodiments, Y¹ is a moiety that comprises a reactive group that facilitates covalent attachment of a molecule of interest. In certain embodiments, Y¹ is a molecule of interest.

In formula (IIb), R² is selected from alkyl, substituted alkyl, hydroxy, alkoxy, substituted alkoxy, amino, substituted amino, aminocarbonyl, carboxyl, carboxyl ester, cyano, halogen, nitro, alkenyl, substituted alkenyl, alkynyl, substituted alkynyl, and trihalomethyl.

In certain embodiments, R² is alkyl, substituted alkyl, alkenyl, substituted alkenyl, alkynyl, substituted alkynyl, or trihalomethyl. In certain embodiments, R² is hydroxy, alkoxy, or substituted alkoxy. In certain embodiments, R² is amino or substituted amino. In certain embodiments, R² is aminocarbonyl, carboxyl, or carboxyl ester. In certain embodiments, R² is cyano, halogen, or nitro.

In certain embodiments, the pi-electrophile reactive partner is an azo compound of the formula:

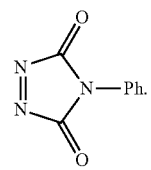

In certain embodiments, the pi-electrophile reactive partner is an azo compound of the formula:

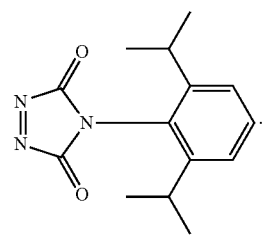

The embodiments provide azo compounds; and compositions comprising the compounds. A subject azo compound is a compound of the formula:

(III), wherein
R¹ and R² are optional and are independently selected from hydrogen, alkylene, substituted alkylene, alkenylene, substituted alkenylene, alkynylene, substituted alkynylene, alkoxy, substituted alkoxy, aryl, substituted aryl, acyl, acylamino, aminoacyl, aminocarbonylamino, acyloxy, aminosulfonyl, sulfonylamino, amino, substituted amino, carboxyl ester, sulfonyl, sulfonyloxy, and thioalkoxy; and $Y^1$ and $Y^2$ are independently selected from hydrogen; halogen; a moiety that comprises a reactive group that facilitates covalent attachment of a molecule of interest; and a molecule of interest;

wherein at least one of $Y^1$ and $Y^2$ is a moiety that comprises a reactive group that facilitates covalent attachment of a molecule of interest or a molecule of interest.

In formula (III), $R^1$ and $R^2$ are optional and is selected from alkylene, substituted alkylene, alkenylene, substituted alkenylene, alkynylene, substituted alkynylene, alkoxy, substituted alkoxy, aryl, substituted aryl, acyl, acylamino, aminoacyl, aminocarbonylamino, acyloxy, aminosulfonyl, sulfonylamino, amino, substituted amino, carboxyl ester, sulfonyl, sulfonyloxy, and thioalkoxy.

In certain embodiments, $R^1$ or $R^2$ is alkylene, substituted alkylene, alkenylene, substituted alkenylene, alkynylene, or substituted alkynylene. In certain embodiments, $R^1$ or $R^2$ is alkoxy or substituted alkoxy. In certain embodiments, $R^1$ or $R^2$ is aryl or substituted aryl. In certain embodiments, $R^1$ or $R^2$ is carboxyl ester, acyl, acylamino, aminoacyl, aminocarbonylamino, or acyloxy. In certain embodiments, $R^1$ or $R^2$ is aminosulfonyl, sulfonylamino, sulfonyl, sulfonyloxy, or thioalkoxy. In certain embodiments, $R^1$ or $R^2$ is amino or substituted amino.

In formula (III), $Y^1$ and $Y^2$ are independently selected from hydrogen; halogen; a moiety that comprises a reactive group that facilitates covalent attachment of a molecule of interest; and a molecule of interest. In certain embodiments, $Y^1$ or $Y^2$ is hydrogen. In certain embodiments, $Y^1$ or $Y^2$ is halogen. In certain embodiments, $Y^1$ or $Y^2$ is a moiety that comprises a reactive group that facilitates covalent attachment of a molecule of interest. In certain embodiments, $Y^1$ or $Y^2$ is a molecule of interest.

In certain embodiments, the pi-electrophile reactive partner is an azo compound of the formula:

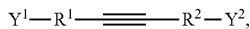

Alkynyl Compounds

The embodiments provide alkynyl compounds; and compositions comprising the compounds. A subject alkynyl compound is a compound of the formula:

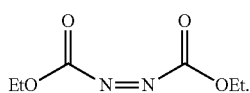
(IV)

wherein $R^1$ and $R^2$ are optional and are independently selected from hydrogen, alkylene, substituted alkylene, alkenylene, substituted alkenylene, alkynylene, substituted alkynylene, alkoxy, substituted alkoxy, aryl, substituted aryl, acyl, acylamino, aminoacyl, aminocarbonylamino, acyloxy, aminosulfonyl, sulfonylamino, amino, substituted amino, carboxyl ester, sulfonyl, sulfonyloxy, and thioalkoxy; and $Y^1$ and $Y^2$ are independently selected from hydrogen; halogen; a moiety that comprises a reactive group that facilitates covalent attachment of a molecule of interest; and a molecule of interest;

wherein at least one of $Y^1$ and $Y^2$ is a moiety that comprises a reactive group that facilitates covalent attachment of a molecule of interest or a molecule of interest.

In formula (IV), $R^1$ and $R^2$ are optional and is selected from alkylene, substituted alkylene, alkenylene, substituted alkenylene, alkynylene, substituted alkynylene, alkoxy, substituted alkoxy, aryl, substituted aryl, acyl, acylamino, aminoacyl, aminocarbonylamino, acyloxy, aminosulfonyl, sulfonylamino, amino, substituted amino, carboxyl ester, sulfonyl, sulfonyloxy, and thioalkoxy.

In certain embodiments, $R^1$ or $R^2$ is alkylene, substituted alkylene, alkenylene, substituted alkenylene, alkynylene, or substituted alkynylene. In certain embodiments, $R^1$ or $R^2$ is alkoxy or substituted alkoxy. In certain embodiments, $R^1$ or $R^2$ is aryl or substituted aryl. In certain embodiments, $R^1$ or $R^2$ is carboxyl ester, acyl, acylamino, aminoacyl, aminocarbonylamino, or acyloxy. In certain embodiments, $R^1$ or $R^2$ is aminosulfonyl, sulfonylamino, sulfonyl, sulfonyloxy, or thioalkoxy. In certain embodiments, $R^1$ or $R^2$ is amino or substituted amino.

In formula (IV), $Y^1$ and $Y^2$ are independently selected from hydrogen; halogen; a moiety that comprises a reactive group that facilitates covalent attachment of a molecule of interest; and a molecule of interest. In certain embodiments, $Y^1$ or $Y^2$ is hydrogen. In certain embodiments, $Y^1$ or $Y^2$ is halogen. In certain embodiments, $Y^1$ or $Y^2$ is a moiety that comprises a reactive group that facilitates covalent attachment of a molecule of interest. In certain embodiments, $Y^1$ or $Y^2$ is a molecule of interest.

In certain embodiments, the pi-electrophile reactive partner is an alkynyl compound of the formula:

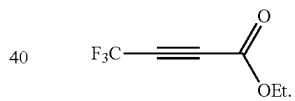

Alkenyl Compounds

The embodiments provide alkenyl compounds; and compositions comprising the compounds. A subject alkenyl compound is a compound of the formula:

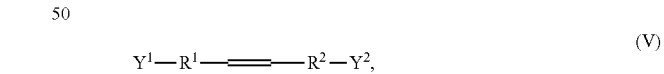
(V)

wherein $R^1$ and $R^2$ are optional and are independently selected from hydrogen, alkylene, substituted alkylene, alkenylene, substituted alkenylene, alkynylene, substituted alkynylene, alkoxy, substituted alkoxy, aryl, substituted aryl, acyl, acylamino, aminoacyl, aminocarbonylamino, acyloxy, aminosulfonyl, sulfonylamino, amino, substituted amino, carboxyl ester, sulfonyl, sulfonyloxy, and thioalkoxy; and $Y^1$ and $Y^2$ are independently selected from hydrogen; halogen; a moiety that comprises a reactive group that facilitates covalent attachment of a molecule of interest; and a molecule of interest;

wherein at least one of $Y^1$ and $Y^2$ is a moiety that comprises a reactive group that facilitates covalent attachment of a molecule of interest or a molecule of interest.

In formula (V), $R^1$ and $R^2$ are optional and is selected from alkylene, substituted alkylene, alkenylene, substituted alkenylene, alkynylene, substituted alkynylene, alkoxy, substituted alkoxy, aryl, substituted aryl, acyl, acylamino, aminoacyl, aminocarbonylamino, acyloxy, aminosulfonyl, sulfonylamino, amino, substituted amino, carboxyl ester, sulfonyl, sulfonyloxy, and thioalkoxy.

In certain embodiments, $R^1$ or $R^2$ is alkylene, substituted alkylene, alkenylene, substituted alkenylene, alkynylene, or substituted alkynylene. In certain embodiments, $R^1$ or $R^2$ is alkoxy or substituted alkoxy. In certain embodiments, $R^1$ or $R^2$ is aryl or substituted aryl. In certain embodiments, $R^1$ or $R^2$ is carboxyl ester, acyl, acylamino, aminoacyl, aminocarbonylamino, or acyloxy. In certain embodiments, $R^1$ or $R^2$ is aminosulfonyl, sulfonylamino, sulfonyl, sulfonyloxy, or thioalkoxy. In certain embodiments, $R^1$ or $R^2$ is amino or substituted amino.

In formula (V), $Y^1$ and $Y^2$ are independently selected from hydrogen; halogen; a moiety that comprises a reactive group that facilitates covalent attachment of a molecule of interest; and a molecule of interest. In certain embodiments, $Y^1$ or $Y^2$ is hydrogen. In certain embodiments, $Y^1$ or $Y^2$ is halogen. In certain embodiments, $Y^1$ or $Y^2$ is a moiety that comprises a reactive group that facilitates covalent attachment of a molecule of interest. In certain embodiments, $Y^1$ or $Y^2$ is a molecule of interest.

Ketone Compounds

The embodiments provide ketone compounds; and compositions comprising the compounds. A subject ketone compound is a compound of the formula:

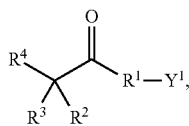

(VIa)

wherein $R^1$ is optional and is selected from alkylene, substituted alkylene, alkenylene, substituted alkenylene, alkynylene, substituted alkynylene, alkoxy, substituted alkoxy, aryl, substituted aryl, acyl, acylamino, aminoacyl, aminocarbonylamino, acyloxy, aminosulfonyl, sulfonylamino, amino, substituted amino, carboxyl ester, sulfonyl, sulfonyloxy, and thioalkoxy; and $R^2$, $R^3$, and $R^4$ are independently selected from hydrogen, alkyl, substituted alkyl, hydroxy, alkoxy, substituted alkoxy, amino, substituted amino, aminocarbonyl, carboxyl, carboxyl ester, cyano, halogen, alkenyl, substituted alkenyl, alkynyl, substituted alkynyl, trihalomethyl, aryl, and substituted aryl; and $Y^1$ is selected from a moiety that comprises a reactive group that facilitates covalent attachment of a molecule of interest; and a molecule of interest.

The embodiments provide ketone compounds; and compositions comprising the compounds. A subject ketone compound is a compound of the formula:

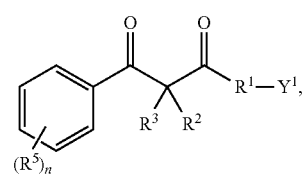

(VIb)

wherein $R^1$ is optional and is selected from alkylene, substituted alkylene, alkenylene, substituted alkenylene, alkynylene, substituted alkynylene, alkoxy, substituted alkoxy, aryl, substituted aryl, acyl, acylamino, aminoacyl, aminocarbonylamino, acyloxy, aminosulfonyl, sulfonylamino, amino, substituted amino, carboxyl ester, sulfonyl, sulfonyloxy, and thioalkoxy; and $R^2$ and $R^3$ are independently selected from hydrogen, alkyl, substituted alkyl, hydroxy, alkoxy, substituted alkoxy, amino, substituted amino, aminocarbonyl, carboxyl, carboxyl ester, cyano, halogen, alkenyl, substituted alkenyl, alkynyl, substituted alkynyl, and trihalomethyl;

each $R^5$ is independently selected from hydrogen, alkyl, substituted alkyl, hydroxy, alkoxy, substituted alkoxy, amino, substituted amino, aminocarbonyl, carboxyl, carboxyl ester, cyano, halogen, nitro, alkenyl, substituted alkenyl, alkynyl, substituted alkynyl, and trihalomethyl; and n is number from one to five;

$Y^1$ is selected from a moiety that comprises a reactive group that facilitates covalent attachment of a molecule of interest; and a molecule of interest.

In formula (VI), $R^1$ is optional and is selected from alkylene, substituted alkylene, alkenylene, substituted alkenylene, alkynylene, substituted alkynylene, alkoxy, substituted alkoxy, aryl, substituted aryl, acyl, acylamino, aminoacyl, aminocarbonylamino, acyloxy, aminosulfonyl, sulfonylamino, amino, substituted amino, carboxyl ester, sulfonyl, sulfonyloxy, and thioalkoxy.

In certain embodiments, $R^1$ is alkylene, substituted alkylene, alkenylene, substituted alkenylene, alkynylene, or substituted alkynylene. In certain embodiments, $R^1$ is alkoxy or substituted alkoxy. In certain embodiments, $R^1$ is aryl or substituted aryl. In certain embodiments, $R^1$ is carboxyl ester, acyl, acylamino, aminoacyl, aminocarbonylamino, or acyloxy. In certain embodiments, $R^1$ is aminosulfonyl, sulfonylamino, sulfonyl, sulfonyloxy, or thioalkoxy. In certain embodiments, $R^1$ is amino or substituted amino.

In formula (VI), $Y^1$ is selected from a moiety that comprises a reactive group that facilitates covalent attachment of a molecule of interest; and a molecule of interest. In certain embodiments, $Y^1$ is a moiety that comprises a reactive group that facilitates covalent attachment of a molecule of interest. In certain embodiments, $Y^1$ is a molecule of interest.

In formula (VIa), $R^2$, $R^3$, and $R^4$ are independently selected from hydrogen, alkyl, substituted alkyl, hydroxy, alkoxy, substituted alkoxy, amino, substituted amino, aminocarbonyl, carboxyl, carboxyl ester, cyano, halogen, alkenyl, substituted alkenyl, alkynyl, substituted alkynyl, trihalomethyl, aryl, and substituted aryl.

In certain embodiments, $R^2$, $R^3$, or $R^4$ is hydrogen, alkyl, substituted alkyl, alkenyl, substituted alkenyl, alkynyl, substituted alkynyl, or trihalomethyl. In certain embodiments, $R^2$, $R^3$, or $R^4$ is hydroxy, alkoxy, or substituted alkoxy. In certain embodiments, $R^2$, $R^3$, or $R^4$ is amino or substituted amino. In certain embodiments, $R^2$, $R^3$, or $R^4$ is aminocarbonyl, carboxyl, carboxyl ester, cyano, or halogen. In certain embodiments, $R^2$, $R^3$, or $R^4$ is aryl or substituted aryl.

In formula (VIb), each $R^5$ is independently selected from hydrogen, alkyl, substituted alkyl, hydroxy, alkoxy, substituted alkoxy, amino, substituted amino, aminocarbonyl, carboxyl, carboxyl ester, cyano, halogen, nitro, alkenyl, substituted alkenyl, alkynyl, substituted alkynyl, and trihalomethyl; and n is number from one to five.

In certain embodiments, $R^5$ is hydrogen, alkyl, or substituted alkyl. In certain embodiments, $R^5$ is hydroxy, alkoxy, or substituted alkoxy. In certain embodiments, $R^5$ is amino or substituted amino. In certain embodiments, $R^5$ is aminocarbonyl, carboxyl, or carboxyl ester. In certain embodiments, $R^5$ is cyano, halogen, or nitro. In certain embodiments, $R^5$ is alkenyl, substituted alkenyl, alkynyl, substituted alkynyl, or trihalomethyl.

In formula (VIb), n is number from one to five. In certain embodiments, n is one. In certain embodiments, n is two. In certain embodiments, n is three. In certain embodiments, n is four. In certain embodiments, n is five.

In certain embodiments, the pi-electrophile reactive partner is an alkynyl compound of the formula:

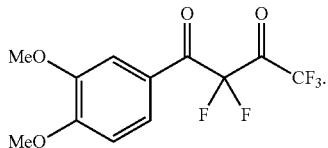 [SMILES: COc1ccc(C(=O)C(F)(F)C(=O)C(F)(F)F)cc1OC]

In certain embodiments, the pi-electrophile reactive partner is an alkynyl compound of the formula:

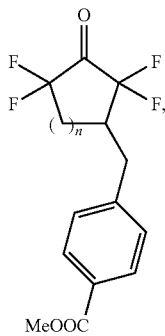

wherein n is a number form 1 to 4.

Reactive Group that Facilitates Covalent Attachment of a Molecule of Interest

In some embodiments, Y is a reactive group. Suitable reactive groups include, but are not necessarily limited to, carboxyl, amine, (e.g., alkyl amine (e.g., lower alkyl amine), aryl amine), ester (e.g., alkyl ester (e.g., lower alkyl ester, benzyl ester), aryl ester, substituted aryl ester), thioester, sulfonyl halide, alcohol, thiol, succinimidyl ester, isothiocyanate, iodoacetamide, maleimide, hydrazine, and the like. In some embodiments, Y is a reactive group selected from a carboxyl, an amine, an ester, a thioester, a sulfonyl halide, an alcohol, a thiol, a succinimidyl ester, an isothiocyanate, an iodoacetamide, a maleimide, and a hydrazine.

Other suitable reactive groups include, but are not necessarily limited to, aminooxy, aldehyde, ketone, nitrile oxide, nitrone, tetrazine, azirine, tetrazole, alkene, alkyne, cyclooctyne, trans-cyclooctene, norbornene, and azide.

Molecules of Interest

In some embodiments, Y is a molecule of interest. Suitable molecules of interest include, but are not limited to, a detectable label; a toxin (including cytotoxins); a peptide; a drug; a member of a specific binding pair; an epitope tag; and the like.

Where Y is a molecule of interest, the pi-electrophile comprises a molecule desired for delivery to a quadricyclane-containing biomolecule via [2+2+2] reaction. Molecules of interest that may be desirable for delivery include, but are not necessarily limited to, detectable labels (e.g., spin labels, fluorescence resonance energy transfer (FRET)-type dyes, e.g., for studying structure of biomolecules in vivo); small molecule drugs; cytotoxic molecules (e.g., drugs); ligands for binding by a target receptor (e.g., to facilitate viral attachment; attachment of a targeting protein present on a liposome, etc.); tags to aid in purification by, for example, affinity chromatography (e.g., attachment of a FLAG epitope); members of specific binding pairs (e.g., biotin, where the specific binding pair is biotin and avidin); molecules to facilitate selective attachment of the polypeptide to a surface; and the like. Specific, non-limiting examples are provided below.

Detectable Labels

The compositions and methods of the present disclosure can be used to deliver a detectable label to a quadricyclane-containing biomolecule. Thus, in some embodiments, a pi-electrophile comprises a detectable label, covalently bound to the pi-electrophile either directly or through a linker.

Exemplary detectable labels include, but are not necessarily limited to, fluorescent molecules (e.g., autofluorescent molecules, molecules that fluoresce upon contact with a reagent, etc.), radioactive labels (e.g., $^{111}$In, $^{125}$I, $^{131}$I, $^{212}$B, $^{90}$Y, $^{186}$Rh, and the like); a positron emission tomography (PET) imaging label (e.g. $^{18}$F); fluorescent tags; imaging reagents (e.g., those described in U.S. Pat. No. 4,741,900 and U.S. Pat. No. 5,326,856), and the like. Detectable labels also include peptides or polypeptides that can be detected by antibody binding, e.g., by binding of a detectably labeled antibody or by detection of bound antibody through a sandwich-type assay. Also suitable for use are quantum dots (e.g., detectably labeled semiconductor nanocrystals, such as fluorescently labeled quantum dots, antibody-conjugated quantum dots, and the like). See, e.g., Dubertret et al. 2002 Science 298:759-1762; Chan et al. (1998) Science 281: 2016-2018; U.S. Pat. No. 6,855,551; Bruchez et al. (1998) Science 281:2013-2016.

Suitable fluorescent molecules (fluorophores) include, but are not limited to, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethylrhodamine-, methyl ester), TMRE (tetramethylrhodamine, ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphth-alimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120),7-amino-4-trifluoromethylcoumarin (Coumarin 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin;
diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino)naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)amino-1-fluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N-tetramethyl-6-carboxyrhodamine (TAMRA); tetramethyl rhodamine; tetramethyl hodamine isothiocyanate (TRITC); riboflavin; 5-(2'-aminoethyl)aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes, a DDAO compound (e.g., 7-hydroxy-9H-(1,3-dichloro-9,9-dimethylacridin-2-one or 1,3-dichloro-9,9-dimethyl-9H-acridin-2(7)-one), cascade blue, and the like. Fluorophores of interest are further described in WO 01/42505 and WO 01/86001.

Suitable fluorescent proteins and chromogenic proteins include, but are not limited to, a green fluorescent protein (GFP), including, but not limited to, a GFP derived from *Aequoria victoria* or a derivative thereof, e.g., a "humanized" derivative such as Enhanced GFP, which is available commercially, e.g., from Clontech, Inc.; a GFP from another species such as *Renilla reniformis, Renilla mulleri*, or *Ptilosarcus guernyi*, as described in, e.g., WO 99/49019 and Peelle et al. (2001) *J. Protein Chem.* 20:507-519; "humanized" recombinant GFP (hrGFP) (Stratagene); any of a variety of fluorescent and colored proteins from Anthozoan species, as described in, e.g., Matz et al. (1999) *Nature Biotechnol.* 17:969-973; and the like.

Suitable epitope tags include, but are not limited to, hemagglutinin (HA; e.g., CYPYDVPDYA; SEQ ID NO:1), FLAG (e.g., DYKDDDDK; SEQ ID NO:2), FLAG-C (e.g., DYKDDDDKC; SEQ ID NO:3, c-myc (e.g., CEQKLISEEDL; SEQ ID NO:4), a metal ion affinity tag such as a polyhistidine tag (e.g., $His_6$), and the like.

Suitable imaging agents include positive contrast agents and negative contrast agents. Suitable positive contrast agents include, but are not limited to, gadolinium tetraazacyclododecanetetraacetic acid (Gd-DOTA); Gadolinium-diethylenetriaminepentaacetic acid (Gd-DTPA); Gadolinium-1,4,7-tris(carbonylmethyl)-10-(2'-hydroxypropyl)-1,4,7,10-tetraazacyclododecane (Gd-HP-DO3A); Manganese(II)-dipyridoxal diphosphate (Mn-DPDP); Gd-diethylenetriaminepentaacetate-bis(methylamide) (Gd-DTPA-BMA); and the like. Suitable negative contrast agents include, but are not limited to, a superparamagnetic iron oxide (SPIO) imaging agent; and a perfluorocarbon, where suitable perfluorocarbons include, but are not limited to, fluoroheptanes, fluorocycloheptanes, fluoromethylcycloheptanes, fluorohexanes, fluorocyclohexanes, fluoropentanes, fluorocyclopentanes, fluoromethylcyclopentanes, fluorodimethylcyclopentanes, fluoromethylcyclobutanes, fluorodimethylcyclobutanes, fluorotrimethylcyclobutanes, fluorobutanes, fluorocyclobutanse, fluoropropanes, fluoroethers, fluoropolyethers, fluorotriethylamines, perfluorohexanes, perfluoropentanes, perfluorobutanes, perfluoropropanes, sulfur hexafluoride, and the like.

Suitable imaging agents also include spin labels suitable for use in electron paramagnetic resonance (EPR) and dynamic nuclear polarization.

Specific Binding Partners

In another embodiment, a pi-electrophile comprises a member of a pair of binding partners. A member of a pair of binding partners is referred to herein as a "specific binding partner."

Suitable specific binding partners include, but are not limited to, a member of a receptor/ligand pair; a member of an antibody/antigen pair; a member of a lectin/carbohydrate pair; a member of an enzyme/substrate pair; biotin/avidin; biotin/streptavidin; digoxin/antidigoxin; and the like. Suitable specific binding partners include, but are not limited to a receptor ligand; a receptor for a ligand; a ligand-binding portion of a receptor; an antibody; an antigen-binding fragment of an antibody; an antigen; a hapten; a lectin; a lectin-binding carbohydrate; an enzyme substrate; an irreversible inhibitor of an enzyme (e.g., an irreversible inhibitor that binds a substrate binding site of an enzyme, e.g., a "suicide" substrate); and the like.

Suitable ligand members of receptor/ligand pairs include, but are not limited to, neurotransmitters such as opioid compounds, acetylcholine, and the like; viral proteins that bind to a cell surface receptor, e.g., human immunodeficiency virus gp120, and the like; hormones; and the like.

Suitable antigen-binding antibody fragments include $F(ab')_2$, $F(ab)_2$, Fab', Fab, Fv, scFv, and Fd fragments, single-chain antibodies, and fusion proteins comprising an antigen-binding portion of an antibody and a non-antibody protein (e.g., an antigen-binding fragment of an antibody fused to an immunoglobulin constant region).

Suitable haptens include, but are not limited to, (4-hydroxy-3-nitrophenyl)acetyl; diethylenetriaminepentaacetic acid (DTPA) or one of its metal complexes; paranitrophenyl; biotin; fluorescein isothiocyanate; and the like.

Drugs

Suitable drugs that can be attached to a pi-electrophile include, but are not limited to, cytotoxic compounds (e.g., cancer chemotherapeutic compounds); antiviral compounds; biological response modifiers (e.g., hormones, chemokines, cytokines, interleukins, etc.); microtubule affecting agents; hormone modulators; steroidal compounds; and the like.

Suitable cancer chemotherapeutic compounds include, but are not limited to, non-peptidic (i.e., non-proteinaceous) compounds that reduce proliferation of cancer cells; peptidic compounds that reduce proliferation of cancer cells; antimetabolite agents; cytotoxic agents; and cytostatic agents. Non-limiting examples of chemotherapeutic agents include alkylating agents, nitrosoureas, antimetabolites, antitumor antibiotics, plant (vinca) alkaloids, and steroid hormones.

Suitable agents that act to reduce cellular proliferation include, but are not limited to, alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Suitable antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable anti-proliferative natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; aziridinopyrrolo indolediones, e.g. mitomycin; macrocyclic immunosuppressants, e.g. cyclosporine, FK-506 (tacrolimus, prograf), rapamycin, etc.; and the like.

Other suitable anti-proliferative cytotoxic agents are navelbene, CPT-11, anastrazole, letrazole, capecitabine, reloxafine, cyclophosphamide, ifosamide, and droloxafine.

Suitable microtubule affecting agents that have antiproliferative activity include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Suitable hormone modulators and steroids (including synthetic analogs) include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation, therefore compounds that bind to the estrogen receptor are used to block this activity. Corticosteroids may inhibit T cell proliferation.

Other suitable chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

Taxanes are also suitable for attachment to a pi-electrophile. "Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Biological response modifiers that are suitable for attachment to a pi electrophile moiety include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) IFN-α; (7) IFN-γ (8) colony-stimulating factors; and (9) inhibitors of angiogenesis.

Compositions

The present disclosure further provides compositions, including pharmaceutical compositions, comprising a pi-electrophile comprising a molecule of interest. A subject composition generally comprises a pi-electrophile comprising a molecule of interest; and at least one additional compound. Suitable additional compounds include, but are not limited to: a salt, such as a magnesium salt, a sodium salt, etc., e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; and the like.

In some embodiments, a subject composition comprises a pi-electrophile comprising a molecule of interest; and a pharmaceutically acceptable excipient. A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Quadricyclane Reaction Partner

The present disclosure provides quadricyclane-modified biomolecules; and compositions comprising the quadricyclane-modified biomolecules. A subject quadricyclane-modified biomolecule is a compound of the formula:

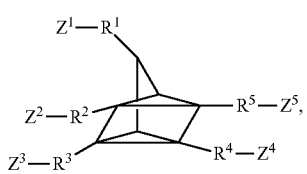

(I)

wherein $R^1$, $R^2$, $R^3$, $R^4$, and $R^5$ are optional linkers;

$Z^1$, $Z^2$, $Z^3$, $Z^4$, and $Z^5$ are independently selected from hydrogen and a biomolecule;

wherein at least one of $Z^1$, $Z^2$, $Z^3$, $Z^4$, and $Z^5$ is a biomolecule.

Exemplary biomolecules include, e.g., amino acids; peptides (e.g., having from about 2 to about 10 amino acids); monosaccharides; oligosaccharides; fatty acids; lipids; nucleotides; oligonucleotides; enzyme substrates; enzyme inhibitors; sterols; co-factors; Co-A derivatives; and the like.

Suitable linkers for $R^1$, $R^2$, and $R^3$ include, but are not limited to, alkylene, substituted alkylene, alkenylene, substituted alkenylene, alkynylene, substituted alkynylene, alkoxy, substituted alkoxy, aryl, substituted aryl, acyl, acylamino, aminoacyl, aminocarbonylamino, acyloxy, aminosulfonyl, sulfonylamino, amino, substituted amino, carboxyl ester, sulfonyl, sulfonyloxy, and thioalkoxy.

Biomolecules Attached to Quadricyclane

Exemplary biomolecules include, e.g., amino acids; peptides (e.g., having from about 2 to about 10 amino acids); monosaccharides; oligosaccharides; fatty acids; lipids; nucleotides; oligonucleotides; enzyme substrates; enzyme inhibitors; sterols; co-factors; Co-A derivatives; and the like. Thus, the present disclosure provides compounds comprising a biomolecule linked, directly or via a linker, to a quadricyclane moiety. Thus, e.g., the present disclosure provides peptide-quadricyclane conjugates, lipid-quadricyclane conjugates, sugar-quadricyclane conjugates, nucleotide-quadricyclane conjugates, etc.

The biomolecules can be naturally occurring, or may be synthetically or recombinantly produced, and may be isolated, substantially purified, or present within the native milieu of the unmodified molecule upon which the quadricyclane-containing biomolecule is based (e.g., on a cell surface or within a cell, including within a host animal, e.g., a mammalian animal, such as a murine host (e.g., rat, mouse), hamster, canine, feline, bovine, swine, and the like). In some embodiments, the biomolecule is present in vitro in a cell-free reaction. In other embodiments, the biomolecule is present in a cell and/or displayed on the surface of a cell. In many embodiments of interest, the biomolecule is in a living cell; on the surface of a living cell; in a living organism, e.g., in a living multicellular organism. Suitable living cells include cells that are part of a living multicellular organism; cells isolated from a multicellular organism; immortalized cell lines; and the like.

Where the biomolecule is a peptide or a polypeptide, the peptide or polypeptide may be composed of D-amino acids, L-amino acids, non-naturally-occurring amino acids (e.g., non-coded amino acids), or two or more of the foregoing, and may be further modified, either naturally, synthetically, or recombinantly, to include other moieties. For example, a polypeptide may be a lipoprotein, a glycoprotein, or other such modified protein.

In general, the biomolecule comprises at least one quadricyclane for reaction with pi-electrophile, but may comprise 2 or more, 3 or more, 5 or more, 10 or more quadricyclanes. The number of quadricyclanes that may be present in a biomolecule will vary according to the intended application of the final product of the reaction, the nature of the biomolecule itself, and other considerations which will be readily apparent to the ordinarily skilled artisan.

This embodiment is particularly useful in modification of a biomolecule in vivo. In this embodiment, the biomolecule is modified to comprise a quadricyclane at the point at which linkage to the pi-electrophile is desired. For example, where the biomolecule is a polypeptide, the polypeptide is modified to contain a quadricyclane at an N-terminus, at the C-terminus, or at an internal amino acid within the polypeptide. Where the biomolecule is a glycoprotein, a sugar residue of the glycoprotein can be modified to contain a quadricyclane.

Quadricyclane-Pi Electrophile Ligation Reaction

The present disclosure provides methods for chemoselective modification of a biomolecule comprising a quadricyclane. The methods generally involve reacting a quadracyclane in a quadricyclane-containing biomolecule with a pi-electrophile comprising a molecule of interest. Thus, after a [2+2+2] cycloaddition reaction of the quadricyclane and pi-electrophile, the molecule of interest is covalently bound to the biomolecule.

In many embodiments, a subject method for synthetically modifying a cellular component generally involves: introducing a quadricyclane moiety into a cellular component, thereby generating a quadricyclane-modified cellular component; and contacting the cell comprising the quadricyclane-modified cellular component with a reaction partner comprising a pi-electrophile comprising a molecule of interest, the contacting being under physiological conditions. The contacting step results in reaction between the quadricyclane group of quadricyclane-modified cellular component and the pi-electrophile of the reaction partner, thereby synthetically and covalently modifying the cellular component. In some embodiments, the method is carried out in a cell-free system in vitro. In some embodiments, the method is carried out on living cells in vitro. In other embodiments, the method is carried out on living cells ex vivo. In still other embodiments, the method is carried out on living cells in vivo.

In one embodiment, the chemoselective ligation is designed for use in fully aqueous, physiological conditions and involves production of a stable, final product comprising a fused quadracyclane/pi-electrophile. In general, this embodiment involves reacting a first reactant comprising a pi-electrophile comprising a molecule of interest with a second reactant comprising a quadricyclane-modified biomolecule, such that a covalent bond is formed between the first and second reactants by reaction of the pi-electrophile with the quadricyclane.

A subject ligation reaction can be carried out sequentially, or simultaneously, with other ligation reactions. For example, a subject quadricyclane-pi electrophile based ligation reaction can be carried out sequentially or simultaneously with a reaction based on a modified phosphine-azide ligation reaction. See, e.g., U.S. Pat. No. 6,570,040. As another example, a subject quadricyclane-pi electrophile based ligation reaction can be carried out sequentially or simultaneously with a reaction based on a modified cycloalkyne-azide ligation reaction. See, e.g., U.S. Pat. No. 7,808,619; and U.S. Patent Publication No. 2009/0068738. In some cases, a subject ligation reaction can be carried out substantially simultaneously with both a modified phosphine-azide ligation reaction and/or a modified cycloalkyne-azide ligation reaction. As an example, the pi-electrophile can comprise a first molecule of interest (e.g., a first Y group); the modified phosphine can comprise a second molecule of interest that is different from the first molecule of interest; and the modified cycloalkyne can comprise a third molecule of interest that is different from the first and the second molecule of interest. For example, the first, second, and third molecules of interest can be different detectable labels (e.g., different dyes; etc.).

In certain embodiments, a subject quadricyclane-pi electrophile based ligation reaction can be carried out sequentially or simultaneously with other reactions such as use of carbonyl chemistry (such as, but not limited to, condensation reaction between aldehydes and aminooxy compounds), Staudinger ligation (reaction of an azide with a phosphine or phosphite to produce an iminophosphorane), and cyclooctyne chemistry (such as cycloaddition of cyclooctyne with an azide; see, e.g., U.S. Patent Publication No. 2009-0068738-A1).

Utility

Subject pi-electrophiles comprising molecules of interest, and subject modification methods, are useful in a variety of applications, including research applications and diagnostic applications.

Bioorthogonal Chemistry

New additions to the bioorthogonal chemistry compendium can advance biological research by enabling multiplexed analysis of biomolecules in complex systems. The quadricyclane ligation can be used as a new bioorthogonal reaction. This reaction has a second-order rate constant of 0.25 $M^{-1}s^{-1}$, on par with fast bioorthogonal reactions of azides, and proceeds readily in aqueous environments. The quadricyclane ligation is compatible with, and orthogonal to, strain-promoted azide-alkyne cycloaddition and oxime ligation chemistries.

This quadricyclane-pi-electrophile is orthogonal to a current cohort. The published bioorthogonal transformations represent four broad reaction types: 1,3-dipolar cycloadditions, Diels-Alder reactions, metal-catalyzed couplings, and nucleophilic additions. Outside of this space lies the [2+2+2] cycloaddition reaction, a popular choice for the rapid assembly of functionalized ring systems. In practice, such reactions are typically metal catalyzed as a means to overcome an otherwise significant entropic barrier. However, the highly strained hydrocarbon quadricyclane directly undergoes [2+2+2] cycloaddition with specific types of π systems.

Research Applications

In some embodiments, the pi-electrophile compounds, and subject modification methods, are useful in research applications. Applications of interest include research applications, e.g., exploring functional and physical characteristics of a receptor; proteomics; metabolomics; and the like. Research applications also include drug discovery or other screening applications.

Proteomics aims to detect, identify, and quantify proteins to obtain biologically relevant information. Metabolomics is the detection, identification, and quantification of metabolites and other small molecules such as lipids and carbohydrates. Fiehn (2001) *Comparative and Functional Genomics* 2:155-168; and U.S. Pat. No. 6,873,914.

Drug discovery applications include, but are not limited to, identifying agents that inhibit cancer cell viability and/or growth. Thus, in some embodiments, the instant disclosure provides methods of identifying an agent that inhibits cancer cell viability and/or growth. The methods generally involve modifying a component of the cell to comprise a quadricyclane-modified biomolecule; contacting the cell, in the presence of a test agent, with a reaction partner comprising a pi-electrophile comprising a molecule of interest, the contacting being under physiological conditions; where the contacting results in reaction between the quadricyclane group and the pi-electrophile, thereby synthetically and covalently modifying the cellular component; and determining the effect, if any, of the test agent on the level of modification of the cell with the pi-electrophile comprising a molecule of interest.

Where the cancer cell is one that produces a higher amount of a carbohydrate than a normal (non-cancerous) cell of the same cell type, the method provides for identifying an agent that reduces growth and/or viability of the cancerous cell.

Diagnostic and Therapeutic Applications

Applications of interest also include diagnostic applications, e.g., for detection of cancer; and the like, where a pi-electrophile compound comprising a detectable label is used to label a quadricyclane-modified biomolecule, e.g., a quadricyclane-labeled biomolecule present on a cancer cell. Applications of interest also include therapeutic applications, where a drug or other therapeutic agent is delivered to a quadricyclane-modified biomolecule, using a pi electrophile compound that comprises a covalently linked drug or other therapeutic agent.

In some embodiments, a subject method is used for in vivo imaging, e.g., to determine the metabolic or other state of a cell in an organism, e.g., an individual. As one non-limiting example, a subject method can be applied to in vivo imaging of cancer cells in an individual (e.g., a mammal, including rodents, lagomorphs, felines, canines, equines, bovines, ovines, caprines, non-human primates, and humans).

One exemplary, non-limiting application of a subject quadracyclane-pi electophile cycloaddition is in the detection of metabolic change in cells that occur as they alter their phenotype. As one example, altered glycosylation patterns are a hallmark of the tumor phenotype, comprising under- and over-expression of naturally-occurring glycans as well as the presentation of glycans normally restricted to expression during embryonic development. Examples of common antigens associated with transformed cells are sialyl Lewis a, sialyl Lewis x, sialyl T, sialyl Tn, and polysialic acid (PSA). Jorgensen et al. (1995) Cancer Res. 55, 1817-1819; Sell (1990) Hum. Pathology 21, 1003-1019; Taki et al. (1988) J. Biochem. 103, 998-1003; Gabius (1988) Angew. Chem. Int. Ed. Engl. 27, 1267-1276; Feizi (1991) Trends Biochem. Sci. 16, 84-86; Taylor-Papadimitriou and Epenetos (1994) Trends Biotech. 12, 227-233; Hakomori and Zhang (1997) Chem. Biol. 4, 97-104; Dohi et al. (1994) Cancer 73, 1552. These antigens share an important feature—they each contain terminal sialic acid. PSA is a homopolymer of sialic acid residues up to 50 units in length. Elevated levels of sialic acid are highly correlated with the transformed phenotype in many cancers, including gastric (Dohi et al. (1994) Cancer 73, 1552; and Yamashita et al. (1995) J. Natl. Cancer Inst. 87, 441-446), colon (Yamashita et al. (1995) J. Natl. Cancer Inst. 87, 441-446; Hanski et al. (1995) Cancer Res. 55, 928-933; Hanski et al. (1993) Cancer Res. 53, 4082-4088; Yang et al. (1994) Glycobiology 4, 873-884; Saitoh et al. (1992) J. Biol. Chem. 267, 5700-5711), pancreatic (Sawada et al. (1994) Int. J. Cancer 57, 901-907), liver (Sawada et al. (1994) J. Biol. Chem. 269, 1425-1431), lung (Weibel et al. (1988) Cancer Res. 48, 4318-4323), prostate (Jørgensen et al. (1995) Cancer Res. 55, 1817-1819), kidney (Roth et al. (1988) Proc. Natl. Acad. Sci. USA 85, 2999-3000), and breast cancers (Cho et al. (1994) Cancer Res. 54, 6302-6305), as well as several types of leukemia (Joshi et al. (1987) Cancer Res. 47, 3551-3557; Altevogt et al. (1983) Cancer Res. 43, 5138-5144; Okada et al. (1994) Cancer 73, 1811-1816). A strong correlation between the level of cell surface sialic acid and metastatic potential has also been observed in several different tumor types (Kakeji et al. (1995) Brit. J. Cancer 71, 191-195; Takano et al. (1994) Glycobiology 4, 665-674). The collective display of multiple sialylated antigens on a single cancer cell can account for the fact that so many different tumor types share the high sialic acid phenotype without necessarily expressing an identical complement of antigens (Roth et al. (1988) supra). Consequently, diagnostic or therapeutic strategies that target cells on the basis of sialic acid levels have broad applicability to many cancers.

Introduction and incorporation of unnatural quadricyclane sugars (ManNQu, GalNQu) into living animals provides for detection of changes in metabolic state. Via the attachment of the appropriate epitope tag, the pi-electrophile compound labels these cells in a living organism, and consequently detects changes in metabolic state. Early detection of tumorigenic cells and subsequent intervention reduces the severity and increases survival rates for cancer patients.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Syntheses of Compounds

General Experimental Procedure

All chemical reagents were purchased from Sigma-Aldrich, Acros or TCI and used without purification unless noted otherwise. Anhydrous dimethylformamide (DMF) and methanol (MeOH) were purchased from Aldrich or Acros in sealed bottles; all other solvents were purified as described by Pangborn et al. (Pangborn, A. B.; Giardello, M. A.; Grubbs, R. H.; Rosen, R. K.; Timmers, F. J. *Organometallics* 1996, 15, 1518.) Solvent was removed by reduced pressure with a Buchi Rotovapor R-114 equipped with a Welch self-cleaning dry vacuum. Products were further dried by reduced pressure with an Edwards RV5 high vacuum. Lyophilization was performed on a LABCONCO FreeZone® instrument equipped with an Edwards RV2 pump. Thin layer chromatography was performed with EMD 60 Å silica gel plates. Flash chromatography was performed using Silicycle® 60 Å 230-400 mesh silica. All ¹H and ¹³C spectra are reported in ppm and referenced to solvent peaks. Spectra were obtained on Bruker AVQ-400, AVB-400, DRX-500, AV-500, or AV-600 instruments. UV/Vis/NIR spectra were acquired on a CARY 100 Bio UV-Visible Spectrophotometer with a range of 200-900 nm. Electron impact (EI) and electrospray ionization (ESI) mass spectra were obtained from the UC Berkeley Mass Spectrometry Facility. High performance liquid chromatography (HPLC) was performed on a Varian Pro Star or Varian Prep Star instrument with a C18 column.

Experimental Procedures

Scheme

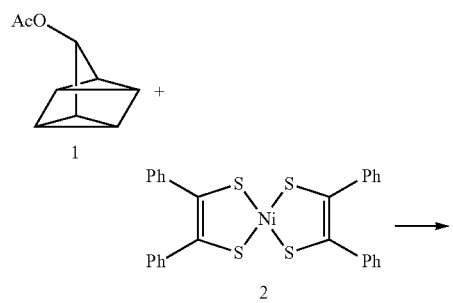

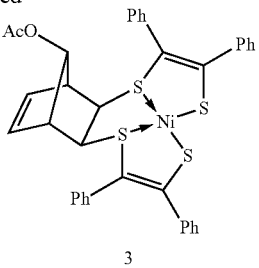

3

Complex 3. Bis(dithiobenzil)nickel(II) (2, 50 mg, 0.092 mmol, 1.0 equiv.) was combined with 7-acetoxy quadricyclane 1 (30 mg, 0.20 mmol, 2.2 equiv.) in dichloromethane (1 mL) for 5 days in the dark. The reaction was evaporated to ~200 mL and methanol (1 mL) was added. This mixture was placed in the fridge until brown precipitate formed. The precipitate was collected and washed with minimal amounts of methanol to yield 40 mg of 3 (0.058 mmol, 63%) Some product was left in the mother liquor. The crude ¹H nuclear magnetic resonance (NMR) showed ~90% conversion of 2 to 3. $R_f$=0.1 in 1:3 hexanes/dichloromethane. ¹H NMR (600 MHz, CDCl₃): δ 7.28-7.26 (m, 4H), 7.19-7.10 (m, 16H), 5.63 (s, 2H), 4.97 (s, 1H), 4.04 (s, 2H), 2.43 (apparent q, J=1.7 Hz, 2H), 1.97 (s, 3H). ¹³C NMR (125 MHz, CDCl₃): δ 170.8, 162.2, 140.1, 137.4, 133.0, 129.9, 129.1, 128.7, 128.4, 128.1, 127.5, 118.0, 85.4, 62.0, 53.6, 49.5, 21.1. HRMS (EI): calcd. for $C_{37}H_{20}O_2NiS_4^+$ [M]⁺, 692.0482; found, 692.0485.

Scheme

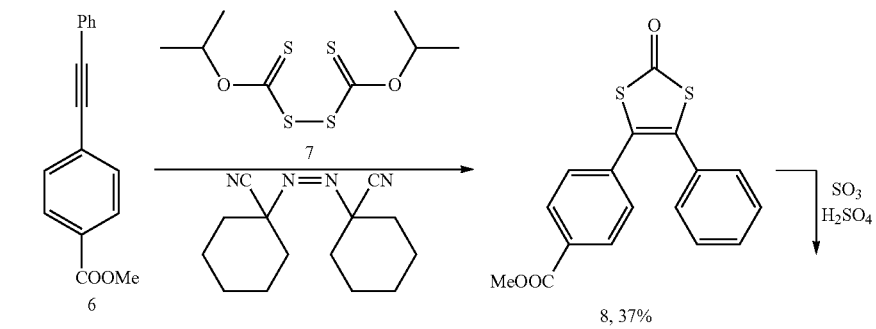

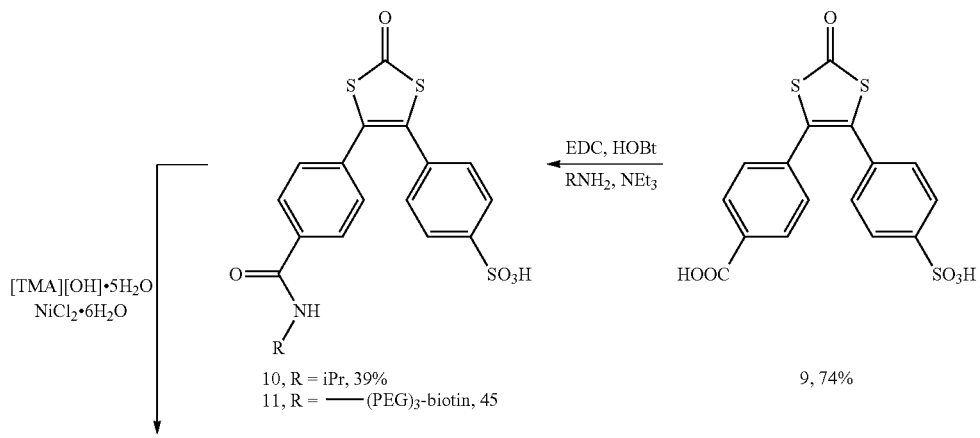

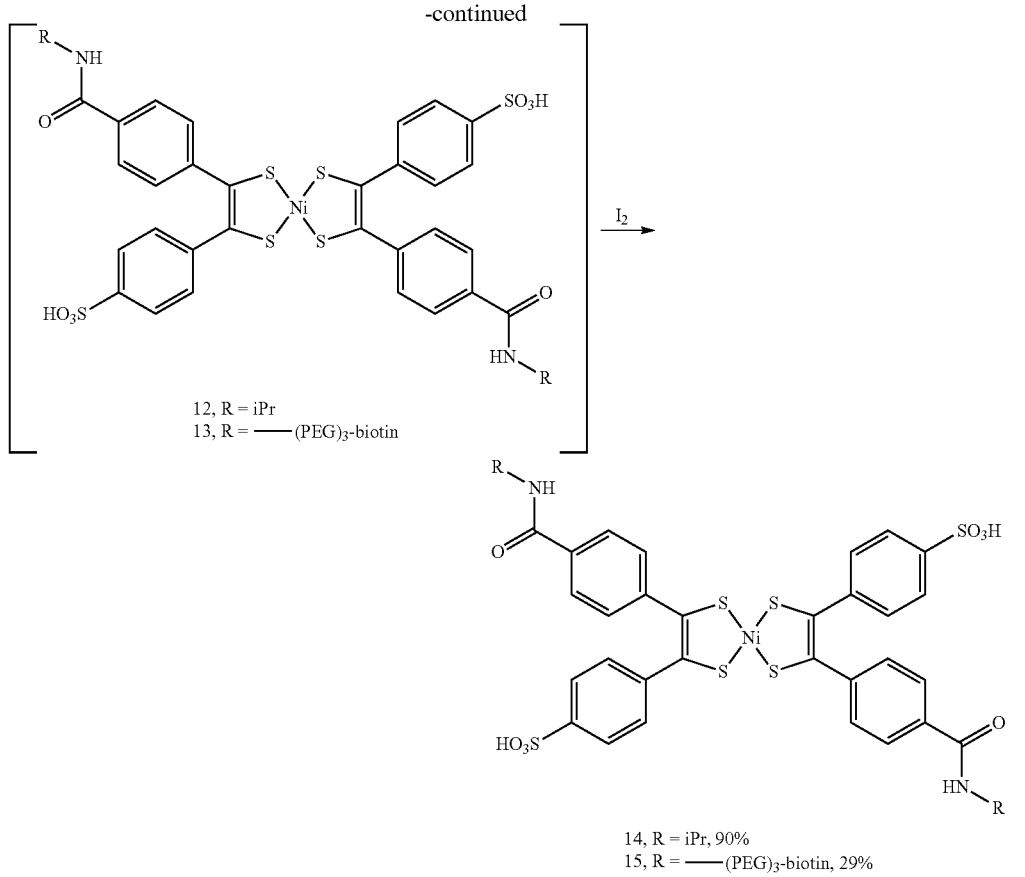

12, R = iPr
13, R = ―――(PEG)₃-biotin

14, R = iPr, 90%
15, R = ―――(PEG)₃-biotin, 29%

―――(PEG)₃-biotin =

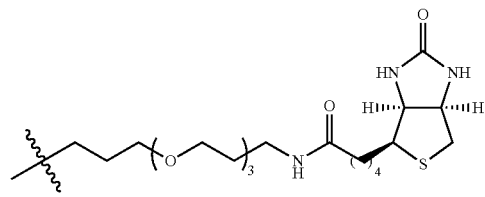

Methyl 4-(phenylethynyl)benzoate (6). Phenyl acetylene (1.5 mL, 14 mmol, 1.3 equiv.) and methyl-4-iodobenzoate (3.0 g, 11 mmol, 1.0 equiv.) were dissolved in tetrahydrofuran (THF) (90 mL, anhydrous). To this solution, CuI (300 mg, 1.5 mmol, 0.14 equiv.), PdCl$_2$(PPh$_3$)$_2$ (450 mg, 0.64 mmol, 0.06 equiv), and NEt$_3$ (6.0 mL, 43 mmol, 3.9 equiv.) were added. Upon NEt$_3$ addition, the reaction mixture turned dark black. The mixture was stirred at room temperature until the solution was no longer dark (~2 h), at which point the reaction was quenched with methanol (25 mL), evaporated to dryness, and purified by silica gel chromatography with hexanes/ethyl acetate (200:1, 100:1, 50:1, 25:1, 10:1, 8:1, 6:1). This procedure yielded pure 6 in 99% yield (2.7 g, 11 mmol). $R_f$=0.5 in 8:1 hexanes/ethyl acetate. $^1$H NMR (400 MHz, CDCl$_3$): δ 8.02 (d, J=8.1 Hz, 2H), 7.59 (d, J=8.4 Hz, 2H), 7.56-7.54 (m, 2H), 7.38-7.36 (m, 3H), 3.93 (s, 3H). $^{13}$C NMR (100 MHz, CDCl$_3$): δ 166.8, 131.9, 131.7, 129.7, 129.7, 129.0, 128.6, 128.2, 122.9, 92.6, 88.8, 52.4. HRMS (EI): calcd. for C$_{16}$H$_{12}$O$_2^+$ [M]$^+$, 236.0837; found, 236.0841.

Methyl 4-(2-oxo-5-phenyl-1,3-dithiol-4-yl)benzoate (8). Methyl 4-(phenylethynyl)benzoate 6 (250 mg, 1.1 mmol, 1.0 equiv.) was combined with diisopropyl xanthogen disulfide 7 (290 mg, 1.1 mmol, 1.0 equiv.) and 1,1'-azobis (cyclohexanecarbonitrile) (110 mg, 0.48 mmol, 0.45 equiv.) in m-xylene (2.2 mL, anhydrous). The mixture was heated to reflux for 20 h, at which point the reaction mixture was evaporated to dryness and 8 was purified by silica gel chromatography eluting with hexanes/ethyl acetate (40:1). This procedure resulted in 130 mg of 8 (0.40 mmol, 37%). $R_f$=0.5 in 6:1 hexanes/ethyl acetate. $^1$H NMR (600 MHz, CDCl$_3$): δ 7.91 (d, J=7.1 Hz, 2H), 7.31-7.30 (m, 1H), 7.29-7.26 (m, 4H), 7.20-7.19 (m, 2H), 3.90 (s, 3H). $^{13}$C NMR (150 MHz, CDCl$_3$): δ 190.2, 166.5, 136.5, 131.6, 131.0, 130.4, 130.2, 129.8, 129.7, 129.4, 129.2, 127.6, 52.5. HRMS (EI): calcd. for C$_{17}$H$_{12}$O$_3$S$_2^+$ [M]$^+$, 328.0228; found, 328.0222.

4-(2-oxo-5-(4-sulfophenyl)-1,3-dithiol-4-yl)benzoic acid (9). Compound 8 (700 mg, 2.1 mmol, 1.0 equiv.) was dissolved in sulfuric acid (8 mL, 18 M) and fuming sulfuric acid (80 μL, 20% in $H_2SO_4$) was added. This mixture was heated to 90° C. overnight. The following day it was cooled to room temperature, neutralized with NaOH and $NaHCO_3$ and evaporated. The resulting solid was subjected to methanol (~100 mL) and sonicated. This solution was then filtered and the filtrate was evaporated to dryness. The remaining solid was purified by silica gel chromatography with an acetonitrile/methanol solvent system (15:1, 10:1) to result in 620 mg of pure 9 (1.6 mmol, 74%). $R_f$=0.5 in 9:1 acetonitrile/water. $^1H$ NMR (600 MHz, MeOD): δ 7.93 (d, J=8.4 Hz, 2H), 7.76 (d, J=8.4 Hz, 2H), 7.35 (dd, J=13.9, 8.4 Hz, 4H). $^{13}C$ NMR (150 MHz, MeOD): δ 190.9, 169.2, 147.1, 137.1, 134.6, 132.9, 131.3, 130.9, 130.85, 130.4, 130.0, 127.8. HRMS (ESI): calcd. for $C_{16}H_9O_6S_3^-$ [M–H]$^-$ 392.9567; found 392.9565.

4-(5-(4-(isopropylcarbamoyl)phenyl)-2-oxo-1,3-dithiol-4-yl)benzenesulfonic acid (10). Compound 9 (130 mg, 0.33 mmol, 1.0 equiv.) was dissolved in dimethylformamide (5 mL, anhydrous). To this solution, isopropyl amine (30 μL, 0.037 mol, 1.1 equiv.), 1-ethyl-3-(3-dimethylaminopropyl) carbodiimide hydrochloride (EDC HCl, 96 mg, 0.50 mmol, 1.5 equiv.), hydroxybenzotriazole hydrate (HOBt, 65 mg, 0.42 mmol, 1.3 equiv.), and $NEt_3$ (90 μL, 0.65 mmol, 1.9 equiv.) were added. The mixture was stirred at room temperature for 5 h, at which point it was evaporated to dryness. Compound 10 was purified by HPLC using a water/methanol solvent system with a gradient of 30-95% methanol over 25 min. The desired product elutes at 14 min. This procedure resulted in pure 10 (56 mg, 0.13 mmol, 39%). $^1H$ NMR (600 MHz, MeOD): δ 7.75-7.72 (m, 4H), 7.34-7.31 (m, 4H), 4.17 (sep, J=6.6 Hz, 1H), 1.22 (d, J=6.6 Hz, 6H). $^{13}C$ NMR (150 MHz, MeOD): δ 191.0, 168.5, 147.3, 136.8, 135.8, 134.7, 131.0, 130.9, 130.3, 130.1, 129.1, 127.8, 43.4, 22.6. HRMS (ESI): calcd. for $C_{19}H_{16}O_5N_1S_3^-$ [M–H]$^-$ 434.0196; found, 434.0193.

Ni bis(dithiolene) 14. 4-(5-(4-(Isopropylcarbamoyl)phenyl)-2-oxo-1,3-dithiol-4-yl)benzenesulfonic acid 10 (45 mg, 0.10 mmol, 1.0 equiv.) was dissolved in a mixture of THF/MeOH (1 mL/0.7 mL). Tetramethyl ammonium hydroxide pentahydrate (40 mg, 0.22 mmol, 2.2 equiv.) was dissolved in MeOH (0.2 mL) and added to the solution with compound 10. The mixture turned a light orange color. After 30 min, $NiCl_26H_2O$ (12 mg, 0.050 mmol, 0.50 equiv.) was added and the mixture turned dark red. This mixture was stirred at room temperature overnight. The following morning, iodine (12 mg, 0.047 mmol, 0.051 equiv.) was added and the mixture became dark blue. After 2 h stirring at room temperature, the mixture was evaporated to dryness and purified by silica gel chromatography eluting with acetonitrile/water (25:1, 10:1, 5:1). This procedure resulted in 40 mg of 14 as a blue solid (0.046 mmol, 90%). $R_f$=0.2 in 9:1 acetonitrile/water. $^1H$ NMR (600 MHz, MeOD): δ 7.88 (d, J=6.4 Hz, 4H), 7.68 (d, J=7.8 Hz, 4H), 7.54 (d, J=7.1 Hz, 4H), 7.22 (s, 4H), 4.32-4.11 (m, 3H), 1.30 (d, J=6.5 Hz, 12H). The NMR was taken in the presence of $I_2$ to keep all of 14 in the neutral oxidation state. The anionic form is paramagnetic which prevents a spectrum form being obtained. Due to this difficulty we have characterized the sulfonated Ni bis(dithiolenes) by UV/Vis/NIR, HRMS, and HPLC instead of NMR. UV/Vis/NIR (water): 851 nm (1.2 au), 638 nm (0.4 au), 312 nm (3.1 au), 282 nm (3.3 au), 209 nm (5.1 au), 206 nm (4.7 au). HRMS (ESI): calcd. for $C_{36}H_{32}O_8N_2NiS_6^{-2}$ [M–2H]$^{-2}$, 434.9924; found, 434.9918.

Compound 11. 4-(2-Oxo-5-(4-sulfophenyl)-1,3-dithiol-4-yl)benzoic acid 9 (20 mg, 0.046 mmol, 1 equiv.) was dissolved in dimethylformamide (1 mL, anhydrous). To this solution, biotin-(PEG)$_3$-amine (23 mg, 0.056 mmol, 1.1 equiv.), 1-ethyl-3-(3-dimethylaminopropyl)carbodiimide hydrochloride (EDC HCl, 15 mg, 0.078 mmol, 1.7 equiv.), hydroxybenzotriazole (HOBt, 10 mg, 0.065 mmol, 1.4 equiv.), and $NEt_3$ (15 μL, 0.11 mmol, 2.0 equiv.) were added. The mixture was stirred at room temperature overnight. The following morning the mixture was evaporated to dryness and purified by HPLC using water/methanol solvent system. Compound 11 eluted at 32 min when a gradient of 0 to 100% methanol over 45 min was used. This procedure resulted in pure 11 (17 mg, 0.021 mol, 45%). $R_f$=0.4 in 4:1 acetonitrile/methanol. $^1H$ NMR (500 MHz, CDCl$_3$): δ 7.71 (d, J=7.9 Hz, 4H), 7.31 (t, J=7.6 Hz, 4H), 4.53-4.50 (m, 1H), 4.34-4.32 (m, 1H), 3.57-3.52 (m, 8H), 3.49-3.48 (m, 2H), 3.42 (dd, J=10.2, 5.9 Hz, 4H), 3.23-3.16 (m, 4H), 3.11-3.07 (m, 1H), 2.89 (dd, J=12.8, 4.8 Hz, 1H), 2.69 (d, J=12.8 Hz, 1H), 2.18 (t, J=7.3 Hz, 2H), 1.83-1.81 (m, 2H), 1.72-1.58 (m, 6H), 1.41-1.37 (m, 2H). $^{13}C$ NMR (125 MHz, CDCl$_3$): δ 190.8, 176.4, 167.0, 166.0, 147.3, 136.4, 135.9, 134.7, 131.1, 131.0, 130.3, 130.0, 129.1, 127.8, 71.6, 71.4, 71.3, 70.4, 70.0, 64, 62.4, 57.0, 50.0, 43.5, 41.0, 39.0, 38.2, 36.7, 30.4, 29.9, 29.5, 27.0. HRMS (ESI): cacld. For $C_{36}H_{45}O_{10}N_4S_4^-$ [M–H]$^-$, 821.2024; found, 821.2036.

Ni bis(dithiolene) 15. Ligand precursor 11 (17 mg, 0.021 mmol, 1.0 equiv.) was dissolved in a mixture of THF/MeOH (0.2 mL/0.2 mL). Tetramethyl ammonium hydroxide pentahydrate (8 mg, 0.044 mmol, 2.1 equiv.) was added to the solution with compound 11. The mixture turned a yellow color. After 30 min, $NiCl_26H_2O$ (2.5 mg, 0.011 mmol, 0.50 equiv.) was added and a brown precipitate formed. This mixture was stirred at room temperature overnight. The following morning, iodine (2.5 mg, 0.0098 mmol, 0.47 equiv.) was added and the mixture turned dark blue in color with most of the precipitate returning to solution. After 4 h stirring at room temperature, the mixture was evaporated to dryness and purified by silica gel chromatography eluting with acetonitrile/water (10:1, 5:1, 3:1, 2:1). This procedure resulted in 5 mg of 15 as a blue solid (0.0061 mmol, 29%). $R_f$=0.7 in 9:1 acetonitrile/water. UV/Vis/NIR (water): 868 nm (0.6 au), 349 nm (0.9 au), 315 nm (1.5 au), 276 nm (1.7 au), 201 nm (3.9 au). HRMS (ESI): calcd. for $C_{70}H_{90}O_{18}N_8NiS_8^{2-}$ [M–2H]$^{2-}$, 822.1752; found, 822.1749.

Scheme

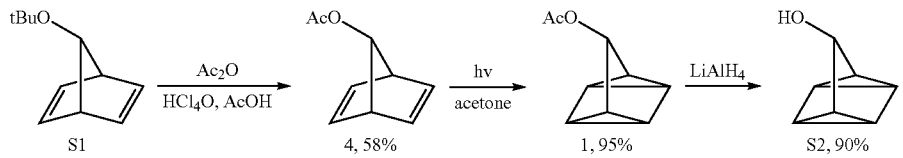

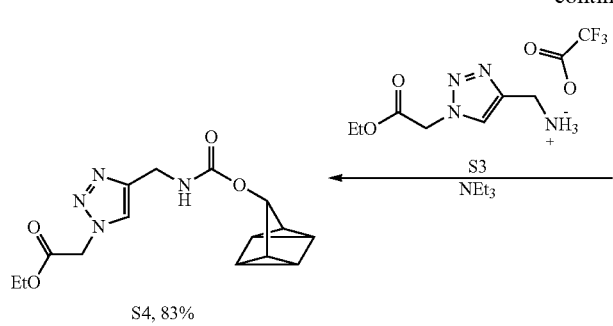
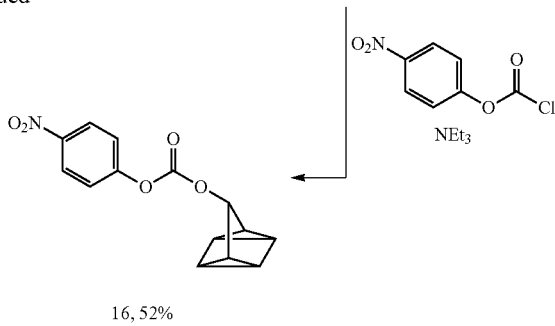

7-acetoxy-2,5-norbornadiene (4). 7-tert-Butoxy-2,5-norbornadiene S1 (1.7 g, 10 mmol, 1.0 equiv.) was combined with acetic anhydride (3.4 mL, 36 mmol, 3.6 equiv.) and acetic acid (16.9 mL) at 0° C. This solution was poured into precooled perchloric acid (2.3 mL, 60%). The yellow reaction mixture was stirred for 1 min at 0° C. and then poured onto ice water (~50 mL). Additional water was added until no yellow color remained. The aqueous solution was extracted with dichloromethane (3×50 mL). The organic layers were combined, dried, decanted, and evaporated to dryness. The crude product was purified by silica gel chromatography eluting with 25:1 hexanes/ether. This procedure resulted in 910 mg pure 4 as a colorless oil (6.1 mmol, 58%). $R_f$=0.5 in 10:1 hexanes/ethyl acetate. $^1$H NMR (600 MHz, CDCl$_3$): δ 6.63 (s, 2H), 6.50 (s, 2H), 4.50 (s, 1H), 3.53 (s, 2H), 1.89 (s, 3H). $^{13}$C NMR (100 MHz, CDCl$_3$): δ 171.2, 140.4, 137.9, 99.4, 52.5, 21.3. HRMS (EI): calcd. for $C_9H_{10}O_2^+$ [M]$^+$, 150.0681; found, 150.0638.

7-acetoxy quadricyclane (1). 7-Acetoxy-2,5-norbornadiene 4 (400 μL, 3.9 mmol, 1.0 equiv.) was dissolved in hexane (150 mL, degassed) and placed in a quartz round bottom flask containing a small amount of acetone (~0.5 mL). The mixture was irradiated with a 450 W Mercury Arc lamp for 5 h. Throughout the irradiation process, the reaction was kept under a nitrogen atmosphere. Following irradiation, sat AgNO$_3$ (5 mL) was added and the mixture was vigorously stirred in the dark for 15 min to complex any remaining 4. The hexane was removed and the aqueous solution was filtered and extracted with hexanes (2×10 mL). The hexanes were combined, dried, decanted, and evaporated to dryness to result in pure 5 as a wet, colorless solid (560 mg, 3.7 mmol, 95%). $R_f$=0.7 in 5:1 hexanes/ethyl acetate. $^1$H NMR (400 MHz, CDCl$_3$): δ 5.62 (t, J=1.7 Hz, 1H), 2.11 (s, 3H), 1.83-1.80 (m, 2H), 1.62-1.59 (m, 2H), 1.53-1.51 (m, 2H). $^{13}$C NMR (125 MHz, CDCl$_3$): δ 171.9, 82.4, 25.8, 21.5, 16.1, 14.8. HRMS (EI): calcd. for $C_9H_{10}O_2^+$ [M]$^+$, 150.0681; found, 150.0638.

7-hydroxy quadricyclane (S2). 7-Acetoxy quadricyclane 1 (325 mg, 2.2 mmol, 1.0 equiv.) was dissolved ether (1.0 mL, anhydrous). This solution was added to lithium aluminum hydride (1.2 mL, 1.2 mmol, 0.55 equiv., 1 M in diethyl ether) precooled to 0° C. The mixture was warmed to room temperature and stirred for 15 min, at which point the reaction was quenched with aqueous Rochelle's salt (~5 mL). The mixture was stirred until the aluminum was sufficiently complexed and two layers formed in the flask. The aqueous layer was extracted with ether (3×20 mL) and the organic layers were combined, dried with MgSO$_4$, filtered, and evaporated to dryness. This procedure resulted in ~90% pure S2 as a volatile, colorless oil (210 mg, 1.8 mmol, 80% yield). Note: If this compound is purified by silica gel chromatography and aldehyde byproduct is formed resulting in a less pure product than that obtained from the crude reaction. $R_f$=0.2 in 5:1 hexanes/ethyl acetate. $^1$H NMR (400 MHz, CDCl$_3$): δ 4.87 (t, J=1.8 Hz, 1H), 1.77-1.74 (m, 2H), 1.56-1.53 (m, 2H), 1.38-1.36 (m, 2H). $^{13}$C NMR (125 MHz, CDCl$_3$): δ 79.5, 29.0, 15.9, 14.9 HRMS (EI): calcd. for $C_7H_8O^+$ [M]$^+$, 108.0575; found, 108.0574.

p-Nitrophenyl Carbonate Quadricyclane 16. 7-Hydroxy quadricyclane S2 (20 mg, 0.19 mmol, 1.0 equiv.) was dissolved in dichloromethane (7 mL, anhydrous) and cooled to 0° C. Pyridine (90 μL, 1.1 mmol, 5.8 equiv., anhydrous) was added followed by p-nitrophenyl chloroformate (87 mg, 0.44 mmol, 2.3 equiv.). The reaction mixture was warmed to room temperature over 3 h, at which point it was quenched with water and extracted with dichloromethane (3×15 mL). The organic layers were combined, dried with MgSO$_4$, decanted, and evaporated to dryness. The crude product was purified by silica gel chromatography with hexanes/ether (9:1, 4:1, 2:1). This procedure resulted in 27 mg of pure 16 as a white solid (0.010 mmol, 52%). $R_f$=0.7 in 7:1 hexanes/ethyl acetate. $^1$H NMR (600 MHz, CDCl$_3$): δ 8.28 (d, J=9.0 Hz, 2H), 7.43 (d, J=9.0 Hz, 2H), 5.71 (s, 1H), 1.93-1.91 (m, 2H), 1.70-1.68 (m, 2H), 1.65-1.64 (m, 2H). $^{13}$C NMR (150 MHz, CDCl$_3$): δ 155.9, 152.9, 145.5, 125.5, 122.0, 88.0, 25.8, 16.4, 15.3. HRMS (EI): calcd. for $C_{14}H_{11}O_5N^+$ [M]$^+$, 273.0637; found, 273.0634.

Quadricyclane S4. Triazole S3 (45 mg, 0.15 mmol, 1.5 equiv.) and diisopropylethylamine (DIPEA) (165 μL, 0.95 mmol, 10 equiv.) were combined in dichloromethane (2 mL, anhydrous) and cooled to 0° C. p-Nitrophenyl carbonate quadricyclane 16 (27 mg, 0.099 mmol, was dissolved in dichloromethane (1 mL, anhydrous) and added to the solution containing triazole S3. The reaction mixture was warmed to room temperature overnight. The following morning, the mixture was evaporated to dryness and purified by silica gel chromatography to yield S4 (26 mg, 0.082 mmol, 83%). $R_f$=0.1 in 1:1 hexanes/ethyl acetate. $^1$H NMR (400 MHz, CDCl$_3$): δ 7.69 (s, 1H), 5.60 (s, 1H), 5.39 (bs, 1H), 5.13 (s, 2H), 4.50 (d, J=6.3 Hz, 2H), 4.26 (q, J=7.1 Hz, 2H), 1.79-1.77 (m, 2H), 1.58 (bs, 2H), 1.49 (bs, 2H), 1.29 (t, J=7.1 Hz, 3H). $^{13}$C NMR (100 MHz, CDCl$_3$): δ 166.4, 157.1, 145.8, 123.7, 83.1, 62.7, 51.1, 36.6, 26.0, 16.1, 14.8, 14.3. HRMS (ESI): calcd. for $C_{15}H_{19}O_4N_4$ [M+H]$^+$, 319.1401; found, 319.1404.

Scheme

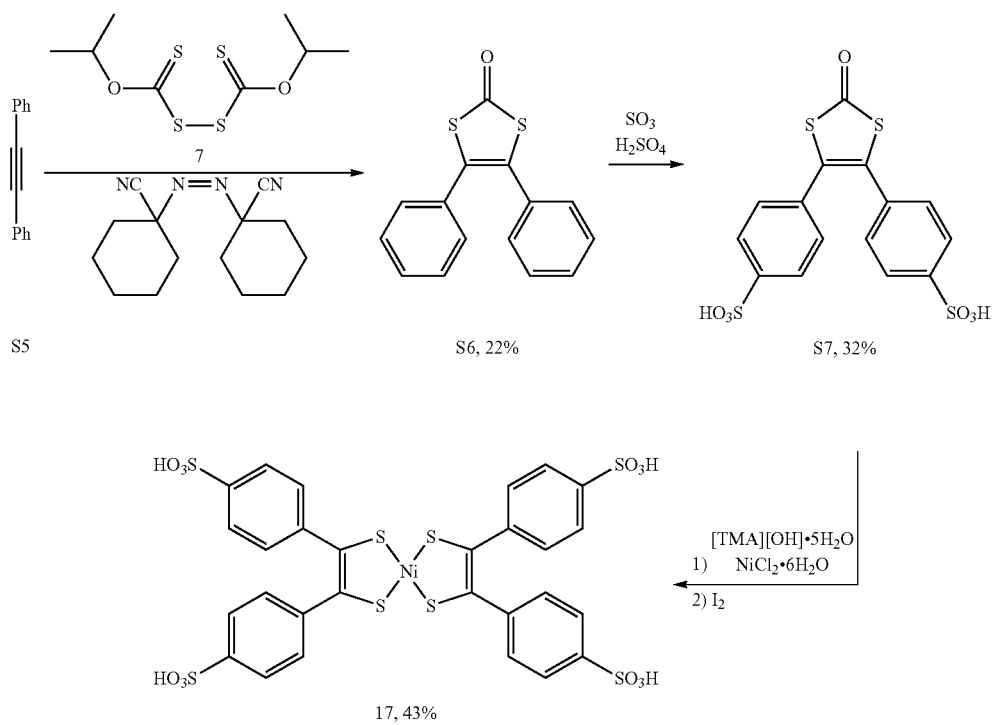

4,5-diphenyl-1,3-dithiol-2-one (S6). Diphenylacetylene S3 (2.5 g, 13.9 mmol, 1.0 equiv.) was combined with 1,1'-azobis(cyclohexane)carbonitrile (1.5 g, 6.1 mmol, 0.44 equiv.), diisopropyl xanthogen disulfide 7 (4.3 g, 15.9 mmol, 1.1 equiv.) in m-xylene (30 mL, anhydrous). The reaction mixture was heated to reflux overnight. The following day, the reaction mixture was cooled to room temperature, evaporated to dryness, and purified by silica gel chromatography with a hexane/toluene solvent system (10:1, 8:1, 6:1). This procedure resulted in 830 mg of S6 (3.1 mmol, 22% yield). $R_f$=0.6 in 10:1 hexanes/ethyl acetate. $^1$H NMR (400 MHz, CDCl$_3$): δ 7.35-7.25 (m, 10H). $^{13}$C NMR (100 MHz, CDCl$_3$): δ 190.7, 131.8, 129.6, 128.93, 128.89, 128.8. HRMS (EI): calcd. for $C_{15}H_{10}OS_2^+$ [M]$^+$, 270.0173; found, 270.0179.

4,4'-(2-oxo-1,3-dithiole-4,5-diyl)dibenzenesulfonic acid (S7). 4,5-diphenyl-1,3-dithiol-2-one S6 (830 mg, 3.1 mmol, 1.0 equiv.) was dissolved in sulfuric acid (10 mL, 18 M). Fuming sulfuric acid (150 µL, 20% in sulfuric acid) was added and the reaction mixture was heated to 90° C. overnight. The following morning the mixture was cooled to 0° C. and neutralized first with NaOH then with NaHCO$_3$. Once neutral, methanol (100 mL) was added, the solution was filtered, and the filtrate evaporated to dryness. The solid was again dissolved in methanol (100 mL), filtered, and the filtrate evaporated to dryness. The residue was then dissolved in water (50 mL) and washed with hexane (3×50 mL). The water layer was evaporated to dryness and the crude product was purified by HPLC on a C18 column with a water/acetonitrile solvent system (0 to 30% acetonitrile over 30 min). The product elutes at 10 min. This procedure resulted in 430 mg of pure S7 (1.0 mmol, 32% yield). $^1$H NMR (600 MHz, MeOD): δ 7.76 (d, J=8.3 Hz, 4H), 7.33 (d, J=8.4 Hz, 4H). $^{13}$C NMR (151 MHz, MeOD): δ 191.0, 147.1, 134.6, 130.8, 130.1, 127.8. HRMS (ESI): calcd. for $C_{15}H_9O_7S_4$ [M−H] 428.9237; found, 428.9238.

Ni bis(dithiolene) 17. 4,4'-(2-oxo-1,3-dithiole-4,5-diyl) dibenzenesulfonic acid S7 (33 mg, 0.075 mmol, 1.0 equiv.) was dissolved in a mixture of methanol (0.5 mL), THF (0.7 mL), and water (0.75 mL). Tetramethyl ammonium hydroxide pentahydrate (28 mg, 0.15 mmol, 2.1 equiv.) was dissolved in MeOH (0.15 mL) and added to the solution with compound S7. The mixture turned a yellow color. After 30 min, NiCl$_2$6H$_2$O (8.5 mg, 0.036 mmol, 0.48 equiv.) was added and stirred for 6 h, at which point iodine (8.5 mg, 0.033 mmol, 0.45 equiv.) was added and the blue mixture was stirred overnight at room temperature. The following morning, TLC indicated that some reduced complex may be present and more iodine (5 mg, 0.020 mmol, 0.26 equiv.) was added. After stirring for an additional 30 min, the reaction was evaporated to dryness and purified by silica gel chromatography eluting with acetonitrile/water (25:1, 9:1). This procedure resulted in 28 mg of 17 (0.033 mmol, 43% yield). UV/Vis/NIR: 832 nm (1.1 au), 591 nm (0.3 au), 349 nm (1.0 au), 315 nm (2.0 au), 272 nm (1.7 au). HRMS (ESI): calcd. for $C_{28}H_{16}O_{12}NiS_8^{4-}$ [M−4H]$^{4-}$, 214.4446; found, 214.4447.

Scheme

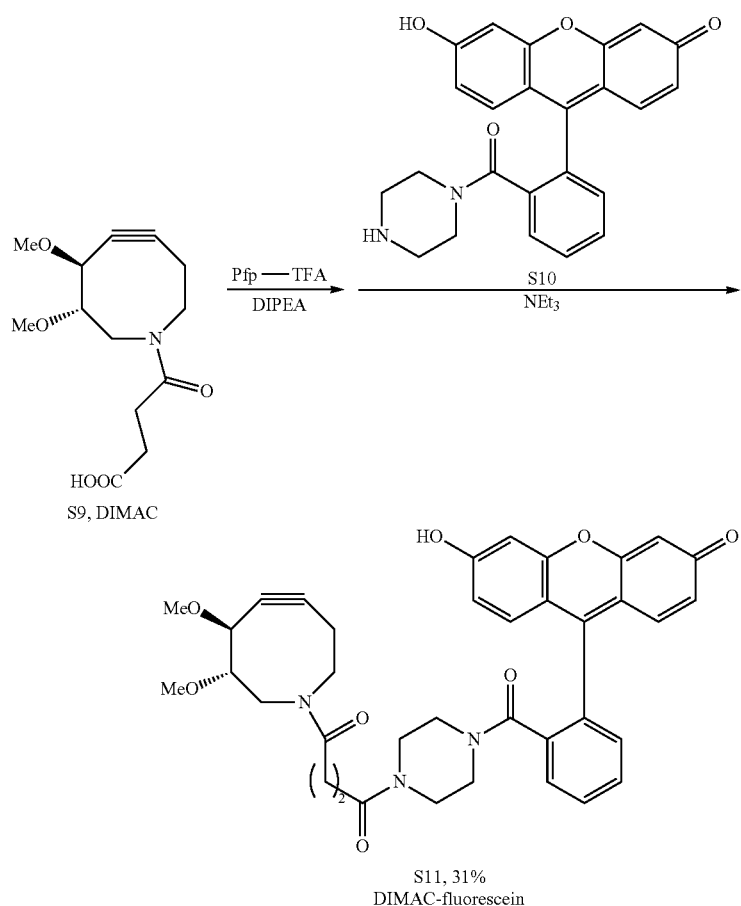

DIMAC-fluorescein (S11). 6,7-dimethoxyazacyclooct-4-yne (DIMAC) (Sletten, E. M.; Bertozzi, C. R. *Org. Lett.* 2008, 10, 3097-3099; S9, 8.0 mg, 0.030 mmol, 1.0 equiv.) was dissolved in CH$_3$CN (1 mL, anhydrous) and cooled to 0° C. DIPEA (10 µL, 0.057 mmol, 1.9 equiv.) was added and the mixture was stirred for 10 min, at which point pentafluorophenyltrifluoroacetate (15 µL, 0.087 mmol, 2.9 equiv.) was added. The reaction was warmed to room temperature and stirred for 1.5 h. It was then evaporated to dryness and purified by silica gel chromatography eluting with toluene/ether (7:1, 5:1, 3:1, anhydrous solvents used for chromatography). This procedure resulted in DIMAC-pentafluorophenyl ester (13 mg, 0.030 mmol, quant.). Half of the DIMAC-pentafluorophenyl ester (6.5 mg, 0.015 mmol, 1.0 equiv.) was dissolved in dimethylformamide (0.5 mL, anhydrous). In a separate flask, fluorescein-piperazine (Hangauer, M. J.; Bertozzi, C. R. *Angew. Chem. Int. Ed.* 2008, 47, 2394-2397; 11 mg, 0.028 mmol, 1.8 equiv.) was dissolved in dimethylformamide (0.5 mL, anhydrous) and DIPEA (~10 µL, 0.06 mmol, 4 equiv.). The DIMAC solution was added to the fluorescein-piperazine solution at 0° C. The reaction was warmed to room temperature over 5 h, at which point it was evaporated to dryness and purified first by silica gel chromatography (5:3:1 EtOAc/MeOH/H$_2$O) then by HPLC (C18 column, with methanol/water, 40-100% methanol over 25 min, elutes at 15 min). This procedure resulted in pure DIMAC-fluorescein (3 mg, 0.005 mmol, 31% yield). R$_f$=0.7 in 5:3:1 ethyl acetate/methanol/water. HRMS (ESI): calcd. for C$_{37}$H$_{37}$O$_8$N$_3$Na [M+Na]$^+$, 674.2473; found, 674.2478.

Scheme

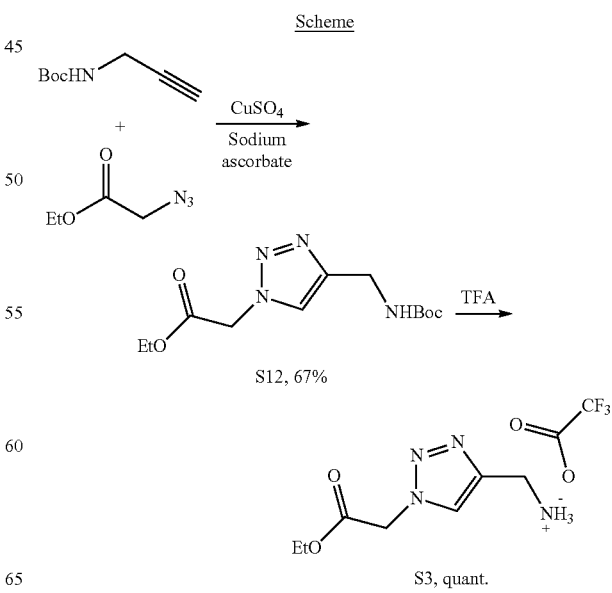

Ethyl 2-(4-((tert-butoxycarbonylamino)methyl)-1H-1,2,3-triazol-1-yl)acetate (S12). Ethyl azidoacetate (120 mg, 0.930 mmol, 1.00 equiv.) and N-boc propargyl amine (146 mg, 0.942 mmol, 1.02 equiv.) were dissolved in a mixture of ethanol (1.8 mL) and water (1.8 mL). To this solution, $CuSO_4$ (2 mg, 0.01 mmol, 0.1 equiv.) and sodium ascorbate (50 µL of 2M solution in water, 0.1 mmol, 1 equiv.) were added. The mixture was stirred overnight at room temperature. The following morning, the ethanol was removed by evaporation and the product was extracted into ethyl acetate (3×50 mL). The ethyl acetate was dried with $MgSO_4$, filtered and evaporated to dryness. The crude product was purified by silica gel chromatography with hexanes/ethyl acetate (5:1, 3:1, 1:1, 1:2). This procedure resulted in 178 mg of pure S12 (0.627 mmol, 67%). $R_f$=0.7 in ethyl acetate. $^1$H NMR (600 MHz, $CDCl_3$): δ 7.61 (s, 1H), 5.34 (s, 1H), 5.08 (s, 2H), 4.34 (d, J=6.0 Hz, 2H), 4.19 (q, J=7.1 Hz, 2H), 1.37 (s, 9H), 1.23 (t, J=7.1 Hz, 3H). $^{13}$C NMR (150 MHz, $CDCl_3$): δ 166.3, 155.9, 145.9, 123.4, 79.5, 62.3, 50.8, 36.0, 28.3, 14.0. HRMS (ESI): calcd. for $C_7H_{13}O_2N_4$ $[M+H]^+$, 185.1039; found, 185.3.

(1-(2-ethoxy-2-oxoethyl)-1H-1,2,3-triazol-4-yl)methanaminium 2,2,2-trifluoroacetate (S3). Boc-protected triazole S12 (178 mg, 0.627 mmol, 1 equiv.) was dissolved in dichlorometane (8 mL, anhydrous). Trifluoroacetic acid (2 mL) was added and this mixture was stirred for 1 h at room temperature, at which point the reaction mixture was evaporated to dryness to yield pure S3 (200 mg, 0.67 mmol, quant.). $R_f$=0.7 in 5:3:1 ethyl acetate/methanol/water. $^1$H NMR (600 MHz, MeOD): δ 8.15 (s, 1H), 5.34 (s, 2H), 4.31 (s, 2H), 4.23 (q, J=7.1 Hz, 2H), 1.27 (t, J=7.1 Hz, 3H). $^{13}$C NMR (151 MHz, MeOD): δ 168.6, 161.3 (q, J=38.3 Hz), 141.5, 127.4, 117.2 (q, J=287.3 Hz), 63.6, 52.0, 35.6, 14.4. HRMS (ESI): calcd. for $C_{12}H_{21}O_4N_4$ $[M+H]^+$, 285.1563; found, 285.3.

Example 2

Bioorthogonal Quadricyclane Ligation

To identify a bioorthogonal reaction partner for quadricyclane, a variety of candidates for reactivity were screened at room temperature in aqueous or polar aprotic solvents. One example of a reagent that stood out as promising is bis(dithiobenzil)nickel(II) 2, a Ni bis(dithiolene) complex that reacted cleanly with 7-acetoxy quadricyclane 1 to yield adduct 3.

Figure 2:
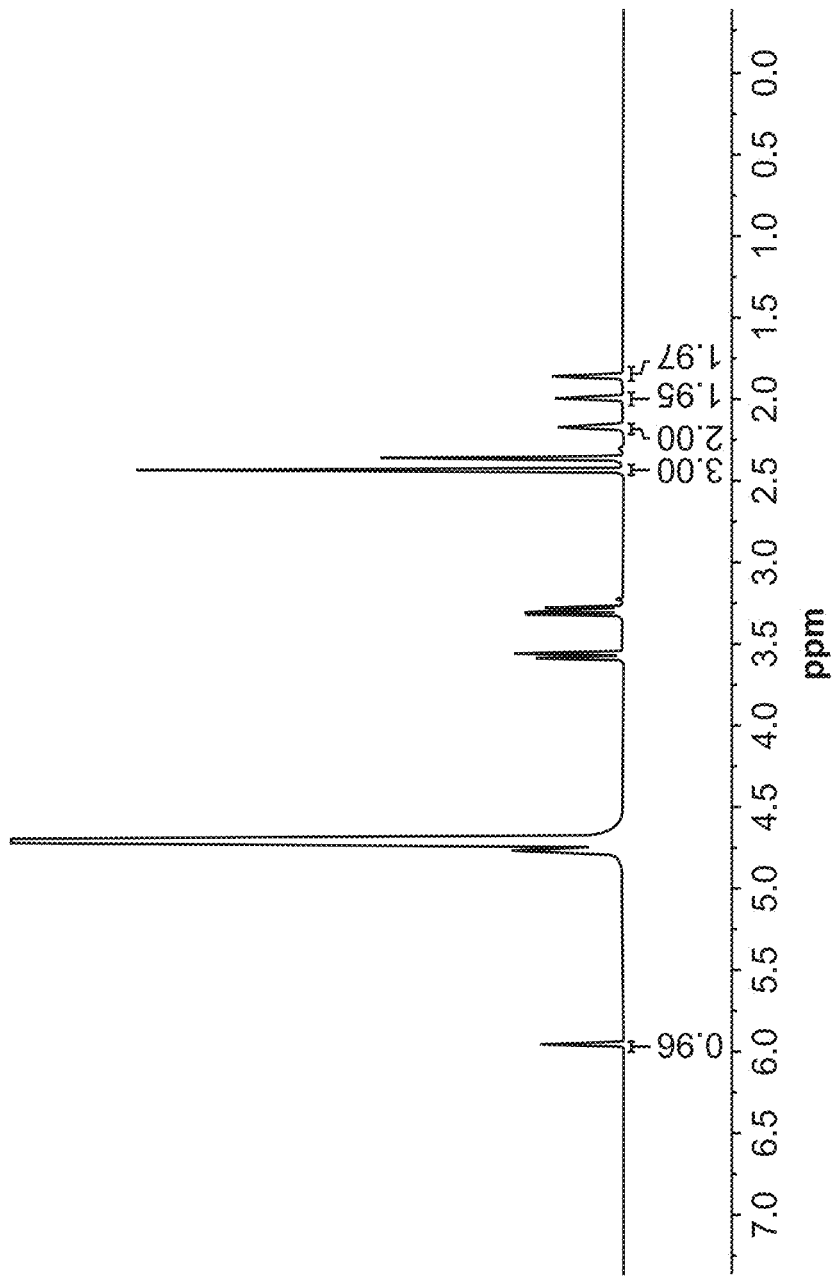
FIG. 2 is a spectrum that shows that quadricyclane is stable to cysteine. 7-acetoxy quadricyclane (1, 2 mg) was dissolved in 0.4 mL of $CD_3CN$. To this solution, 0.4 mL of deuterated PBS and 3 mg of cysteine were added. The NMR spectrum above was taken 2.5 months after the described solution was prepared.
Figure 3:
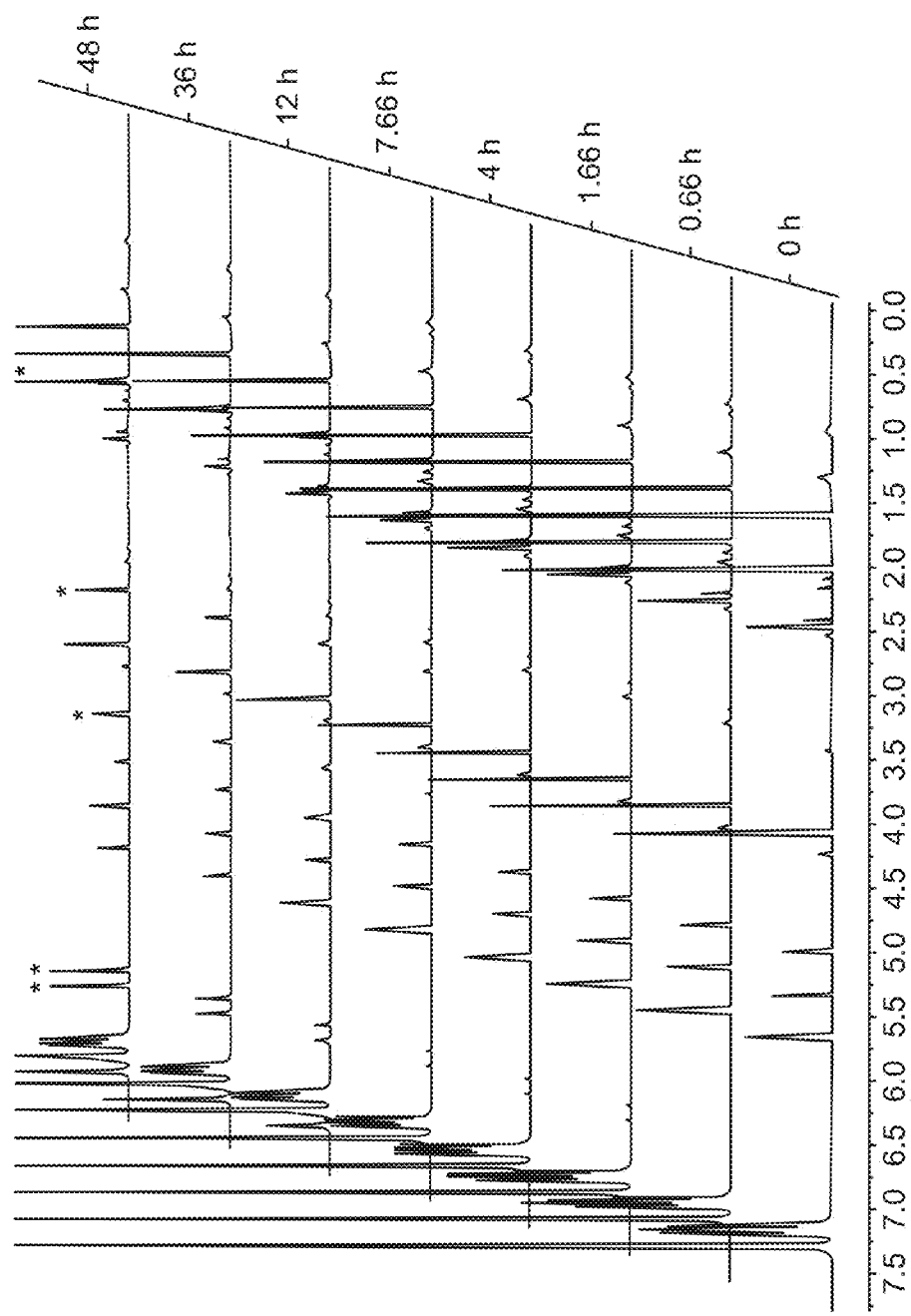
FIG. 3 is a spectrum that shows that Complex 3 is photo-labile. Complex 3 (2.2 mg) was dissolved in $CDCl_3$ (~0.75 mL) and placed in an NMR tube on the bench continually exposed to ambient light. NMR spectra were periodically obtained. The asterisks indicate the chemical shifts for 7-acetoxy norbornadiene (4). At the 36 h time point, there is a 1:1.1 ratio of 3:4 as judged by integration of the olefin peaks. The calculated half-life based on all integration data is 34.8 h.
Figure 4:
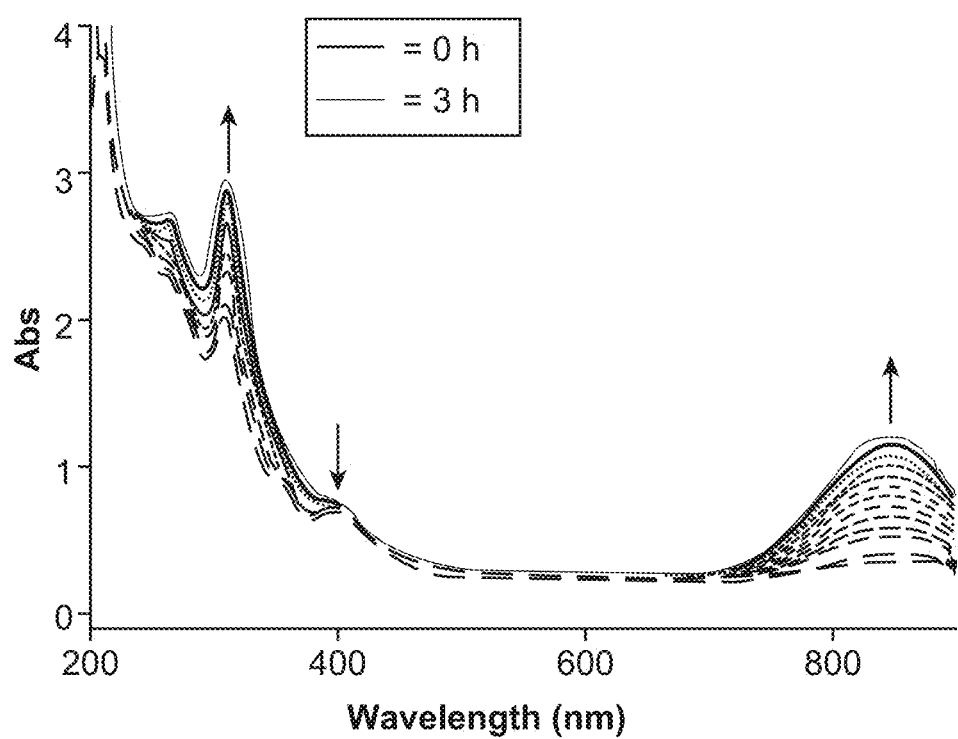
FIG. 4 is a spectrum that shows that Complex 3 is photo-labile. Using an NMR assay degradation of 3 over the first few hours is not evident. However, using UV/Vis/NIR spectroscopy, which has greater sensitivity than NMR, the formation of 2 from 3 is evident at early timepoints. A solution of 3 was prepared in $CH_3CN$ and left in ambient light. A UV/Vis/NIR spectrum was obtained every 15 min. The NIR absorption band at 855 nm characteristic of 2 is growing in, while the small hump centered at ~400 nm characteristic of the product is decreasing. The absorption band at 350 nm is also increasing in intensity.

The aqueous stability of quadricyclane has been the subject of conflicting reports, and thus, the stability of 1 was assayed in water and in the presence of biological nucleophiles. Compound 1 was prepared by the photochemical [2+2] reaction of 4. Compound 1 was found to be stable in phosphate buffered saline (PBS, pH 7.4) with no degradation observed after more than 2 months at room temperature (FIG. 1). We also found Compound 1 to be unreactive with sugars, a variety of oxidants, and free amino acids, most notably cysteine (FIG. 2). Furthermore, quadricyclane was stable in the presence of bovine serum albumin (BSA) and cell culture media under conditions emulating those necessary for metabolic labeling experiments. The limited solubility of Compound 2 in polar solvents precluded a thorough stability study, but the compound was found to be unreactive with a variety of nucleophiles in dichloromethane. It is worth noting that the Ni bis(dithiolene) core is considered aromatic, no doubt contributing to it general stability.

The stability of the product, norbornene 3, formed by ligation of 1 and 2 was studied. There are reports that quadricyclane's adduct with 2 undergoes light-induced reversion to norbornadiene, an isomer of quadricyclane, and 2. Accordingly, Compound 3 was exposed to ambient light and monitored the formation of 2 and 4. The half-life of the reversion was ~35 hours in $CDCl_3$ (FIG.S. 3-4), which would be problematic for many biological labeling applications.

Figure 5:
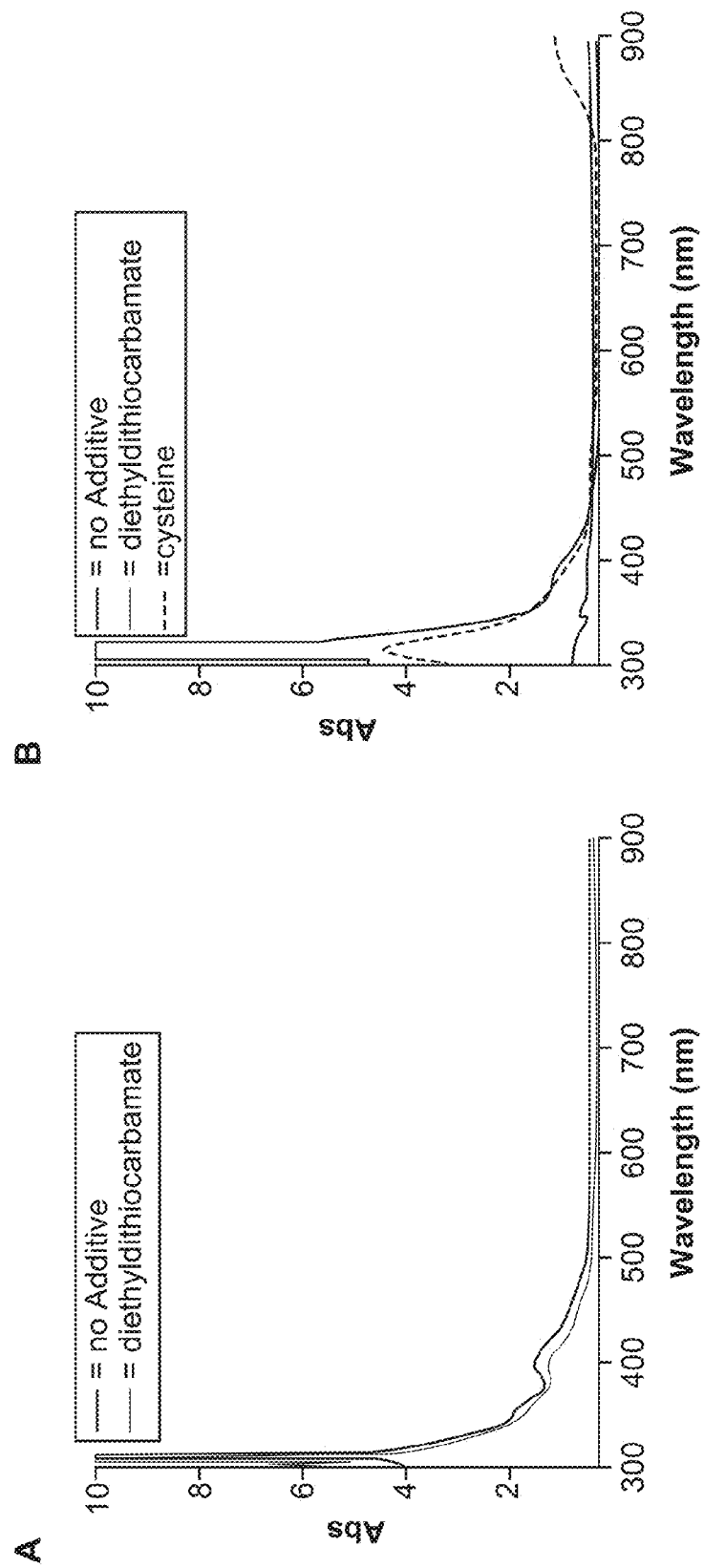
FIGS. 5A and 5B are spectra that show that diethyldithiocarbamate (5) prevents the photo-degradation of complex 3. A solution containing 200 μM 3 and 0 (red) or 1.25 (green) mM 5 in 3:1 $CH_3CN/H_2O$ was prepared and left in ambient light continually. A. UV/Vis/NIR spectra of the described solutions taken before being exposed to light. B. UV/Vis/NIR spectra of the described solutions taken after 20 h of exposure to light. The red line contains little absorbance due to the low solubility of 2 in acetonitrile. If 2 is reduced to the anionic state by cysteine (1.25 mM, blue line) solubility in acetonitrile is improved and evidence of photodegradation can be seen. The diethyldithiocarbamate treated sample remains unaltered after exposure to light indicating no photodegradation occurred.
Figure 6:
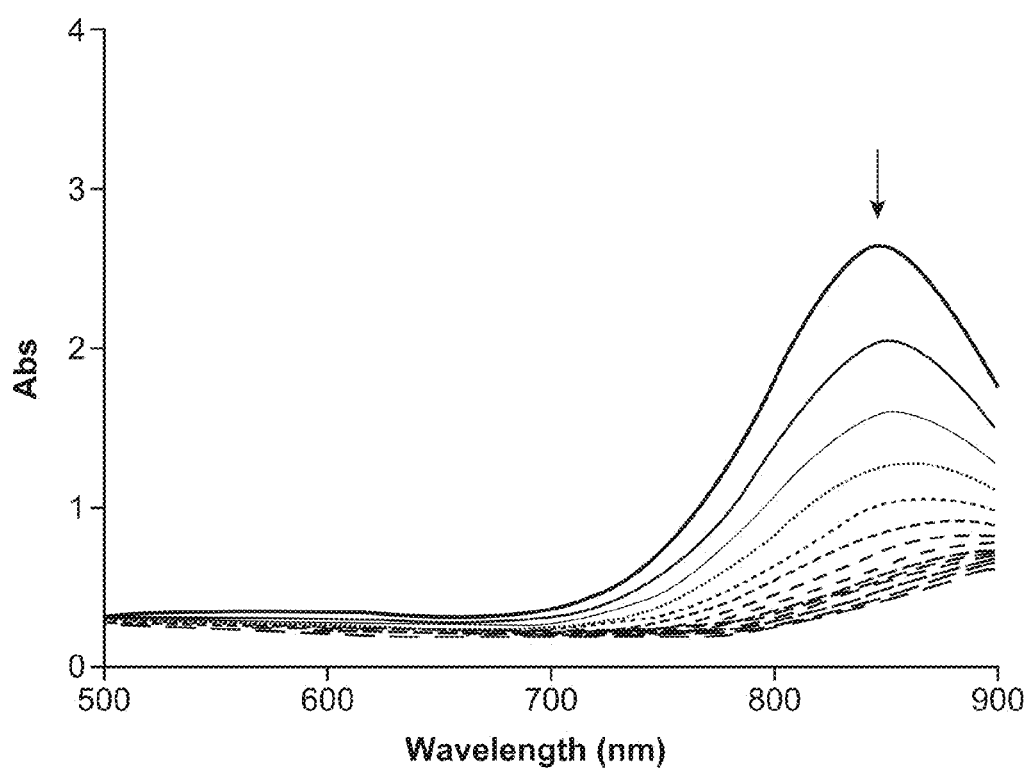
FIG. 6 is a spectrum that monitors the reaction between 1 and 14. A series of UV/Vis/NIR spectra taken as the reaction in part A is proceeding. A solution of 14 (400 μM in PBS) was combined with 1 (20 mM in EtOH) and a UV/Vis/NIR spectrum was taken every 30 seconds.
Figure 7:
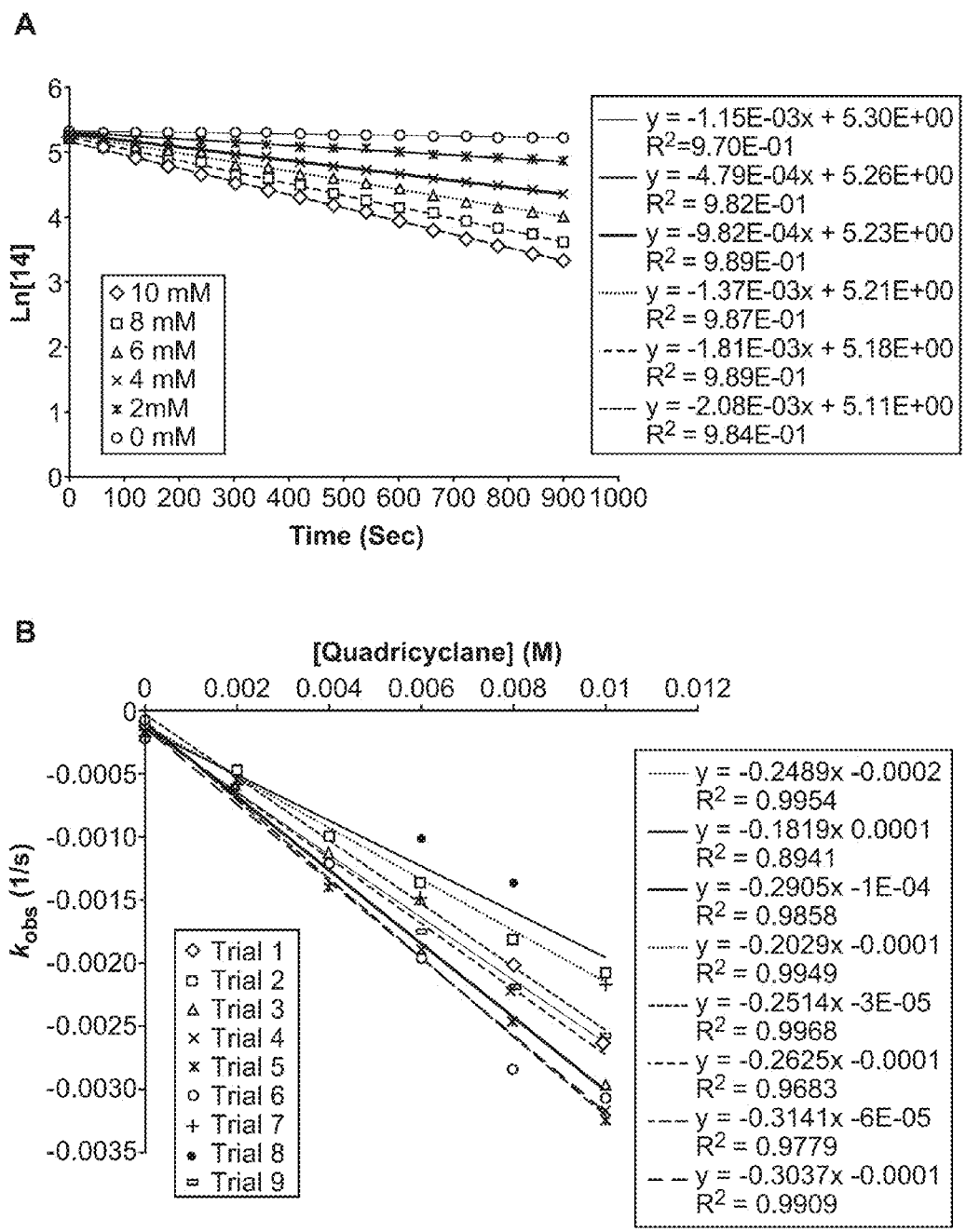
FIGS. 7A and 7B are graphs that show the second-order rate constant for the reaction of 1 and 14 was determined using pseudo-first order kinetics. A solution of 400 μM 14 in PBS was combined with various solutions of quadricyclane 1 (20 mM, 16 mM, 12 mM, 8 mM, 4 mM, or 0 mM in EtOH) in a 1:1 ratio (total volume=100 μL). The reaction was monitored by the absorbance at 850 nm for 15 min. The absorbance values were correlated to the concentration of 14 using a standard curve. A plot of Ln [14] verses time resulted in a series of first-order rate constants ($k_{obs}$). Plotting each $k_{obs}$ value vs. [1] yields a linear regression with the slope of the line indicating the second-order rate constant. The average of nine trials resulted in a second-order rate constant of 0.25±0.05 $M^{-1}s^{-1}$. A. A representative plot to determine $k_{obs}$. B. Plot of $k_{obs}$ vs. [1] for each trial.

The mechanism of the photochemical reversion is not well understood, but it is presumed that the reaction could be inhibited by removing Ni from the product using a metal chelator. After screening a variety of options, it was found that diethyldithiocarbamate (5) prevented the photodegradation of 3, as shown below. (FIG. 5).

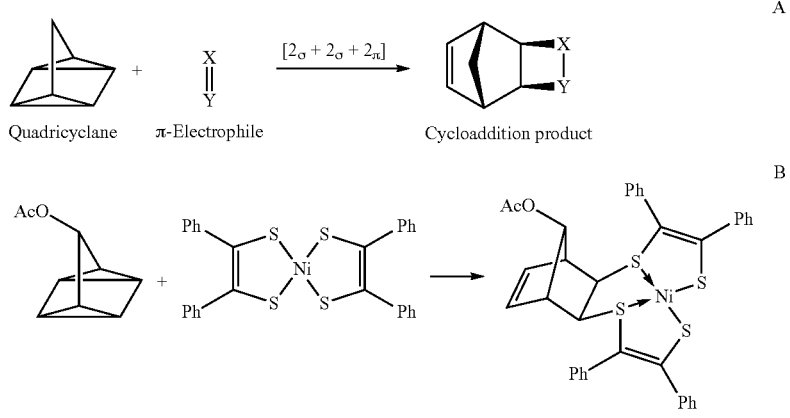

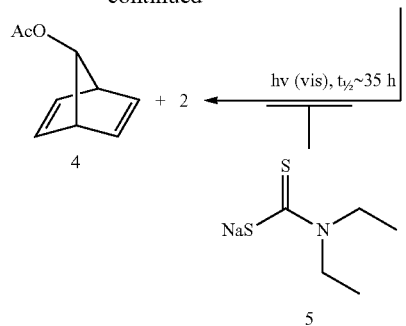

With these promising results, the synthesis of a Ni bis (dithiolene) reagent that is both water soluble and functionalized with a probe to detect biomolecule labeling was pursued. Compound 15, bearing two sulfonate groups and two biotin moieties, was designed for this purpose. Compound 15 and a model compound, bis(isopropyl amide) 14, from dithiol-2-one ligand precursors using a previously reported route that we felt would be compatible with polar functional groups were prepared. Briefly, alkyne 6 was reacted with xanthogen disulfide 7 in the presence of the radical initiator 1,1'-azobis(cyclohexanecarbonitrile) to yield dithiocarbonate 8. Treatment of 8 with fuming sulfuric acid installed a single sulfonate group and also hydrolyzed the methyl ester to produce 9 in good yield. Standard amide bond coupling conditions were used to conjugate either isopropyl amine or an amine-functionalized biotin derivative to 9, affording 10 and 11, respectively. These intermediates were then converted to anionic Ni bis(dithiolene) species 12 and 13 in situ by treatment with tetramethyl ammonium hydroxide and $NiCl_2$. Immediate subsequent oxidization with 0.5 equivalents of iodine afforded the desired neutral complexes 14 and 15. Compounds 14 and 15 are soluble in PBS at concentrations up to 5 and 10 mM, respectively.

With the solubilities of compounds 14 and 15, reaction kinetics were assessed with quadricyclane in aqueous/organic solvent mixtures, as well as to probe in more detail the stability of these Ni bis(dithiolene) complexes in the presence of biomolecules. Complex 14 has a large NIR absorption band at 850 nm that is not present in the adduct with quadricyclane, allowing for pseudo-first order kinetic measurements by absorption spectroscopy. The second-order rate constant for the reaction of 14 and 1 in a 1:1 PBS/EtOH mixture was $0.25 \pm 0.05$ $M^{-1}s^{-1}$ at room temperature (FIG.S. 6-7). This rate constant is comparable to those of cyclooctyne-azide cycloadditions currently used for biological labeling applications, and should allow for use of mild reaction conditions (<200 μM reagent, <1 h reaction times).

Figure 8:
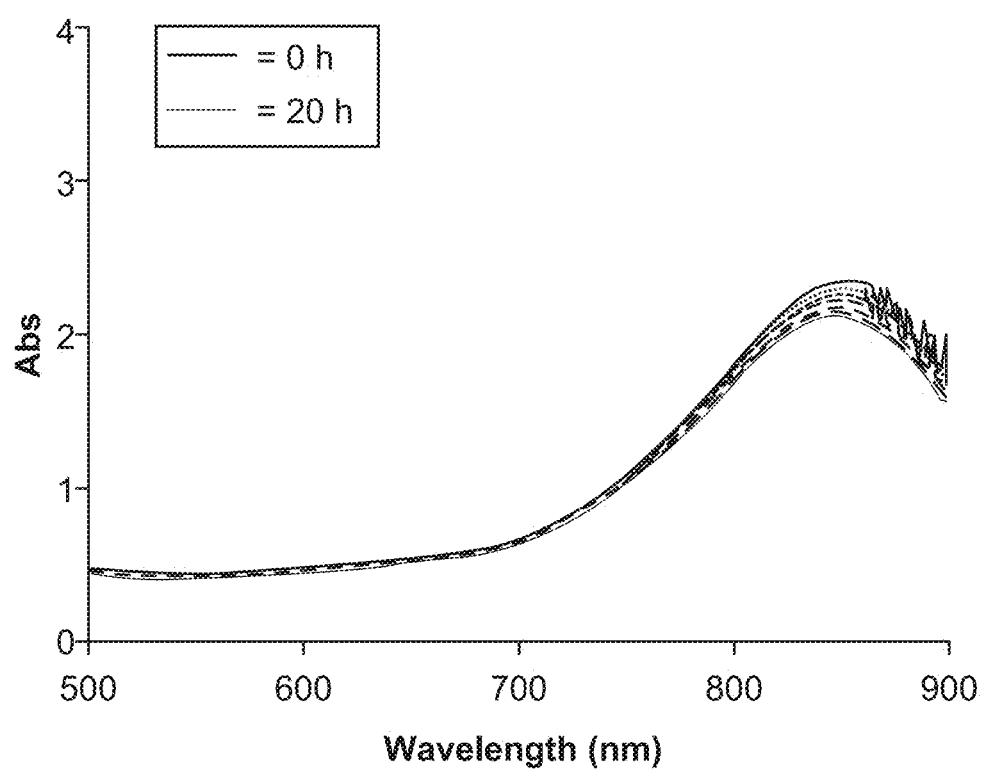
FIG. 8 is a graph that shows the stability of Ni bis (dithiolene) 14 is stable to PBS. Ni bis(dithiolene) 14 was dissolved in PBS. The absorption of the NIR band was monitored for changes over 20 h. A UV/Vis/NIR spectrum was taken every hour. Only slight reduction in signal is evident.
Figure 9:
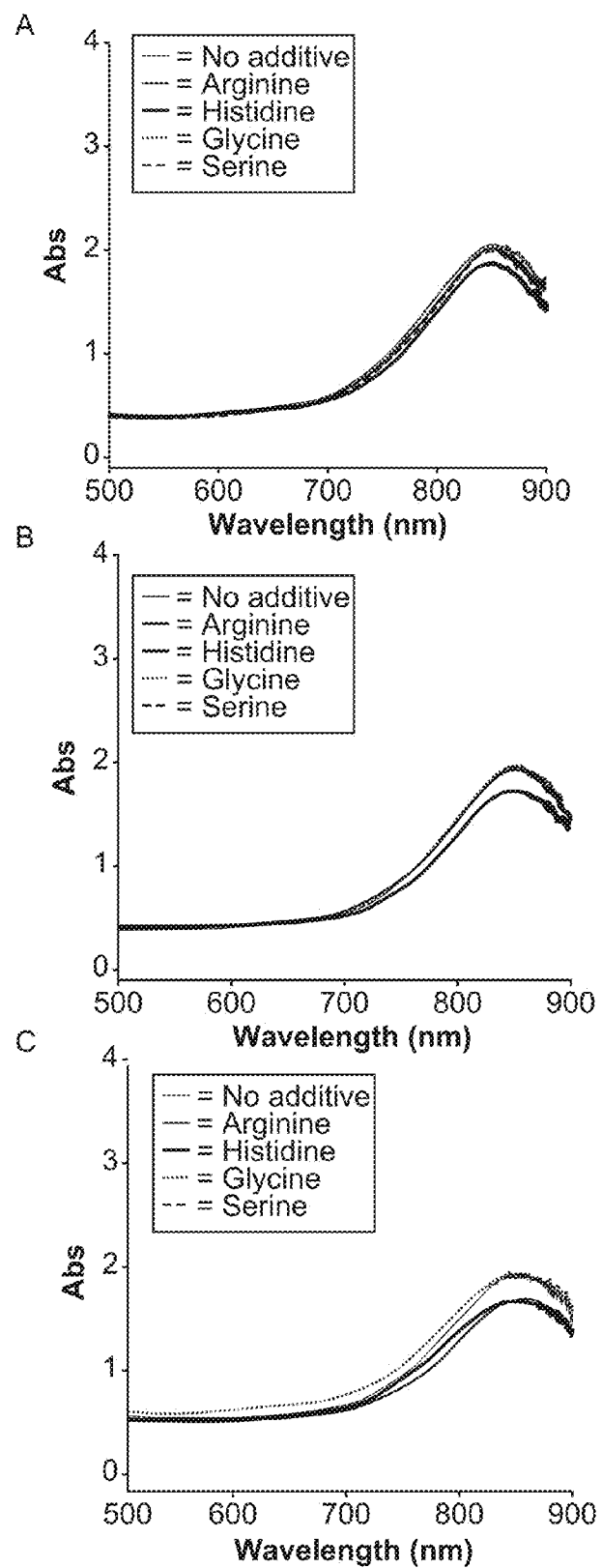
FIGS. 9A-C are graphs showing the stability of Ni bis (dithiolene) 14 is moderately stable to excess of free amino acids. A solution of 400 μM 14 in PBS was combined with solutions of 50 mM of the indicated amino acid in a 1:1 ratio. The absorbance of each solution was monitored over time. A. The UV/Vis/NIR spectra taken after approximately 15 min. B. The UV/Vis/NIR spectra taken after 1 h. C. The UV/Vis/NIR spectra taken after 2 h. Red=no amino acid present. Green=arginine. Blue=histidine. Black=glycine. Purple=serine.
Figure 10:
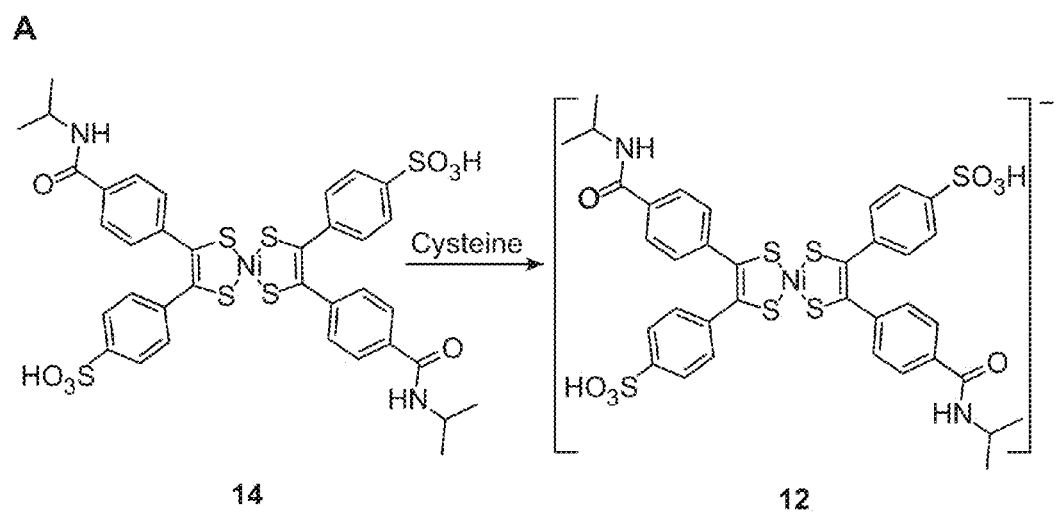
FIGS. 10A and 10B show that Ni bis(dithiolene) 14 is not stable to cysteine. A. Schematic for the reduction of 14 to 12 by free cysteine. B. UV/Vis/NIR analysis of the reaction between 14 and cysteine. A solution of 125 µM 14 in PBS was prepared with 0 (red), 1 (blue), 10 (green) or 100 (black) equivalents of cysteine. All the mixtures instantly turned orange upon addition of cysteine and displayed the UV/Vis/NIR spectra shown above. A smaller, red-shifted NIR absorption band is consistent with reduction of 14 to 12.
Figure 10:
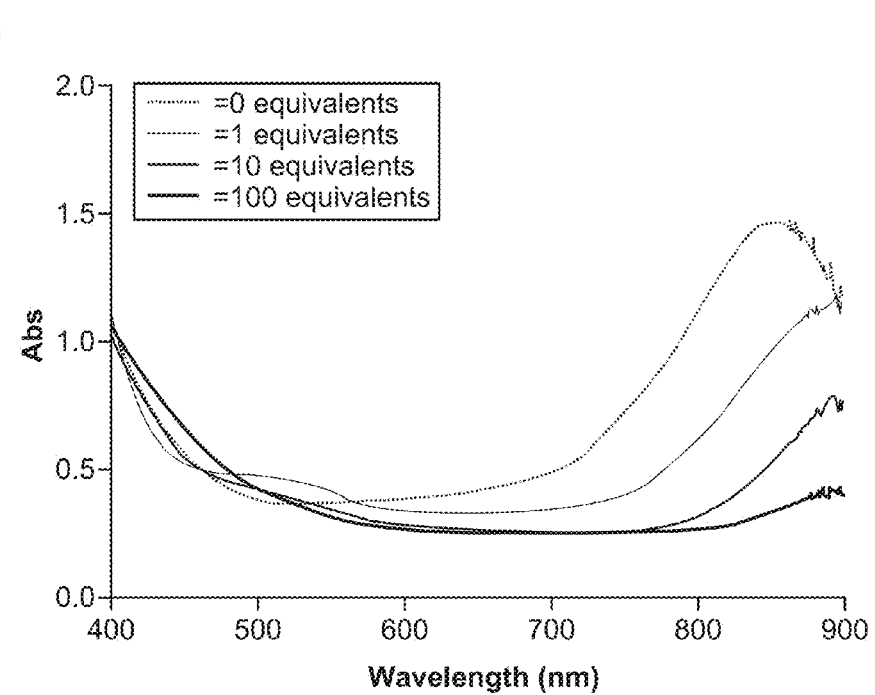
Figure 11:
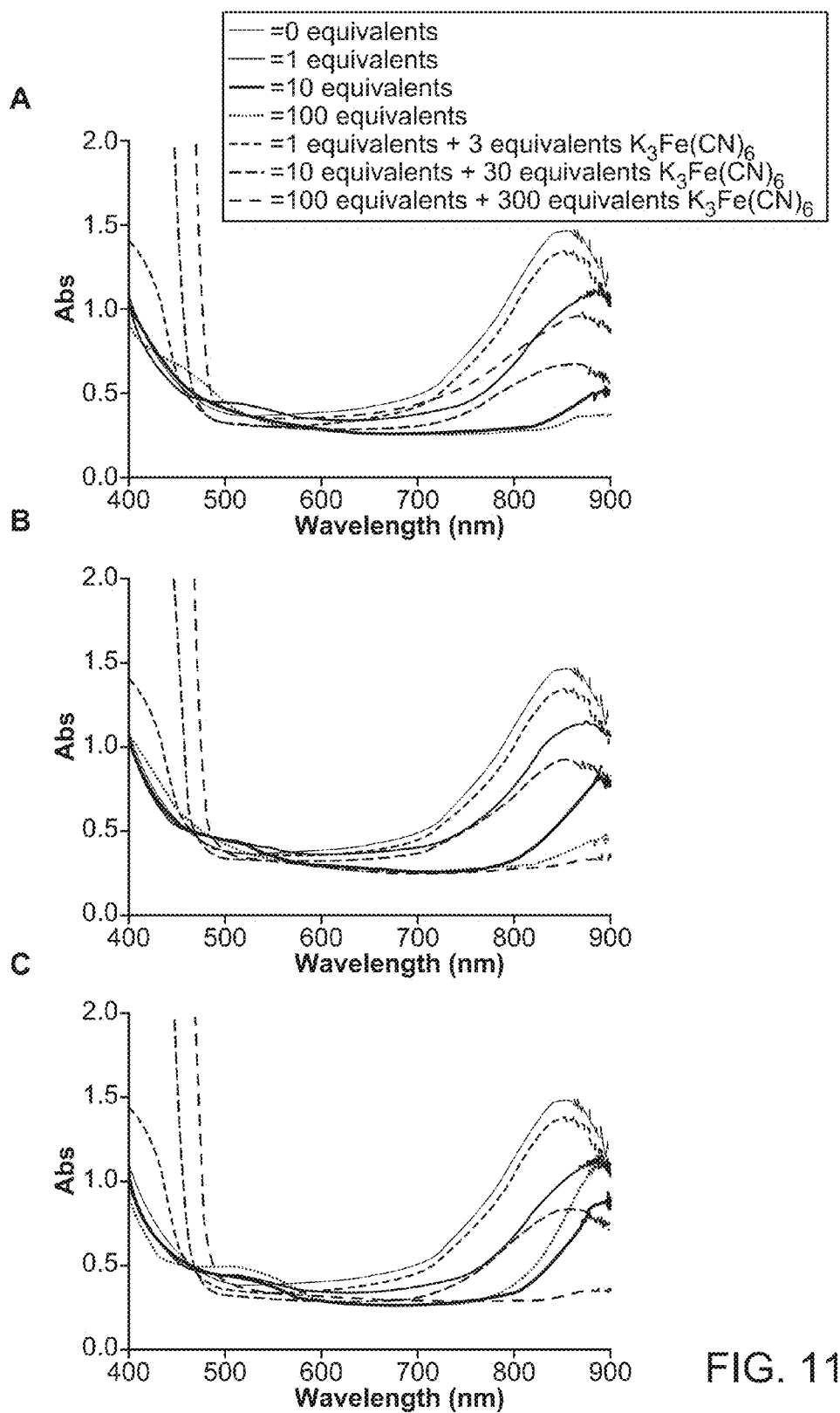
FIGS. 11A-C are graphs showing that Ni bis(dithiolene) 14 is not stable to reducing agents. A solution of 125 µM 14 in PBS was prepared with 0 (red), 1 (blue, solid), 10 (green, solid) or 100 (black, solid) equivalents of β-mercaptoethanol (BME, A), tris(carboxyethyl)phosphine (TCEP, B), or N-acetyl cysteine (C). All the mixtures instantly turned orange upon addition of reducing agent and displayed the UV/Vis/NIR spectra shown above. A smaller, red-shifted NIR absorption band is consistent with reduction of 14 to 12. For the cases of 1 and 10 equivalents of reducing agent, 14 could be recovered by the addition of 3 equivalents or 30 equivalents of potassium ferrocyanide ($K_3Fe(CN)_6$), respectively (blue or green dashed lines). However, the addition of 300 equivalents of $K_3Fe(CN)_6$ did not restore 14 when 14 was subjected to 100 equivalents of reducing agent (black dashed line).
Figure 12:
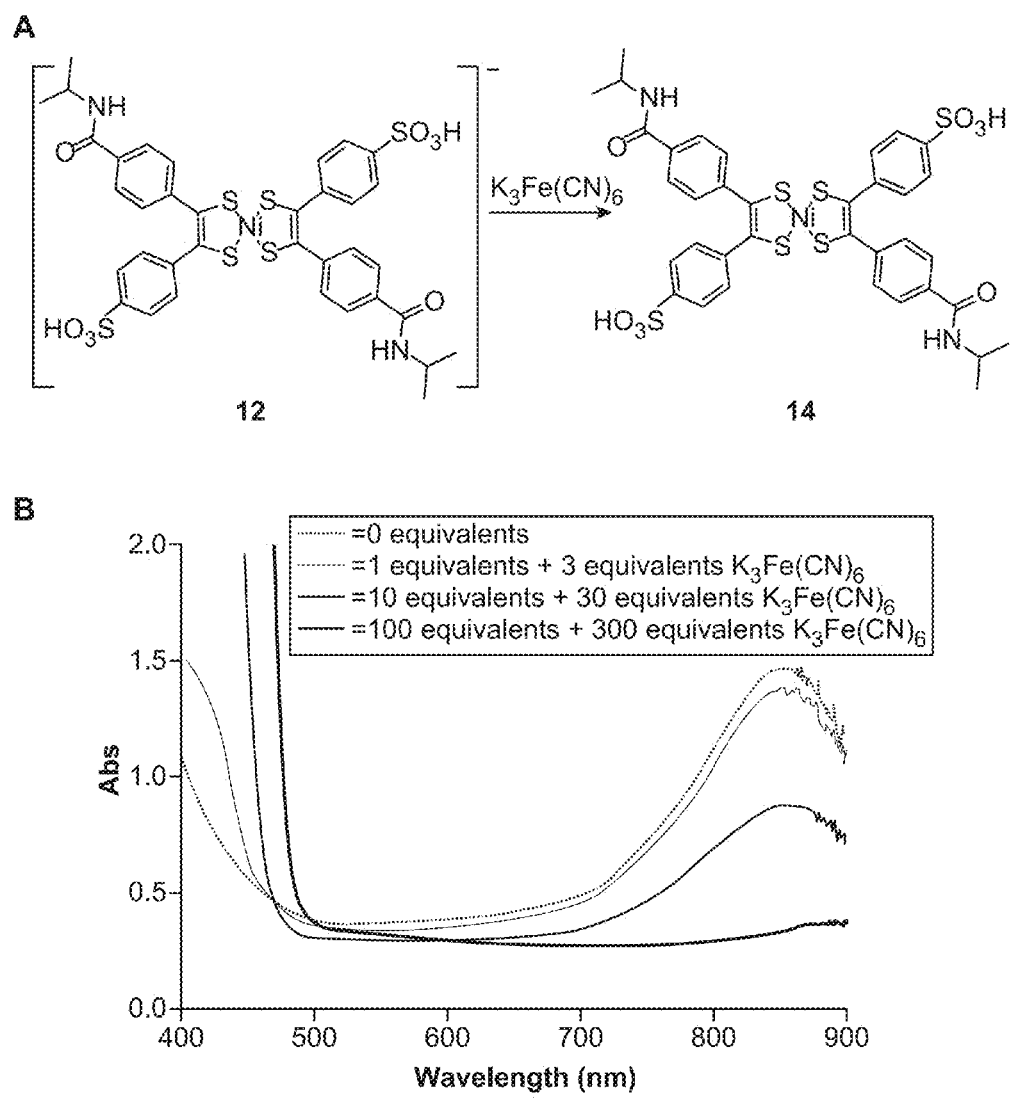
FIGS. 12A and 12B show that Ni bis(dithiolene) 14 can be rescued by addition of $K_3Fe(CN)_6$. A. Schematic for the oxidation of 12 to 14. B. UV/Vis/NIR analysis of the oxidation. A solution of 125 µM 14 in PBS was treated with 1, 10, or 100 equivalents of cysteine followed by 3, 30, or 300 equivalents of $K_3Fe(CN)_6$, respectively (blue, green, black dashed lines). After 1 h, UV/Vis/NIR spectra were collected. The red line represents 125 µM 14 with no treatment.
Figure 13:
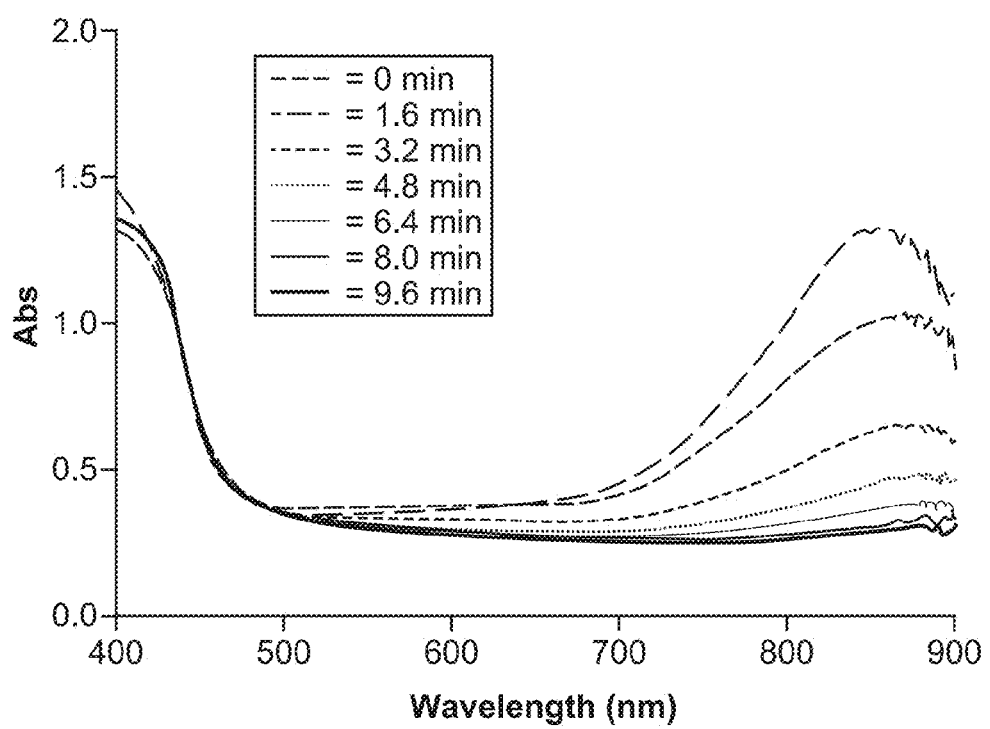
FIG. 13 is a graph that shows that Ni bis(dithiolene) 14 rescued by the addition of $K_3Fe(CN)_6$ reacts with quadricyclane. A solution of 125 µM 14 in PBS was treated with 1 equivalent of cysteine followed by 3 equivalents of $K_3Fe(CN)_6$. Quadricyclane was added and a UV/Vis/NIR spectrum was immediately recorded (red line). UV/Vis/NIR spectra were then collected every 1 min and 40 sec. The observed reduction in signal is consistent with the quadricyclane ligation occurring (See FIG.ure S6).
Figure 14:
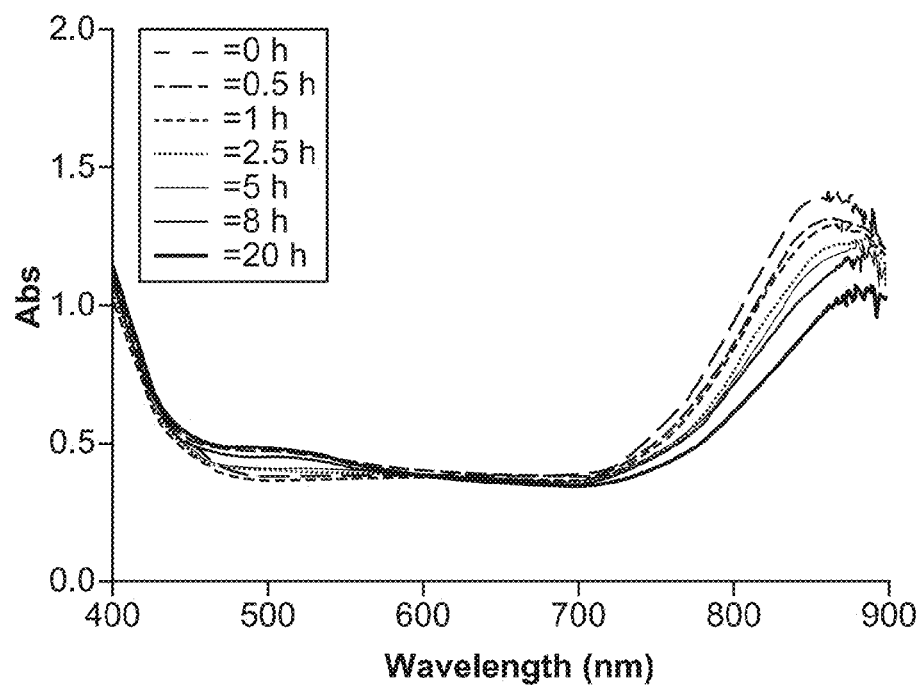
FIGS. 14A and 14B are graphs showing that Ni bis (dithiolene) 14 is reduced by bovine serum albumin (BSA). A solution containing 14 (100 µM) and BSA (1.2 equivalents (A) or 12 equivalents (B)) was monitored by UV/Vis/NIR spectroscopy at various timepoints over 20 h. UV/Vis/NIR spectra were normalized to each other at 650 nm.
Figure 14:
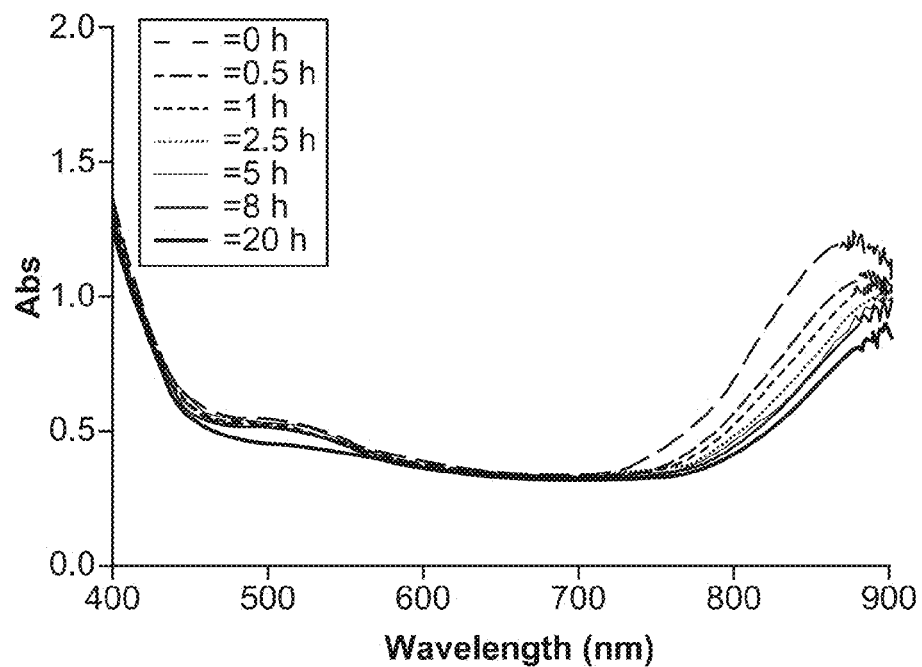
Figure 15:
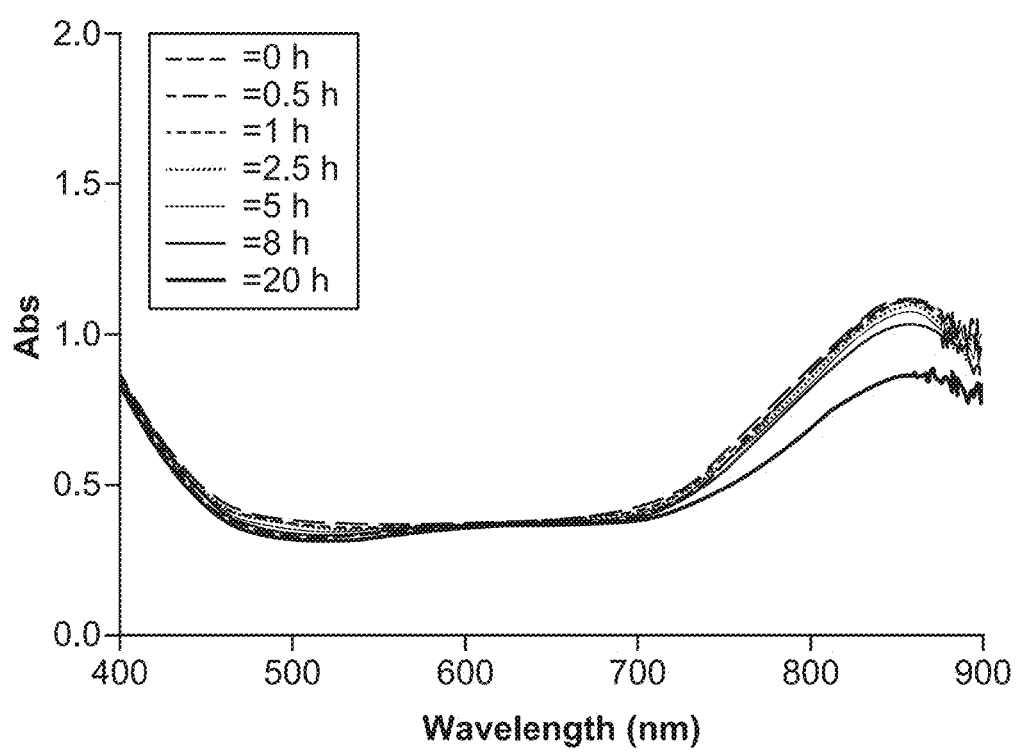
FIG. 15 is a graph that shows that Ni bis(dithiolene) 14 is stable to oxidized insulin over multiple hours. A solution containing 14 (100 µM) and oxidized insulin (1.2 equivalents) was monitored by UV/Vis/NIR spectroscopy at various timepoints over 20 h. UV/Vis/NIR spectra were normalized to each other at 650 nm.

The stability of 14 was also monitored using the NIR absorption band, which is dependent on both the oxidation state of the complex (i.e., 14 vs. 12) as well as the connectivity of the dithiolene ligands. Absorption at 850 nm remained essentially unaltered when 14 was incubated in PBS for 20 h (FIG. 8). As well, exposure to amino acids had either no effect or a minimal effect on the absorption intensity (FIG. 9). A marked exception was cysteine, which even at 1 molar equivalent caused an immediate decrease in the 850 nm absorption band's intensity and concomitant appearance of a new absorption at ~900 nm (FIG. 10). This transformation is consistent with reduction of 14 to 12 and treatment of 14 with other reducing agents yielded similar results (FIG. 11). The neutral complex could be regenerated by addition of potassium ferrocyanide ($K_3Fe(CN)_6$) as judged by the reappearance of the absorption band at 850 nm and restoration of reactivity with 1 (FIG.S. 12-13). Concerned that the presence of free cysteine residues within proteins would undergo unwanted redox reactions with 14, we monitored its integrity the presence of BSA, which possesses a solvent-exposed reduced cysteine side chain. Incubation with BSA led to reduction of 14 but at a much slower rate (>1000-fold) than observed with free cysteine. Therefore, protein-mediated reduction should not undermine the much faster quadricyclane ligation (FIG. 14). Notably, 14 was stable to oxidized insulin, which contains no free sulfhydryl groups, over a 5 hour period (FIG. 15).

Figure 16:
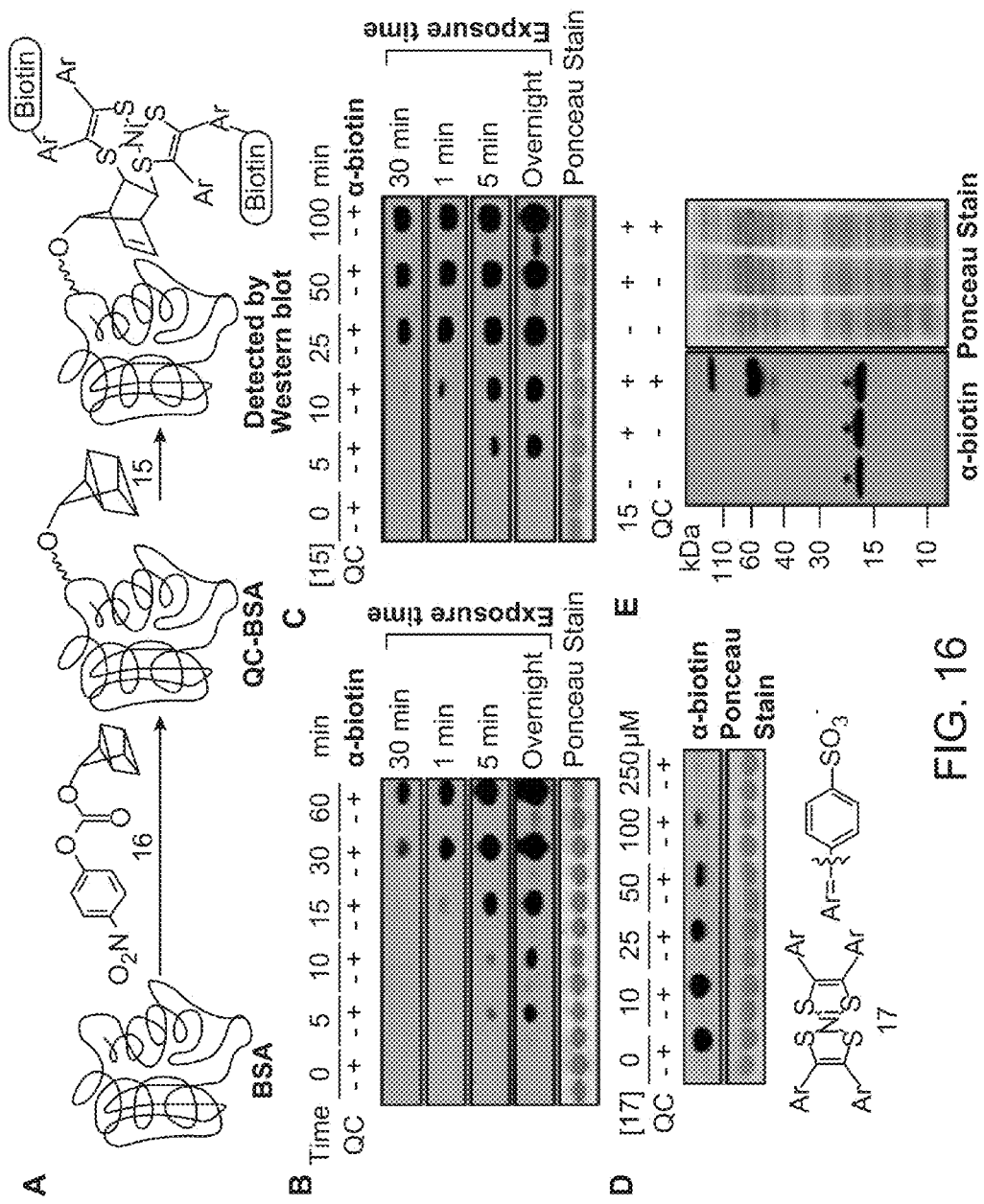
FIGS. 16A-E show that Ni bis(dithiolene) reagents selectively label quadricyclane-modified BSA. A. Modification of BSA with quadricyclane and subsequent labeling with a biotinylated nickel dithiolene reagent. B/C. Ni bis(dithiolene) 15 displays time (B)- and dose (C)-dependent labeling of QC-BSA. BSA (−) or QC-BSA (+) (5 µg) was treated with 50 µM 15 for various amounts of time (B) or various concentrations of 15 for 30 min (C). The reactions were quenched with 1 and 5 and the presence of product was detected by Western blot using c'-biotin-HRP. D. Reaction of 15 with QC-BSA can be prevented by pretreatment with tetrasulfonated Ni bis(dithiolene) 17. BSA (−) or QC-BSA (+) (5 µg) was treated with varying amounts of 17 for 30 min followed by 50 µM of 15 for 30 min. The reactions were quenched with 1 and 5 and the samples were analyzed by Western blot probing with α-biotin-HRP. E. QC-BSA can be selectively labeled in a mixture of proteins. To 25 µg of lysate in the presence of 1 mM $K_3Fe(CN)_6$ was added no BSA or reagent (lane 1), BSA (1.5 µg) and 50 µM 15 (lane 2), or QC-BSA (1.5 µg) and 50 µM 15 (lane 3). After 30 min, the reactions were quenched with 1 and 5 and analyzed by Western blot. The BSA monomer and dimer bands are visible in the QC-BSA treated sample. The bands denoted with an asterisk represent an endogenously biotinylated *E. coli* protein. B-E. Equal protein loading was verified by Ponceau stain.

The quadricyclane ligation was then subjected to a test of bioorthogonality: selective protein labeling. The lysine residues on BSA were modified with quadricyclane p-nitrophenyl carbonate 16 (FIG. 16A).

Preparation of QC-BSA

Bovine serum albumin (100 mg, Sigma) was dissolved in PBS (5 mL). Quadricyclane p-nitrophenyl carbonate 16 (5 mg, 0.02 mmol) was dissolved in dimethylsulfoxide (DMSO) (300 μL) with a small amount of DMF (60 μL). A portion of the BSA solution (0.5 mL) was combined with the quadricyclane solution (100 μL) and DMSO (200 μL). The mixture instantly turned yellow indicating release of p-nitrophenol. After 3 hr, the protein was purified on a NAP-5 column. The column was pre-equilibrated with PBS (10 mL). A portion of the protein mixture (350 μL) was added to the column and eluted with PBS (500 μL per fraction). Four fractions were collected with the second fraction containing the most protein. Protein concentrations were assayed by a NanoDrop2000 (Thermo Scientific) and a BioRAD $D_c$ assay.

Quadricyclane-modified BSA (QC-BSA) or native BSA were treated with 50 μM 15 for various amounts of time and, after quenching with excess 5 and 1, assayed the products by Western blot probing with an anti-biotin (α-biotin) antibody conjugated to horse-radish peroxidase (α-biotin HRP).

Western Blot Procedures

The described protein mixtures were quenched with diethyldithiocarbamate 5 and quadricyclane 1 (3-15 mM). 4× sodium dodecyl sulfate (SDS)-loading buffer (with β-mercaptoethanol (BME)) was added and the protein mixtures were loaded onto a 12% BisTris gel (BioRAD, Criterion). The gel was run at 200 V in 2-(N-morpholino)ethanesulfonic acid (MES) buffer. Proteins were transferred to nitrocellulose (0.45 BioRAD) over 90 min at 75 V. The nitrocellulose was then treated with Ponceau stain and incubated in blocking buffer (5% BSA in PBS with 0.1% Tween 20 non-ionic detergent) for 2 h at rt. Anti-biotin antibody conjugated to horse-radish peroxidase (α-biotin-HRP, Jackson Labs) was added to the blocking buffer (1:100,000 dilution) and incubated at rt for 1 h. The blot was washed with PBST (PBS with 0.1% Tween 20, 3×10 min) and detection was performed by chemiluminescence using Pierce SuperSignal West Pico Chemiluminescent Substrate.

Figure 17:
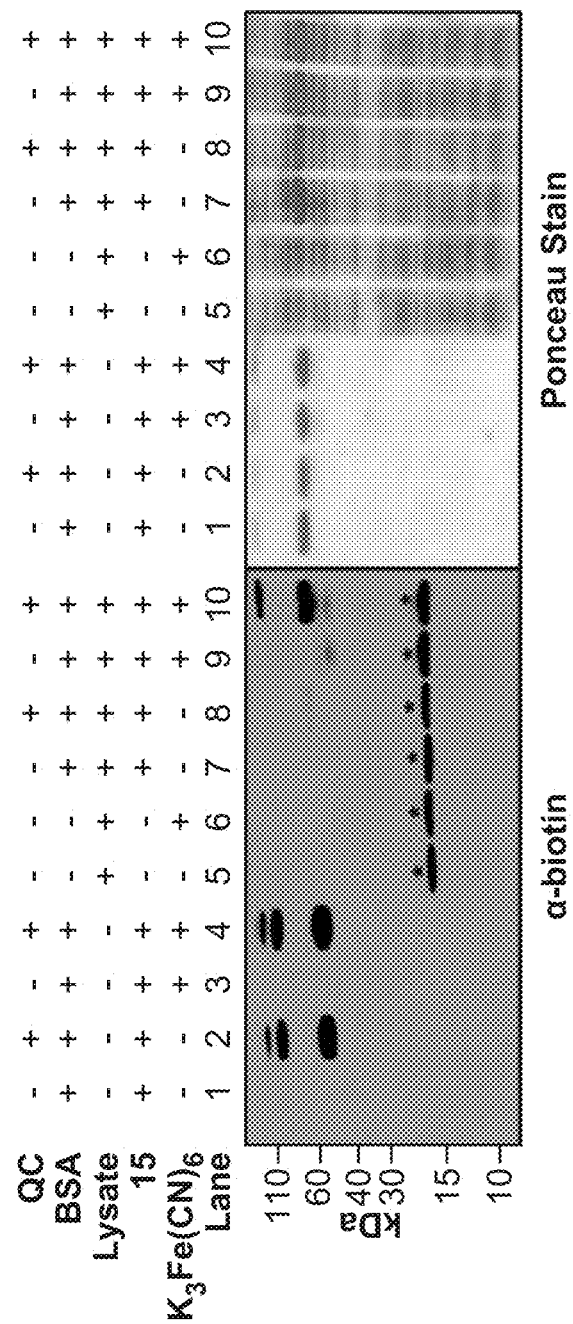
FIG. 17 shows that Oxidizing agent increases the efficiency of labeling of QC-BSA by 15. BSA (1.5 µg, lanes 1, 3) or QC-BSA (1.5 µg, lanes 2, 4) were combined with 15 (50 µM) for 30 min in the presence (lanes 3-4) or absence (lanes 1-2) of 1 mM $K_3Fe(CN)_6$. Lysate from *E. coli* (25 µg) was combined with (lane 6) or without (lane 5) 1 mM $K_3Fe(CN)_6$ for 30 min. Lysate (25 µg) and BSA (1.5 µg, lanes 7, 9) or QC-BSA (1.5 µg, lanes 8, 10) were combined with 15 (50 µM) for 30 min in the presence (lanes 9, 10) or absence (lanes 7, 8) of 1 mM $K_3Fe(CN)_6$. After 30 min, all reaction mixtures were quenched with excess 1 and 5 and analyzed by Western blot probing with α-biotin-HRP. Protein loading was verified by Ponceau Stain. The bands denoted with an asterisk represent an endogenously biotinylated *E. coli* protein.

Compound 15 selectively labeled QC-BSA in a time-dependent manner with very little background labeling of unmodified BSA, even upon prolonged exposure of the Western blot (FIG. 16B). Similarly, when the reaction time was held constant (30 min) and the concentration of 15 was varied, dose-dependent labeling was observed, again with minimal nonspecific reactivity (FIG. 16C). As well, pretreatment of QC-BSA with tetrasulfonated Ni bis(dithiolene) 17 quenched the protein-bound quadricyclane moiety, as demonstrated by reduced labeling with 15 (FIG. 16D). To determine whether the quadricyclane ligation possessed the heightened selectivity required to label target biomolecules within more complex samples, 1.5 μg of QC-BSA (or unmodified BSA) was combined with 25 μg of E. coli lysate. This mixture was treated with 50 μM 15 for 30 min, then quenched as above and analyzed by Western blot. Selective labeling of QC-BSA was observed but the signal was weak (FIG. 17). The diminished signal could be due to reduction of 15 by a species present in the lysate. When $K_3Fe(CN)_6$ (1 mM) was added to the reaction mixture, robust and selective labeling of QC-BSA was observed (FIG. 16E).

Figure 18:
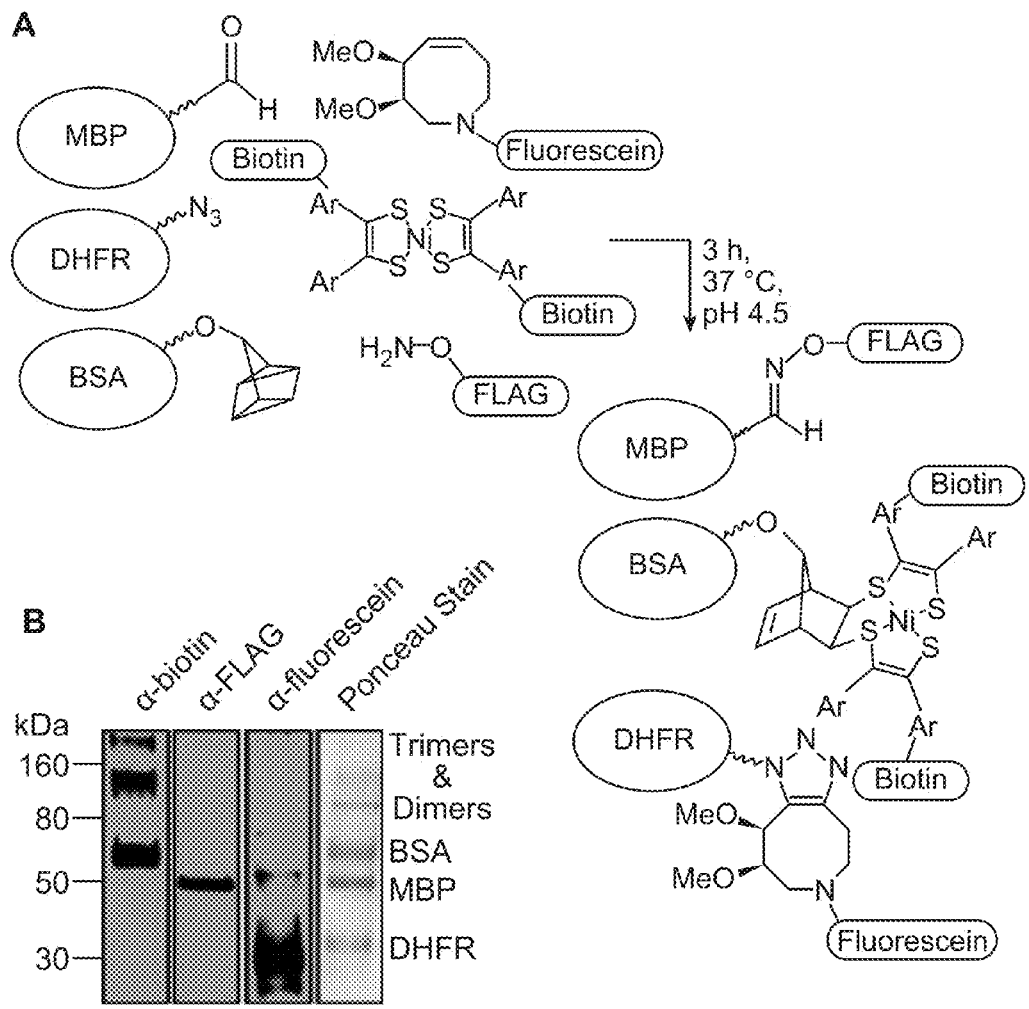
FIGS. 18A and B show that the quadricyclane ligation is orthogonal to Cu-free click chemistry and the oxime ligation. A. A mixture of 8 µg of QC-BSA, AzDHFR, and CHO-MBP was treated with 15 (150 µM), DIMAC-fluor (250 µM), and $H_2NO$-FLAG (1 mM) for 3 h at 37° C., pH 4.5. This mixture was basified with 850 mM tris buffer and quenched with excess 1, 5, and 2-azidoethanol. It was then separated into 3 portions and each portion was analyzed by Western blot probing with a different antibody: α-biotin-HRP (quadricyclane ligation), α-fluorescein-HRP (Cu-free click chemistry) or α-FLAG-HRP (oxime ligation). The Ponceau stain indicates all three proteins were present. Oligomer bands are observed for BSA and DHFR.

New additions to the bioorthogonal reaction compendium are powerful when they can be used in conjunction with other bioorthogonal chemistries. Thus, whether the quadricyclane ligation can be performed simultaneously with two established bioorthogonal reactions, Cu-free click chemistry and oxime formation, which are already known to be mutually compatible was determined. A mixture containing equal amounts of QC-BSA (mw~66 kDa), azidohomoalanine-containing dihydrofolate reductase (AzDHFR, mw~23 kDa), and aldehyde-tagged maltose binding protein (CHO-MBP, mw~42 kDa) was treated with nickel complex 15, an azacyclooctyne conjugated to fluorescein (DIMAC-fluor), and an aminooxy-functionalized FLAG peptide ($H_2NO$-FLAG) (FIG. 18A). After incubation for 3 hours, the mixture was separated into 3 portions and each was analyzed by Western blot probing with one of the following antibodies (where "α" is "anti"): α-biotin-HRP, α-fluorescein-HRP, or α-FLAG-HRP (FIG. 18B).

Western Blot Procedures

The described protein mixture was quenched with diethyldithiocarbamate 5 (9.6 mM), quadricyclane 1 (9.6 mM), 2-azidoethanol (14.5 mM), and excess 850 mM tris buffer pH 7.2 until the pH was neutralized. 4×SDS loading buffer (with BME) was added and the mixture was separated into three equal portions and loaded onto a 4-12% BisTris gel (BioRAD, Criterion). The gel was run at 150 V in MES buffer. Proteins were transferred to nitrocellulose (0.45 BioRAD) over 120 min at 50 V. The nitrocellulose was then treated with Ponceau stain and separated into three sections. Two sections were incubated in BSA blocking buffer (5% BSA in PBST) and the third was incubated with milk blocking buffer (5% non-fat milk in PBST) for 2 h at rt. One BSA-blocked blot was incubated with α-biotin-HRP (1:100,000). The other BSA-blocked blot was incubated with α-fluorescein-HRP (1:100,000, Invitrogen) and the milk-blocked blot was incubated with α-FLAG-HRP (1:100,000, Sigma, M2 monoclonal). All incubations were performed for 1 h at rt and followed by washing with PBST (3×10 min). Detection was performed by chemiluminescence using Pierce SuperSignal West Pico Chemiluminescent Substrate.

As shown in FIG. 18B, each labeling reagent, including 15, reacted only with its complementary bioorthogonal partner. Like the cyclooctyne and aminooxy probes, compound 15 showed no significant labeling of proteins lacking its partner (quadricyclane), nor did it interfere with the other bioorthogonal reactions. Notably, the conditions of this multiplexed reaction (i.e., pH (4.5), temperature (37° C.) and time (3 h)) were tuned to accommodate the oxime ligation, the most sluggish of the three transformations. The quadricyclane ligation was quite tolerant of these conditions.

Figure 19:
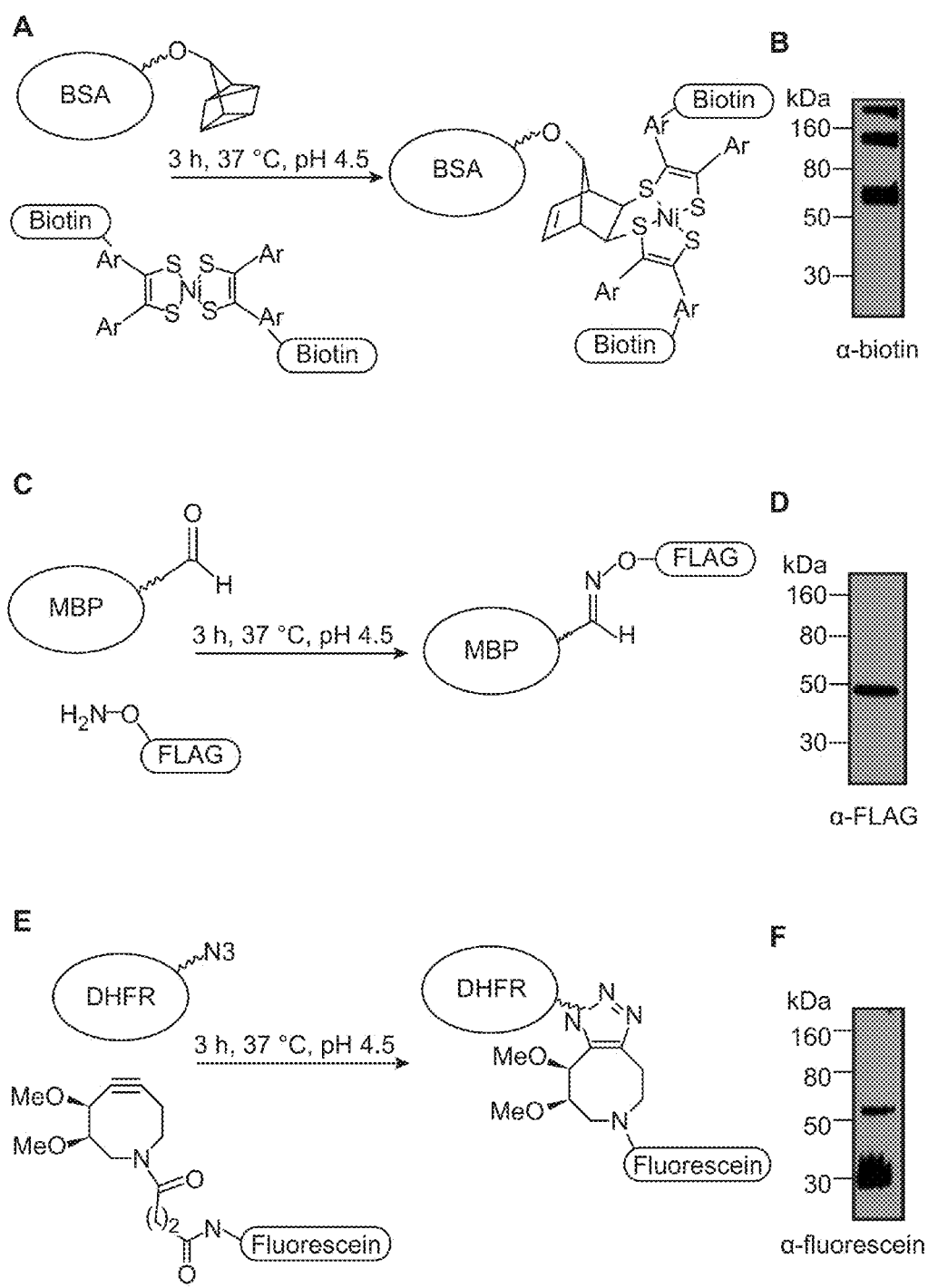
FIGS. 19A-F show controls for the banding patterns seen in FIG. 18B. A/B. QC-BSA (8 µg) and 15 (150 µM) were combined 37° C., pH 4.5. After 3 h, this mixture was basified with 850 mM tris buffer and quenched with excess 1, 5, and 2-azidoethanol. It was then analyzed by Western blot probing with an α-biotin-HRP (B). C/D. CHO-MBP (8 µg) and $H_2NO$-FLAG (1 mM) were combined at 37° C., pH 4.5. After 3 h, this mixture was basified with 850 mM tris buffer and quenched with excess 1, 5, and 2-azidoethanol. It was then analyzed by Western blot probing with an α-FLAG-HRP antibody (D). E/F. AzDHFR (8 µg) and DIMAC-fluor (250 µM) were combined at 37° C., pH 4.5. After 3 h, this mixture was basified with 850 mM tris buffer and quenched with excess 1, 5, and 2-azidoethanol. It was analyzed by Western blot probing with an α-fluorescein-HRP antibody (F).

Controls for the banding patterns seen in FIG. 17B are shown in FIG. 19. In FIG. 19A/B, QC-BSA (8 μg) and 15 (150 μM) were combined 37° C., pH 4.5. After 3 h, this mixture was basified with 850 mM tris buffer and quenched with excess 1, 5, and 2-azidoethanol. It was then analyzed by Western blot probing with an α-biotin-HRP (FIG. 19B). In FIG. 19C/D, CHO-MBP (8 μg) and $H_2NO$-FLAG (1 mM) were combined at 37° C., pH 4.5. After 3 h, this mixture was basified with 850 mM tris buffer and quenched with excess 1, 5, and 2-azidoethanol. It was then analyzed by Western blot probing with an α-FLAG-HRP antibody (FIG. 19D). In FIG. 19E/F, AzDHFR (8 μg) and DIMAC-fluor (250 μM) were combined at 37° C., pH 4.5. After 3 h, this mixture was basified with 850 mM tris buffer and quenched with excess 1, 5, and 2-azidoethanol. It was analyzed by Western blot probing with an α-fluorescein-HRP antibody (FIG. 19F).

Example 3

Toxicity Analysis

Jurkat cells (human T-cell lymphoma) were maintained in RPMI-1640 media (Invitrogen Life Technologies) supplemented with 10% fetal bovine serum (FBS), penicillin (100 units/mL), and streptomycin (0.1 mg/mL) in a 5% $CO_2$ water-saturated atmosphere. The cells were maintained at densities between $1\times10^5$ and $1.6\times10^6$ cells/mL.

Figure 20:
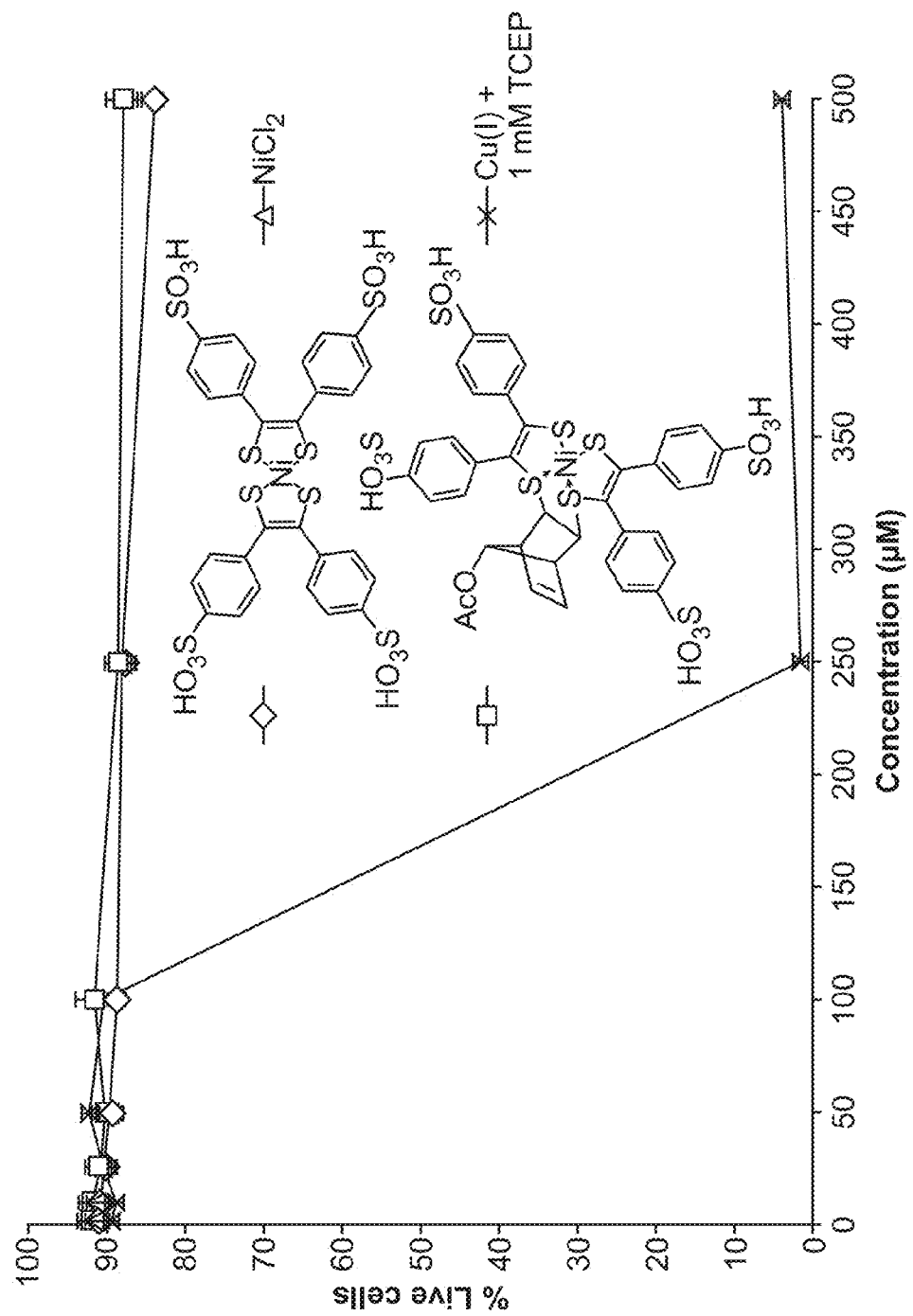
FIG. 20 shows cytotoxicity of 17 and the adduct of 1 and 17 in relation to $NiCl_2$ and Cu(I). Jurkat cells were washed twice with FACS buffer (PBS with 1% FBS) and placed in a 96-well plate with ~400,000 cells/well (pellet 2500×g, 3 min, 4° C.). The cells were treated with at 0, 10, 25, 50, 100, 250, or 500 µM of 17 (blue diamond), the product of 1 and 17 (red square), NiCl$_2$ (purple triangle), or CuSO$_4$ in the presence of 1 mM TCEP (green cross) for 1 h. The cells were washed three times by resuspension in FACS buffer (200 µL) followed by concentration by centrifugation (2500×g, 3 min, 4° C.). Following the third wash, the cells were resuspended in 100 µL of 1× binding buffer containing 5 µL of 7-AAD and 5 µL of FITC-AnnexinV (buffer and reagents from BD Pharmingen™). The cells were incubated at rt in the dark for 15 min, diluted to 500 µL with binding buffer and analyzed by flow cytometry (FL1 vs. FL3) on a BD Biosciences FACSCalibur flow cytometer equipped with a 488-nm argon laser. Plotted is the percentage of cells that do not stain with either 7-AAD or FITC-Annexin-V. The error bars represent the standard deviation of three replicate samples.

FIG. 20 shows cytotoxicity of 17 and the adduct of 1 and 17 in relation to $NiCl_2$ and Cu(I). Jurkat cells were washed twice with FACS buffer (PBS with 1% FBS) and placed in a 96-well plate with ~400,000 cells/well (pellet 2500×g, 3 min, 4° C.). The cells were treated with at 0, 10, 25, 50, 100, 250, or 500 μM of 17 (blue diamond), the product of 1 and 17 (red square), $NiCl_2$ (purple triangle), or $CuSO_4$ in the presence of 1 mM TCEP (green cross) for 1 h. The cells were washed three times by resuspension in fluorescence activated cell sorting (FACS) buffer (200 μL) followed by concentration by centrifugation (2500×g, 3 min, 4° C.). Following the third wash, the cells were resuspended in 100 μL of 1× binding buffer containing 5 μL of 7-Aminoactinomycin D (7-AAD) and 5 μL of fluorescein isothiocyanate (FITC)-AnnexinV (buffer and reagents from BD Pharmingen™). The cells were incubated at room temperature in the dark for 15 min, diluted to 500 μL with binding buffer and analyzed by flow cytometry (FL1 vs. FL3) on a BD Biosciences FACSCalibur flow cytometer equipped with a 488-nm argon laser. Plotted is the percentage of cells that do not stain with either 7-AAD or FITC-Annexin-V. The error bars represent the standard deviation of three replicate samples.

Figure 21:
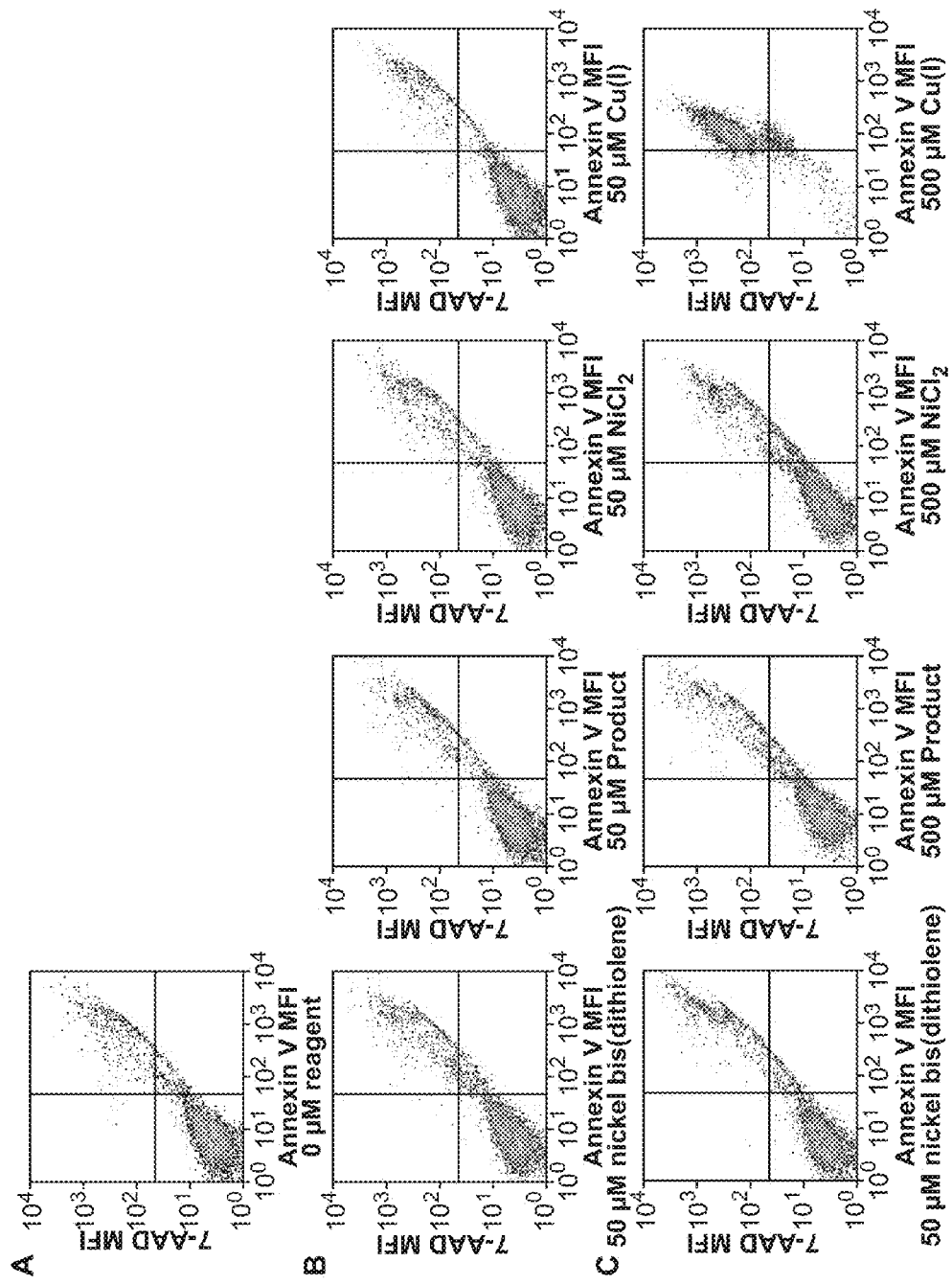
FIGS. 21A-C show representative dot plots for the experiment in FIG. 20. A. Cells treated with no reagent. B. Cells treated with 50 µM of reagent. C. Cells treated with 500 µM reagent. The percentage of cells in the bottom left quadrant is what is plotted in FIG. 20. MFI=mean fluorescence intensity (arbitrary units).

FIG. 21 shows representative dot plots for the experiment in FIG. 20. FIG. 21A shows cells treated with no reagent. FIG. 21B shows cells treated with 50 μM of reagent. FIG. 21C shows cells treated with 500 μM reagent. The percentage of cells in the bottom left quadrant is what is plotted in FIG. 20. MFI=mean fluorescence intensity (arbitrary units).

Figure 22:
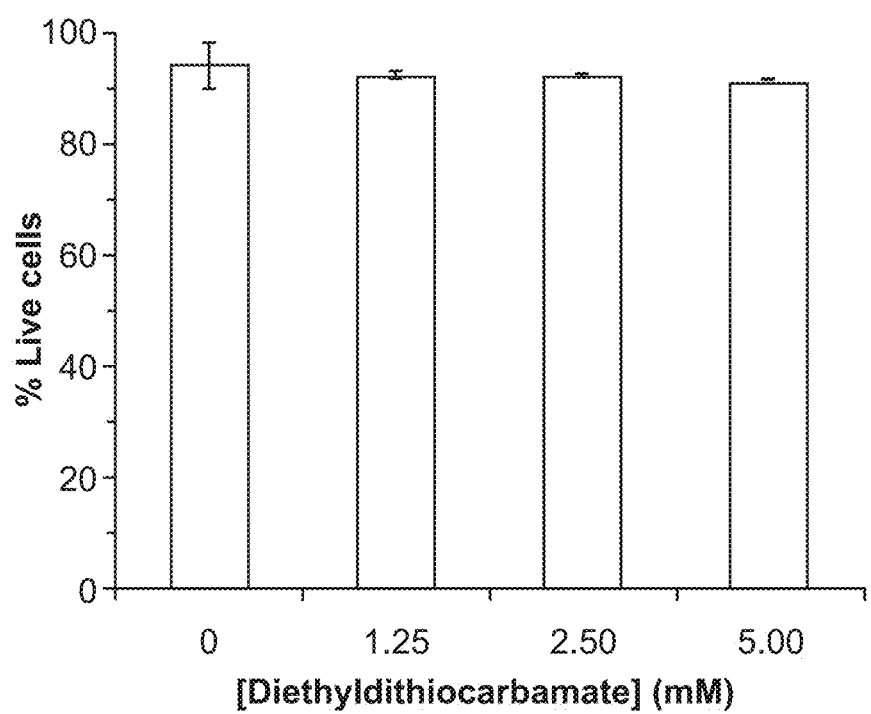
FIG. 22 shows cytotoxicity of diethyldithiocarbamate (5). Jurkat cells were washed twice with FACS buffer (PBS with 1% FBS) and placed in a 96-well plate with ~500,000 cells/well (pellet 2500×g, 3 min, 4° C.). The cells were treated with 0, 1.25, 2.5, or 5.0 mM of 5 for 1 h. The cells were washed three times by resuspension in FACS buffer (200 µL) followed by concentration by centrifugation (2500×g, 3 min, 4° C.). Following the third wash, the cells were resuspended in 100 µL of 1× binding buffer and 7.5 µL of 7-AAD and 5 µL of AnnexinV-PE were added (buffer and reagents from BD Pharmingen™). The cells were incubated at rt in the dark for 15 min, diluted to 500 µL with binding buffer and analyzed by flow cytometry (FL2 vs. FL3) on a BD Biosciences FACSCalibur flow cytometer equipped with a 488-nm argon laser. Plotted is the percentage of cells that do not stain with either 7-AAD or AnnexinV-PE. The error bars represent the standard deviation of three replicate samples.

FIG. 22 shows cytotoxicity of diethyldithiocarbamate (5). Jurkat cells were washed twice with FACS buffer (PBS with 1% FBS) and placed in a 96-well plate with ~500,000 cells/well (pellet 2500×g, 3 min, 4° C.). The cells were treated with 0, 1.25, 2.5, or 5.0 mM of 5 for 1 h. The cells were washed three times by resuspension in FACS buffer (200 μL) followed by concentration by centrifugation (2500×g, 3 min, 4° C.). Following the third wash, the cells were resuspended in 100 μL of 1× binding buffer and 7.5 μL of 7-AAD and 5 μL of AnnexinV-PE were added (buffer and reagents from BD Pharmingen). The cells were incubated at room temperature in the dark for 15 min, diluted to 500 μL with binding buffer and analyzed by flow cytometry (FL2 vs. FL3) on a BD Biosciences FACSCalibur flow cytometer equipped with a 488-nm argon laser. Plotted is the percentage of cells that do not stain with either 7-AAD or AnnexinV-PE. The error bars represent the standard deviation of three replicate samples.

Figure 23:
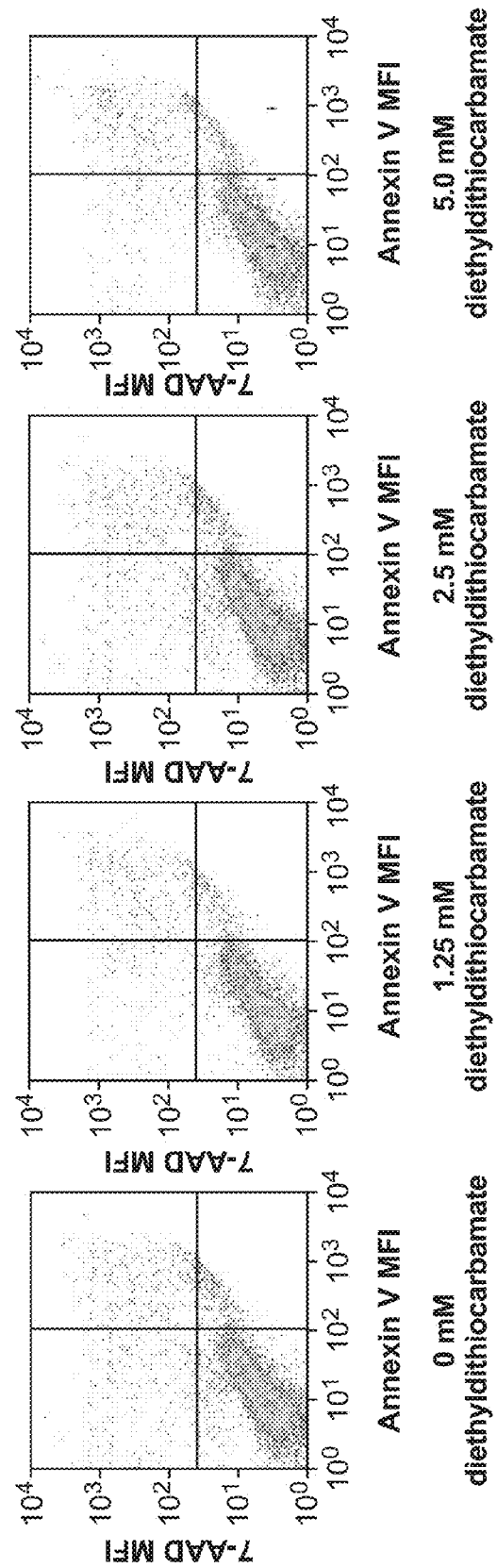
FIG. 23 shows representative dot plots for the experiment in FIG.ure S20. The percentage of cells in the bottom left quadrant is what is plotted in FIG.ure S20. MFI=mean fluorescence intensity (arbitrary units).

FIG. 23 shows representative dot plots for the experiment in FIG. 22. The percentage of cells in the bottom left quadrant is what is plotted in FIG. 22. MFI=mean fluorescence intensity (arbitrary units).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The invention claimed is:

1. A metal bis(dithiolene) compound of the formula (Ia) or (Ic):

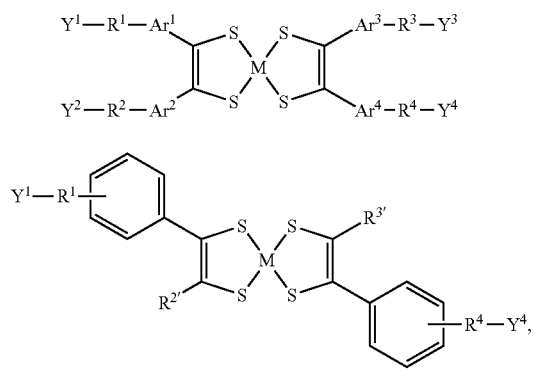

(Ia)

(Ic)

wherein

M is selected from one of the following: nickel (II), palladium (II), platinum (II), cobalt (I), iridium (I), rhodium (I), copper (II), copper (III), silver (III), gold (III), tungsten, and iron;

$Ar^1$, $Ar^2$, $Ar^3$, and $Ar^4$ are independently selected from aryl, substituted aryl, heteroaryl, and substituted heteroaryl groups;

$R^1$, $R^2$, $R^3$, and $R^4$ are optional and are independently selected from alkylene, substituted alkylene, alkenylene, substituted alkenylene, alkynylene, substituted alkynylene, alkoxy, substituted alkoxy, aryl, substituted aryl, acyl, acylamino, aminoacyl, aminocarbonylamino, acyloxy, aminosulfonyl, sulfonylamino, amino, substituted amino, carboxyl ester, sulfonyl, sulfonyloxy, and thioalkoxy;

$R^2$ and $R^3$ are independently selected from the following: hydrogen, alkyl, substituted alkyl, alkenyl, substituted alkenyl, alkynyl, substituted alkynyl, alkoxy, substituted alkoxy, aryl, substituted aryl, acyl, acylamino, aminoacyl, aminocarbonylamino, acyloxy, aminosulfonyl, sulfonylamino, amino, substituted amino, carboxyl ester, sulfonyl, sulfonyloxy, and thioalkoxy: and $Y^1$, $Y^2$, $Y^3$, and $Y^4$ are independently selected from hydrogen; halogen; a moiety that comprises a reactive group that facilitates covalent attachment of a molecule of interest and is selected from the group consisting of amine, ester, thioester, sulfonyl halide, alcohol, thiol, succinimyl ester, isothiocyanate, iodoacetamide, maleimide, hydrazine, aminooxy, aldehyde, ketone, nitrile oxide, nitrone, tetrazine, azirine, tetrazole, alkene, alkyne, cyclooctyne, trans-cyclooctene, norbornene, and azide; and a molecule of interest;

wherein at least one of $Y^1$, $Y^2$, $Y^3$, and $Y^4$ is the molecule of interest;

wherein the molecule of interest is selected from a peptide, an antigen-binding fragment of an antibody, an antibody and an epitope tag.

2. The metal bis(dithiolene) compound of claim 1, wherein the compound is of the formula:

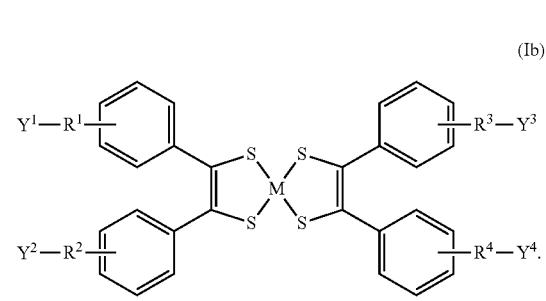

(Ib)

3. A metal bis(dithiolene) compound of the formula (Ia) or (Ic):

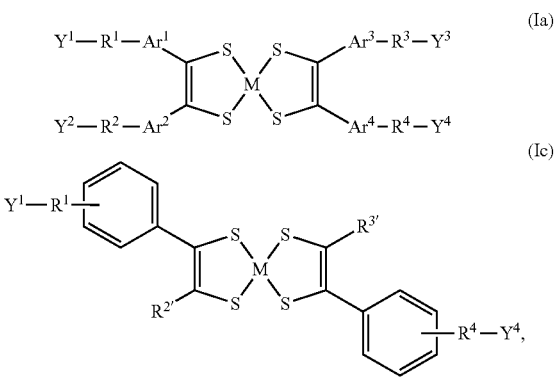

(Ia)

(Ic)

wherein

M is selected from one of the following: gold (III), tungsten, and iron;

$R^{2'}$ and $R^{3'}$ are independently selected from the following: hydrogen, alkyl, substituted alkyl, alkenyl, substituted alkenyl, alkynyl, substituted alkynyl, alkoxy, substituted alkoxy, aryl, substituted aryl, acyl, acylamino, aminoacyl, aminocarbonylamino, acyloxy, aminosulfonyl, sulfonylamino, amino, substituted amino, carboxyl ester, sulfonyl, sulfonyloxy, and thioalkoxy;

$R^1$, $R^2$, $R^3$ and $R^4$ are optional and are independently selected from alkylene, substituted alkylene, alkenylene, substituted alkenylene, alkynylene, substituted alkynylene, alkoxy, substituted alkoxy, aryl, substituted aryl, acyl, acylamino, aminoacyl, aminocarbonylamino, acyloxy, aminosulfonyl, sulfonylamino, amino, substituted amino, carboxyl ester, sulfonyl, sulfonyloxy, and thioalkoxy; and $Y^1$, $Y^2$, $Y^3$ and $Y^4$ are independently selected from hydrogen; halogen; a moiety that comprises a reactive group that facilitates covalent attachment of a molecule of interest and is selected from the group consisting of amine, ester, thioester, sulfonyl halide, alcohol, thiol, succinimyl ester, isothiocyanate, iodoacetamide, maleimide, hydrazine, aminooxy, aldehyde, ketone, nitrile oxide, nitrone, tetrazine, azirine, tetrazole, alkene, alkyne, cyclooctyne, trans-cyclooctene, norbornene, and azide; and a molecule of interest;

wherein at least one of $Y^1$ and $Y^4$ is the molecule of interest;

wherein the molecule of interest is selected from the group consisting of a radioactive label, a positron emission tomography (PET) imaging label, a peptide, a drug, biotin, an antigen-binding fragment of an antibody, an antibody and an epitope tag.

4. The compound of any one of claims 1 and 2, wherein M is selected from gold (III), tungsten, and iron.

5. The compound of any one of claims 1 and 2, wherein M is selected from nickel (II), palladium (II), and platinum (II).

6. The compound of claim 1, wherein Ar¹, Ar², Ar³, and Ar⁴ are each independently heteroaryl, or substituted heteroaryl groups.

7. The compound of claim 1 wherein Ar¹, Ar², Ar³, and Ar⁴ are each independently aryl or substituted aryl.

8. The compound of claim 3 wherein the compound is of the formula (Ic) and $R^{2'}$ and $R^{3'}$ are each substituted aryl.

9. The compound of any one of claims 1-3, wherein the compound is of the formula (Ia) and Ie, $R^1$, $R^2$, $R^3$, or $R^4$ is alkylene, substituted alkylene, alkenylene, substituted alkenylene, alkynylene, or substituted alkynylene.

10. The compound of claim 2 wherein $R^2$ and $R^3$ are independently selected from aryl, substituted aryl, alkyl or substituted alkyl.

11. The compound of claim 1 wherein the compound is of the formula:

12. A compound of the formula:

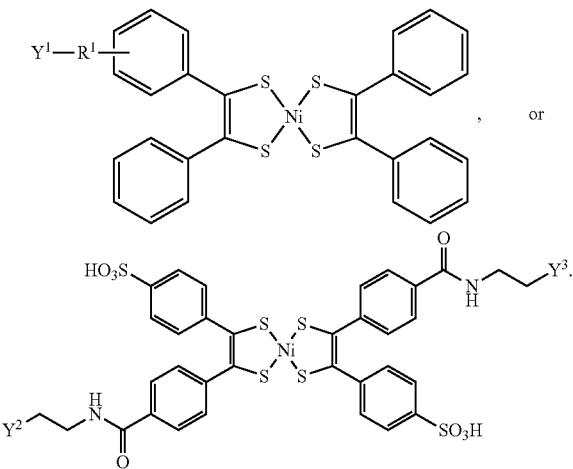

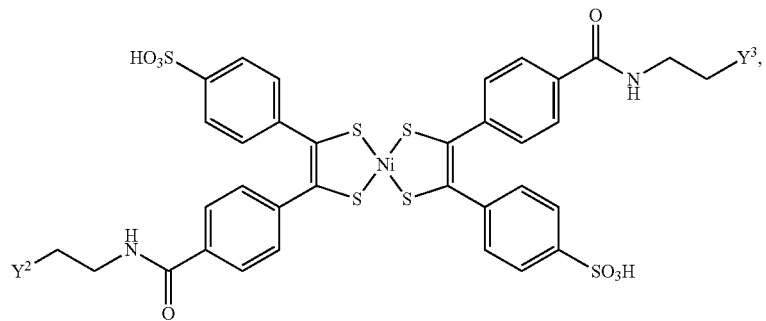

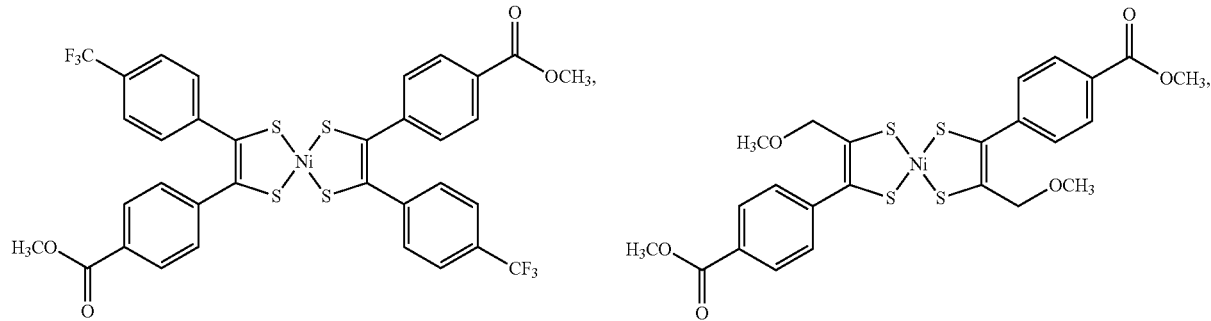

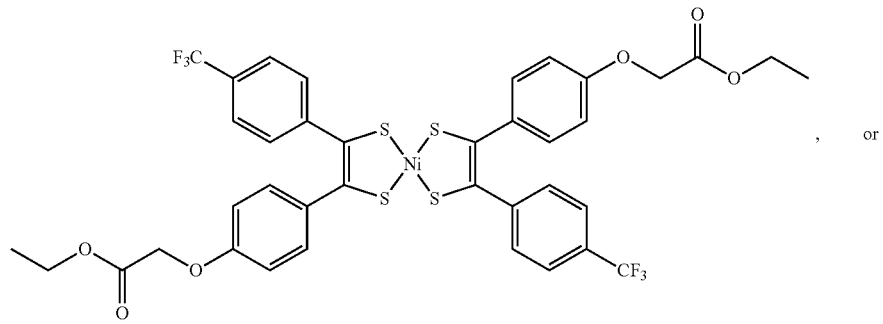

-continued

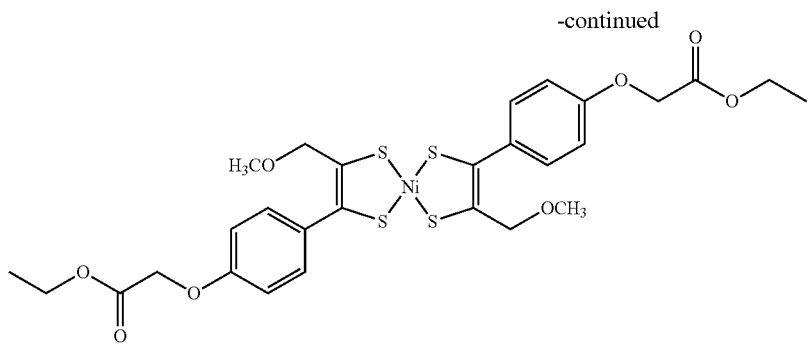

wherein $Y^2$ and $Y^3$ are independently selected from hydrogen; halogen; and a moiety that comprises a reactive group that facilitates covalent attachment of a molecule of interest and is selected from amine, ester, thioester, sulfonyl halide, alcohol, thiol, succinimyl ester, isothiocyanate, iodoacetamide, maleimide, hydrazine, aminooxy, aldehyde, ketone, nitrile oxide, nitrone, tetrazine, azirine, tetrazole, alkene, alkyne, cyclooctyne, trans-cyclooctene, norbornene and azide.

13. The compound of claim 3, wherein the molecule of interest is selected from a peptide, a drug, an antigen-binding fragment of an antibody, an antibody and an epitope tag.

14. The compound of claim 13, wherein the molecule of interest is selected from a peptide, an epitope tag, an antigen-binding fragment of an antibody and an antibody.

15. The compound of claim 13, wherein the molecule of interest is a drug.

* * * * *

```
                        SEQUENCE LISTING

<160> NUMBER OF SEQ ID NOS: 4

<210> SEQ ID NO 1
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 1

Cys Tyr Pro Tyr Asp Val Pro Asp Tyr Ala
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 2

Asp Tyr Lys Asp Asp Asp Asp Lys
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 3

Asp Tyr Lys Asp Asp Asp Asp Lys Cys
1               5

<210> SEQ ID NO 4
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 4

Cys Glu Gln Lys Leu Ile Ser Glu Glu Asp Leu
1               5                   10
```